(12) United States Patent
Dickerson et al.

(10) Patent No.: US 7,582,630 B2
(45) Date of Patent: Sep. 1, 2009

(54) PYRADAZINE COMPOUNDS AS GSK-3 INHIBITORS

(75) Inventors: Scott Howard Dickerson, Durham, NC (US); Francis Xavier Tavares, Durham, NC (US); Huiqiang Zhou, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 575 days.

(21) Appl. No.: 10/530,985

(22) PCT Filed: Oct. 14, 2003

(86) PCT No.: PCT/US03/32473

§ 371 (c)(1),
(2), (4) Date: Apr. 12, 2005

(87) PCT Pub. No.: WO2004/035588

PCT Pub. Date: Apr. 29, 2004

(65) Prior Publication Data

US 2006/0069097 A1    Mar. 30, 2006

Related U.S. Application Data

(60) Provisional application No. 60/418,522, filed on Oct. 15, 2002.

(51) Int. Cl.
*A01N 43/60* (2006.01)
*A01N 43/58* (2006.01)
*A61K 31/495* (2006.01)
*A61K 31/50* (2006.01)
*C07D 487/00* (2006.01)

(52) U.S. Cl. ...................... 514/248; 544/236
(58) Field of Classification Search ...................... None
See application file for complete search history.

(56) References Cited

U.S. PATENT DOCUMENTS 4,313,734 A    2/1982   Leuvering
4,744,760 A    5/1988   Molday
7,279,473 B2 * 10/2007  Badiang et al. .......... 514/233.2

FOREIGN PATENT DOCUMENTS

WO    WO 03051886    *    6/2003

OTHER PUBLICATIONS

Vippagunta et. al. Advanced Drug Delivery Reviews 48 (2001) 3-26.*
Dorwald F. A. Side Reactions in Organic Synthesis, 2005, Wiley: VCH, Weinheim p. IX of Preface.*

* cited by examiner

*Primary Examiner*—James O Wilson
*Assistant Examiner*—Jeffrey H Murray
(74) *Attorney, Agent, or Firm*—John L. Lemanowicz; Kathryn L. Coulter

(57) ABSTRACT

The present invention relates to pyrazaolpyradazine derivatives that inhibit GSK3 (glycogen synthase kinase), pharmaceutical compositions containing these derivatives, and methods for their use in the treatment of disorder characterized by misregulation of GSK3.

8 Claims, No Drawings

PYRADAZINE COMPOUNDS AS GSK-3 INHIBITORS

FIELD OF THE INVENTION

This application is filed pursuant to 35 U.S.C. § 371 as a United States National Phase Application of International Application No. PCT/US2003/032473 filed Oct. 14, 2003, which claims priority from U.S. 60/418,522 filed Oct. 15, 2002.

The present invention relates generally to inhibitors of the kinases, such as GSK3, and more particularly to fused pyradazine compounds.

BACKGROUND OF THE INVENTION

The present invention provides compounds that are useful pharmacological agents for disease states that are mediated (for example, alleviated) through the inhibition or antagonism, of protein kinases. In particular, the present invention relates to compounds that demonstrate protein tyrosine kinase and/or protein serine/threonine kinase inhibition.

The protein kinases represent a large family of proteins which play a central role in the regulation of a wide variety of cellular processes and maintaining control over cellular function (Hanks, et al., *Science*, 1988, 241, 42-52). The loss of control over cellular regulation can often lead to aberrant cell function or death, often resulting in a disease state in the parent organism. Inhibitors of certain kinases may also have utility in the treatment of diseases when the kinase is not misregulated, but is nonetheless essential for maintenance of the disease state. In this case, inhibition of the kinase activity would act either as a cure or palliative for these diseases.

As noted above, GSK3 (glycogen synthase kinase) is identified as a kinase useful in the treatment of type II diabetes. GSK3 inhibits glycogen synthase by direct phosphorylation. Upon insulin activation, GSK3 is inactivated, thereby allowing the activation of glycogen synthase and possibly other insulin-dependent events.

Type II diabetes, otherwise known as Non-insulin Dependent Diabetes Mellitus (NIDDM), is initially characterized by decreased sensitivity to insulin (insulin resistance) and a compensatory elevation in circulating insulin concentrations. Increased insulin levels are caused by increased secretion from the pancreatic beta cells in an attempt to overcome the insulin resistance. The resulting hyperinsulinemia is associated with a variety of cardiovascular complications.

As insulin resistance worsens, the demand on the pancreatic beta cells steadily increases until the pancreas can no longer provide adequate levels of insulin, thereby resulting in elevated levels of glucose in the blood. Thus, diabetes causes impaired glucose transport into skeletal muscle and increased hepatic glucose production, in addition to inadequate insulin response. The disorders and conditions associated with hyperglycemia and hyperlipidemia include cardiovascular disease, renal failure, and blindness.

GSK3 inhibition stimulates insulin-dependent processes and is consequently useful in the treatment of diseases and conditions, such as type II diabetes, that are mediated by GSK3 activity, or, more specifically, characterized by a need for the inhibition of GSK3.

For example, Klein et al., *PNAS* 93:8455-9 (1996) report that lithium ion inhibits GSK3 activity. Lithium has been reported to have anti-diabetic effects such as reduction of plasma glucose levels, increased glycogen uptake, potentiation of insulin, and stimulation of glycogen synthesis in skin, muscle, and fat cells. Lithium, however, effects molecular targets other than GSK3, and is, therefore, not a widely accepted therapy for diabetics.

GSK3 is a proline-directed serine/threonine kinase. Other examples of GSK3 mediated diseases or conditions include, without limitation, obesity, various CNS disorders such as Alzheimer's Disease, bipolar disorder, and schizophrenia, neurotraumatic injuries such as acute stroke, immune potentiation, baldness or hair loss, atherosclerotic cardiovascular disease, hypertension, polycystic ovary syndrome, ischemia, brain trauma or injury, immunodeficiency, and cancer. See, for example, published PCT application WO 00/38675, the background of which is herein incorporated by reference.

Thus, the compounds of the present invention are believed useful is a variety of disease states, each of which may be characterized as mediated by inhibition or antagonism of protein kinases, more specifically GSK-3.

SUMMARY OF THE INVENTION

The present invention includes compounds of Formula (I):

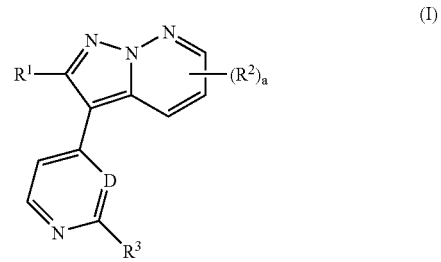

as well as salts, solvates, or physiologically functional derivatives thereof, wherein D is N or CH;

$R^1$ is aryl or heteroaryl, where said aryl or said heteroaryl may be optionally substituted one or more times with $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, oxo, hydroxy, mercapto, carboxy, tetrazolyl, carbamoyl optionally substituted with alkyl, aminosulfonyl optionally substituted by alkyl, acyl, aroyl, heteroaroyl, acyloxy, aroyloxy, heteroaroyloxy, alkoxycarbonyl, halogen, $C_1$-$C_6$ haloalkyl, heterocyclyl, heteroaryl, aryl, cyano, azido, nitro, or —$NR^4R^5$;

a is 1 or 2;

y is 0, 1, or 2;

$R^2$ is hydrogen, $C_1$-$C_6$ alkyl, $C_1$-$C_6$ alkenyl, $C_1$-$C_6$ alkynyl, $C_1$-$C_6$ haloalkyl, $C_3$-$C_7$ cycloalkyl, halogen, heterocyclyl, aryl, heteroaryl, cyano, azido, nitro, —$OR^8$, —$OR^6R^8$, —$R^6R^7$, —$R^6R''$, $S(O)_yR^7$, —$C(O)R^7$, —$C(O)OR^7$, —$C(O)NR^4R^5$, —$NR^i(C=NR^4)NR^4R^5$, —$OC(O)NR^4R^5$, —$OC(O)OR^7$, —$C(=NR^4)NR^4R^5$, —$NR^4R^5$, —$OC(O)R^7$, or —$NR^7C(O)R^7$;

$R^3$ is -(Q)$_p$-(Q$^1$)

where
  Q is O, N($R^8$) or S(O)$_y$,
  p is 0 or 1,
  y is 0, 1, or 2, and
  $Q^1$ is $C_1$-$C_6$ alkyl, $C_3$-$C_7$ cycloalkyl, $C_1$-$C_6$ haloalkyl, aryl, aryl substituted with —C(O)N(H)$R^6$N$R^4R^5$ or —OC(H)(OH)$R^6$N$R^4R^5$, heteroaryl, aralkyl, or —$R^6$N$R^4R^5$;

$R^4$ and $R^5$ are independently hydrogen, $C_1$-$C_3$ alkyl, $C_3$-$C_7$ cycloalkyl, or $R^4$ and $R^5$ together with the nitrogen atom to which they are bound form a heterocyclyl;

$R^6$ is alkylene, arylene, heteroarylene, cycloalkylene, alkenylene, cycloalkenylene, or alkynylene;

$R^7$ is hydrogen, $C_1$-$C_6$ alkyl, $C_1$-$C_6$ alkenyl, $C_1$-$C_6$ alkynyl, —$NR^4R^5$, aryl, aralkyl, heteroaryl, cycloalkyl, heterocyclyl, —$S(O)_yR^8$, —$C(O)R^8$, —$C(O)OR^8$, —$C(O)NR^4R^5$, —$S(O)_2NR^4R^5$, —NR'(C=$NR^4$)$NR^4R^5$, —OC(O)$NR^4R^5$, —OC(O)$OR^8$, —C(=$NR^4$)$NR^4R^5$, —$NR^4R^5$, or —$NR^7C(O)R^7$;

$R^8$ is hydrogen, $C_1$-$C_6$ alkyl, $C_1$-$C_6$ alkenyl, $C_1$-$C_6$ alkynyl, —$NR^4R^5$, aryl, aralkyl; heteroaryl, cycloalkyl, heterocyclyl, or —$S(O)_2R^9$;

$R^9$ is $C_1$-$C_6$ alkyl or $C_1$-$C_6$ haloalkyl;

R' is $C_1$-$C_3$ alkylene; and

R" is —$OR^7$, —OC(O)$NR^4R^5$, —OC(O)$OR^7$, —OC(O)$R^7$.

Preferably $R^1$ is optionally substituted aryl. More preferably $R^1$ is optionally substituted phenyl. More preferably $R^1$ is phenyl is substituted in the para position.

Preferably $R^3$ is further defined wherein Q is $N(R^8)$, where $R^8$ is H, p is 1, and $Q^1$ is optionally substituted aryl. More preferably $Q^1$ is optionally substituted phenyl. More preferably the phenyl is substituted in the meta or para position.

Another aspect of the present invention includes a method for the treatment or prophylaxis of a disorder in a mammal, said disorder being characterized by misregulation of GSK-3, comprising administering compound of Formula (I):

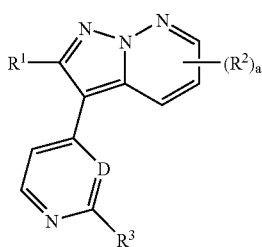

(I)

including a salt, solvate, or physiologically functional derivative thereof, wherein D is N or CH;

$R^1$ is defined more broadly than hereinabove to include hydrogen, $C_1$-$C_6$ alkyl, $C_1$-$C_4$ alkenyl, $C_1$-$C_4$ alkynyl, $C_1$-$C_3$ alkoxy, halogen, hydroxy, cyano, —$S(O)_yC_1$-$C_3$ alkyl, —$NR^4R^5$, aryl, or heteroaryl, where said aryl or said heteroaryl may be optionally substituted one or more times with $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, oxo, hydroxy, mercapto, carboxy, tetrazolyl, carbamoyl optionally substituted with alkyl, aminosulfonyl optionally substituted by alkyl, acyl, aroyl, heteroaroyl, acyloxy, aroyloxy, heteroaroyloxy, alkoxycarbonyl, halogen, $C_1$-$C_6$ haloalkyl, heterocyclyl, heteroaryl, aryl, cyano, azido, nitro, or —$NR^4R^5$;

a is 1 or 2;

y is 0, 1, or 2;

$R^2$ is hydrogen, $C_1$-$C_6$ alkyl, $C_1$-$C_6$ alkenyl, $C_1$-$C_6$ alkynyl, $C_1$-$C_6$ haloalkyl, $C_3$-$C_7$ cycloalkyl, halogen, heterocyclyl, aryl, heteroaryl, cyano, azido, nitro, —$OR^8$, —$OR^6R^8$, —$R^6R^7$, —$R^6R''$, $S(O)_yR^7$, —$C(O)R^7$, —$C(O)OR^7$, —$C(O)NR^4R^5$, —NR'(C=$NR^4$)$NR^4R^5$, —OC(O) $NR^4R^5$, —OC(O)$OR^7$, —C(=$NR^4$)$NR^4R^5$, —$NR^4R^5$, —OC(O)$R^7$, —$NR^7C(O)R^7$;

$R^3$ is -(Q)$_p$-(Q$^1$)

where

Q is O, $N(R^8)$ or $S(O)_y$, p is 0 or 1, y is 0, 1, or 2 and $Q^1$ is $C_1$-$C_6$ alkyl, $C_3$-$C_7$ cycloalkyl, $C_1$-$C_6$ haloalkyl, aryl, aryl substituted with —C(O)N(H)$R^6NR^4R^5$ or —OC(H)(OH)$R^6NR^4R^5$; heteroaryl; aralkyl, or —$R^6NR^4R^5$;

$R^4$ and $R^5$ are independently hydrogen, $C_1$-$C_3$ alkyl, $C_3$-$C_7$ cycloalkyl, or $R^4$ and $R^5$, together with the nitrogen atom to which they are bound, form a heterocyclyl;

$R^6$ is alkylene, arylene, heteroarylene, cycloalkylene, alkenylene, cycloalkenylene, and alkynylene;

$R^7$ is hydrogen, $C_1$-$C_6$alkyl, $C_1$-$C_6$alkenyl, $C_1$-$C_6$alkynyl, —$NR^4R^5$, aryl, aralkyl, heteroaryl, cycloalkyl, heterocyclyl, —$S(O)_yR^8$, —$C(O)R^8$, —$C(O)OR^8$, —$C(O)NR^4R^5$, —$S(O)_2NR^4R^5$, —NR'(C=$NR^4$)$NR^4R^5$, —OC(O)$NR^4R^5$, —OC(O)$OR^8$, —C(=$NR^4$)$NR^4R^5$, —$NR^4R^5$, —$NR^7C(O)R^7$ $R^8$ is hydrogen, $C_1$-$C_6$alkyl, $C_1$-$C_6$ alkenyl, $C_1$-$C_6$alkynyl, —$NR^4R^5$, aryl, aralkyl, heteroaryl, cycloalkyl, heterocyclyl, or —$S(O)_2R^9$;

$R^9$ is $C_1$-$C_6$ alkyl or $C_1$-$C_6$ haloalkyl;

R' is $C_1$-$C_3$ alkylene; and

R" is —$OR^7$, —OC(O)$NR^4R^5$, —OC(O)$OR^7$, —OC(O)$R^7$.

Preferably $R^1$ is optionally substituted aryl. More preferably $R^1$ is optionally substituted phenyl. More preferably $R^1$ is phenyl is substituted in the para position.

Preferably $R^3$ is further defined wherein Q is $N(R^8)$, where $R^8$ is H, p is 1, and $Q^1$ is optionally substituted aryl. More preferably $Q^1$ is optionally substituted phenyl. More preferably the phenyl is substituted in the meta or para position. The compound of claim 9 wherein $R^1$ is optionally substituted phenyl.

Preferred compounds of the present invention eliciting important biological response as GSK-3 inhibitors include:

N-Cyclopropyl-4-pyrazolo[1,5-b]pyridazin-3-yl-2-pyrimidinamine;

N-Cyclopropyl-N-methyl-4-pyrazolo[1,5-b]pyridazin-3-yl-2-pyrimidinamine;

4-Pyrazolo[1,5-b]pyridazin-3-yl-N-(2,2,2-trifluoroethyl)-2-pyrimidinamine;

N-Phenyl-4-pyrazolo[1,5-b]pyridazin-3-yl-2-pyrimidinamine;

N-(4-Chlorophenyl)-4-pyrazolo[1,5-b]pyridazin-3-yl-2-pyrimidinamine;

N-(4-Fluorophenyl)-4-pyrazolo[1,5-b]pyridazin-3-yl-2-pyrimidinamine;

3-[(4-Pyrazolo[1,5-b]pyridazin-3-yl-2-pyrimidinyl)amino] benzonitrile;

4-[(4-Pyrazolo[1,5-b]pyridazin-3-yl-2-pyrimidinyl)amino] benzoic acid;

4-Pyrazolo[1,5-b]pyridazin-3-yl-N-[3-(trifluoromethyl)phenyl]-2-pyrimidinamine;

N-(3-Nitrophenyl)-4-pyrazolo[1,5-b]pyridazin-3-yl-2-pyrimidinamine;

N-(2-Chlorophenyl)-4-pyrazolo[1,5-b]pyridazin-3-yl-2-pyrimidinamine;

N-(4-Methoxyphenyl)-4-pyrazolo[1,5-b]pyridazin-3-yl-2-pyrimidinamine;

4-Pyrazolo[1,5-b]pyridazin-3-yl-N-(3,4,5-trimethoxyphenyl)-2-pyrimidinamine;

N-[3-(1,3-Oxazol-5-yl)phenyl]-4-pyrazolo[1,5-b]pyridazin-3-yl-2-pyrimidinamine;

N-(4-Pyrazolo[1,5-b]pyridazin-3-yl-2-pyrimidinyl)-1H-benzimidazol-6-amine;

N-(4-Pyrazolo[1,5-b]pyridazin-3-yl-2-pyrimidinyl)-1,3-benzoxazol-2-amine;

N-(6-Chloro-1H-benzimidazol-2-yl)-N-(4-pyrazolo[1,5-b]pyridazin-3-yl-2-pyrimidinyl)amine;
N-(4-Chlorobenzyl)-4-pyrazolo[1,5-b]pyridazin-3-yl-2-pyrimidinamine;
$N^1,N^1$-Dimethyl-$N^3$-(4-pyrazolo[1,5-b]pyridazin-3-yl-2-pyrimidinyl)-1,3-propanediamine;
N-[3-(4-Morpholinyl)propyl]-4-pyrazolo[1,5-b]pyridazin-3-yl-2-pyrimidinamine;
N-[3-(4-Methyl-1-piperazinyl)propyl]4-pyrazolo[1,5-b]pyridazin-3-yl-2-pyrimidinamine;
1-{3-[(4-Pyrazolo[1,5-b]pyridazin-3-yl-2-pyrimidinyl)amino]propyl}-2-pyrrolidinone;
N-[3-Chloro-4-(4-methyl-1-piperazinyl)phenyl]-4-pyrazolo[1,5-b]pyridazin-3-yl-2-pyrimidinamine;
N-[4-(4-Methyl-1-piperazinyl)phenyl]-4-pyrazolo[1,5-b]pyridazin-3-yl-2-pyrimidinamine;
N-[3-Methyl-4-(4-methyl-1-piperazinyl)phenyl]-4-pyrazolo[1,5-b]pyridazin-3-yl-2-pyrimidinamine;
N-[4-(4-Methyl-1-piperazinyl)-3-(trifluoromethyl)phenyl]-4-pyrazolo[1,5-b]pyridazin-3-yl-2-pyrimidinamine;
N-[3-Chloro-4-(4-morpholinyl)phenyl]-4-pyrazolo[1,5-b]pyridazin-3-yl-2-pyrimidinamine;
N{4-[(Diethylamino)methyl]phenyl}-4-pyrazolo[1,5-b]pyridazin-3-yl-2-pyrimidinamine;
N-[2-(Diethylamino)ethyl]-4-[(4-pyrazolo[1,5-b]pyridazin-3-yl-2-pyrimidinyl)amino]benzamide;
N-Cyclopropyl(2-methylpyrazolo[1,5-b]pyridazin-3-yl)-2-pyrimidinamine;
N-Cyclopropyl-4-(2-ethylpyrazolo[1,5-b]pyridazin-3-yl)-2-pyrimidinamine;
4-(2-Butylpyrazolo[1,5-b]pyridazin-3-yl)-N-cyclopropyl-2-pyrimidinamine;
N-[4-(4-Methyl-1-piperazinyl)phenyl]-4-(2-methylpyrazolo[1,5-b]pyridazin-3-yl)-2-pyrimidinamine;
4-(2-Ethylpyrazolo[1,5-b]pyridazin-3-yl)-N-[4-(4-methyl-1-piperazinyl)phenyl]-2-pyrimidinamine;
4-(2-Butylpyrazolo[1,5-b]pyridazin-3-yl)-N-[4-(4-methyl-1-piperazinyl)phenyl]-2-pyrimidinamine;
N-Cyclopropyl-4-(6-methoxypyrazolo[1,5-b]pyridazin-3-yl)-2-pyrimidinamine;
4-(6-Methoxypyrazolo[1,5-b]pyridazin-3-yl)-N-[4-(4-methyl-1-piperazinyl)phenyl]-2-pyrimidinamine;
3-[2-(Cyclopropylamino)-4-pyrimidinyl]pyrazolo[1,5-b]pyridazin-6-ol;
N-Cyclopropyl-4-(6-isopropoxypyrazolo[1,5-b]pyridazin-3-yl)-2-pyrimidinamine;
N-[4-(6-Isopropoxypyrazolo[1,5-b]pyridazin-3-yl)-2-pyrimidinyl]-N-[4-(4-methyl-1-piperazinyl)phenyl]amine;
3-[2-(Cyclopropylamino)-4-pyrimidinyl]pyrazolo[1,5-b]pyridazin-6-yl trifluoromethanesulfonate;
4-[6-(2-Chlorophenyl)pyrazolo[1,5-b]pyridazin-3-yl]-N-cyclopropyl-2-pyrimidinamine;
N-Cyclopropyl-4-[6-(2-thienyl)pyrazolo[1,5-b]pyridazin-3-yl]-2-pyrimidinamine;
N-Cyclopropyl-4-[6-(4-fluorophenyl)pyrazolo[1,5-b]pyridazin-3-yl]-2-pyrimidinamine;
N-Cyclopropyl-4-[6-(4-vinylpyrazolo[1,5-b]pyridazin-3-yl)-2-pyrimidinamine;
N-Cyclopropyl-4-[6-(4-morpholinyl)pyrazolo[1,5-b]pyridazin-3-yl]-2-pyrimidinamine;
N-Cyclopentyl-3-[2-(cyclopropylamino)-4-pyrimidinyl]pyrazolo[1,5-b]pyridazin-6-amine;
N-Cyclopropyl-4-[6-(1-pyrrolidinyl)pyrazolo[1,5-b]pyridazin-3-yl]-2-pyrimidinamine;
N-Cyclopropyl-4-[6-(2-fluoro-4-pyridinyl)pyrazolo[1,5-b]pyridazin-3-yl]-2-pyrimidinamine;
N-Cyclopropyl-4-[6-(phenylsulfanyl)pyrazolo[1,5-b]pyridazin-3-yl]-2-pyrimidinamine;
4-[6-(4-Fluorophenyl)pyrazolo[1,5-b]pyridazin-3-yl]-N-(4-methoxyphenyl)-2-pyrimidinamine;
4-[6-(4-Fluorophenyl)pyrazolo[1,5-b]pyridazin-3-yl]-N-[4-(4-methyl-1-piperazinyl)phenyl]-2-pyrimidinamine;
$N^1,N^1$-Dimethyl-$N^4$-{4-[6-(4-morpholinyl)pyrazolo[1,5-b]pyridazin-3-yl]-2-pyrimidinyl}-1,4-benzenediamine,
1-(Dimethylamino)-3-[4-({4-[6-(4-morpholinyl)pyrazolo[1,5-b]pyridazin-3-yl]-2-pyrimidinyl}amino)phenoxy]-2-propanol;
N-(1,3-benzodioxol-5-yl)-4-pyrazolo[1,5-b]pyridazin-3-yl-2-pyrimidinamine;
N-(2,3-Dihydro-1,4-benzodioxin-6-yl)-4-pyrazolo[1,5-b]pyridazin-3-yl-2-pyrimidinamine;
N-[3-Methoxy-5-(trifluoromethyl)phenyl]-4-pyrazolo[1,5-b]pyridazin-3-yl-2-pyrimidinamine;
4-[(4-Pyrazolo[1,5-b]pyridazin-3-yl-2-pyrimidinyl)amino]benzonitrile;
N-(4-Nitrophenyl)-4-pyrazolo[1,5-b]pyridazin-3-yl-2-pyrimidinamine;
N-(3-Methoxyphenyl)-4-pyrazolo[1,5-b]pyridazin-3-yl-2-pyrimidinamine;
N-(3,5-Dimethylphenyl)-4-pyrazolo[1,5-b]pyridazin-3-yl-2-pyrimidinamine;
4-[2-(4-methoxyphenyl)pyrazolo[1,5-b]pyridazin-3-yl]-N-phenylpyrimidin-2-amine;
4-[2-(4-methoxyphenyl)pyrazolo[1,5-b]pyridazin-3-yl]-N-[3-(trifluoromethyl)phenyl]pyrimidin-2-amine;
N-(3,4-difluorophenyl)-4-[2-(4-methoxyphenyl)pyrazolo[1,5-b]pyridazin-3-yl]pyrimidin-2-amine;
N-(2,3-dihydro-1,4-benzodioxin-6-yl)-4-[2-(4-methoxyphenyl)pyrazolo[1,5-b]pyridazin-3-yl]pyrimidin-2-amine;
N-[4-chloro-3-(trifluoromethyl)phenyl]-4-[2-(4-methoxyphenyl)pyrazolo[1,5-b]pyridazin-3-yl]pyrimidin-2-amine;
N-phenyl-4-{2-[4-(trifluoromethyl)phenyl]pyrazolo[1,5-b]pyridazin-3-yl}pyrimidin-2-amine;
N-[3-(trifluoromethyl)phenyl]-4-{2-[4-(trifluoromethyl)phenyl]pyrazolo[1,5-b]pyridazin-3-yl}pyrimidin-2-amine;
N-(3,4-difluorophenyl)-4-{2-[4-(trifluoromethyl)phenyl]pyrazolo[1,5-b]pyridazin-3-yl}pyrimidin-2-amine;
N-(2,3-dihydro-1,4-benzodioxin-6-yl)-4-{2-[4-(trifluoromethyl)phenyl]pyrazolo[1,5-b]pyridazin-3-yl}pyrimidin-2-amine;
N-[4-chloro-3-(trifluoromethyl)phenyl]4-{2-[4-(trifluoromethyl)phenyl]pyrazolo[1,5-b]pyridazin-3-yl}pyrimidin-2-amine;
4-[2-(4-chlorophenyl)pyrazolo[1,5-b]pyridazin-3-yl]-N-phenylpyrimidin-2-amine;
4-[2-(4-chlorophenyl)pyrazolo[1,5-b]pyridazin-3-yl]-N-[3-(trifluoromethyl)phenyl]pyrimidin-2-amine;
4-[2-(4-chlorophenyl)pyrazolo[1,5-b]pyridazin-3-yl]-N-(3,4-difluorophenyl)pyrimidin-2-amine;
4-[2-(4-chlorophenyl)pyrazolo[1,5-b]pyridazin-3-yl]-N-(2,3-dihydro-1,4-benzodioxin-6-yl)pyrimidin-2-amine;
4-[2-(4-chlorophenyl)pyrazolo[1,5-b]pyridazin-3-yl]-N-[4-chloro-3-(trifluoromethyl)phenyl]pyrimidin-2-amine;
4-{6-methyl-2-[4-(trifluoromethyl)phenyl]pyrazolo[1,5-b]pyridazin-3-yl}-N-phenylpyrimidin-2-amine;
N-(2,3-dihydro-1,4-benzodioxin-6-yl)-4-[6-methyl-2-(4-methylphenyl)pyrazolo[1,5-b]pyridazin-3-yl]pyrimidin-2-amine;
N-[3,5-bis(trifluoromethyl)phenyl]-4-pyrazolo[1,5-b]pyridazin-3-yl-2-pyrimidinamine;

N-(3,5-dimethoxyphenyl)-4-pyrazolo[1,5-b]pyridazin-3-yl-2-pyrimidinamine;
N-(4-sec-butylphenyl)-4-pyrazolo[1,5-b]pyridazin-3-yl-2-pyrimidinamine;
N-(4-tert-butylphenyl)-4-pyrazolo[1,5-b]pyridazin-3-yl-2-pyrimidinamine;
N-(3,5-dichlorophenyl)-4-pyrazolo[1,5-b]pyridazin-3-yl-2-pyrimidinamine;
N-(3,4-dichlorophenyl)-4-pyrazolo[1,5-b]pyridazin-3-yl-2-pyrimidinamine;
N-(3,5-difluorophenyl)-4-pyrazolo[1,5-b]pyridazin-3-yl-2-pyrimidinamine;
N-[3-bromo-5-(trifluoromethyl)phenyl]-4-pyrazolo[1,5-b]pyridazin-3-yl-2-pyrimidinamine;
N-(3,4-dihydro-2H-1,5-benzodioxepin-7-yl)-4-pyrazolo[1,5-b]pyridazin-3-yl-2-pyrimidinamine;
3-[(4-pyrazolo[1,5-b]pyridazin-3-yl-2-pyrimidinyl)amino]-5-(trifluoromethyl)benzamide;
N-(3,4-difluorophenyl)-4-pyrazolo[1,5-b]pyridazin-3-yl-2-pyrimidinamine;
N-[4-chloro-3-(trifluoromethyl)phenyl]-4-pyrazolo[1,5-b]pyridazin-3-yl-2-pyrimidinamine;
N-phenyl-4-(2-phenylpyrazolo[1,5-b]pyridazin-3-yl)-2-pyrimidinamine;
4-(2-phenylpyrazolo[1,5-b]pyridazin-3-yl)-N-[3-(trifluoromethyl)phenyl]-2-pyrimidinamine;
N-[4-chloro-3-(trifluoromethyl)phenyl]-4-(2-phenylpyrazolo[1,5-b]pyridazin-3-yl)-2-pyrimidinamine;
N-(2,3-dihydro-1,4-benzodioxin-6-yl)-4-(2-phenylpyrazolo[1,5-b]pyridazin-3-yl)-2-pyrimidinamine;
N-(3,5-difluorophenyl)-4-(2-phenylpyrazolo[1,5-b]pyridazin-3-yl)-2-pyrimidinamine;
N-(3,4-difluorophenyl)-4-(2-phenylpyrazolo[1,5-b]pyridazin-3-yl)-2-pyrimidinamine;
4-[2-(4-fluorophenyl)pyrazolo[1,5-b]pyridazin-3-yl]-N-phenyl-2-pyrimidinamine;
N-(2,3-dihydro-1,4-benzodioxin-6-yl)-4-[2-(4-fluorophenyl)pyrazolo[1,5-b]pyridazin-3-yl]-2-pyrimidinamine;
4-[2-(4-fluorophenyl)pyrazolo[1,5-b]pyridazin-3-yl]-N-[3-(trifluoromethyl)phenyl]-2-pyrimidinamine;
N-[4-chloro-3-(trifluoromethyl)phenyl]-4-[2-(4-fluorophenyl)pyrazolo[1,5-b]pyridazin-3-yl]-2-pyrimidinamine;
N-(3,4-difluorophenyl)-4-[2-(4-fluorophenyl)pyrazolo[1,5-b]pyridazin-3-yl]-2-pyrimidinamine;
N-phenyl-4-{2-[3-(trifluoromethyl)phenyl]pyrazolo[1,5-b]pyridazin-3-yl}-2-pyrimidinamine;
N-(2,3-dihydro-1,4-benzodioxin-6-yl)-4-{2-[3-(trifluoromethyl)phenyl]pyrazolo[1,5-b]pyridazin-3-yl}-2-pyrimidinamine;
N-[3-(trifluoromethyl)phenyl]-4-{2-[3-(trifluoromethyl)phenyl]pyrazolo[1,5-b]pyridazin-3-yl}-2-pyrimidinamine;
N-[4-chloro-3-(trifluoromethyl)phenyl]-4-{2-[3-(trifluoromethyl)phenyl]pyrazolo[1,5-b]pyridazin-3-yl}2-pyrimidinamine;
N-(3,4-difluorophenyl)-4-{2-[3-(trifluoromethyl)phenyl]pyrazolo[1,5-b]pyridazin-3-yl}-2-pyrimidinamine;
4-(6-methyl-2-phenylpyrazolo[1,5-b]pyridazin-3-yl)-N-phenyl-2-pyrimidinamine;
N-(2,3-dihydro-1,4-benzodioxin-6-yl)-4-(6-methyl-2-phenylpyrazolo[1,5-b]pyridazin-3-yl)-2-pyrimidinamine;
4-(6-methyl-2-phenylpyrazolo[1,5-b]pyridazin-3-yl)-N-[3-(trifluoromethyl)phenyl]-2-pyrimidinamine;
N-[4-chloro-3-(trifluoromethyl)phenyl]-4-(6-methyl-2-phenylpyrazolo[1,5-b]pyridazin-3-yl)-2-pyrimidinamine;
N-(3,4-difluorophenyl)-4-(6-methyl-2-phenylpyrazolo[1,5-b]pyridazin-3-yl)-2-pyrimidinamine;
4-{6-methyl-2-[3-(trifluoromethyl)phenyl]pyrazolo[1,5-b]pyridazin-3-yl}N-phenyl-2-pyrimidinamine;
4-{6-methyl-2-[3-(trifluoromethyl)phenyl]pyrazolo[1,5-b]pyridazin-3-yl}N-[3-(trifluoromethyl)phenyl]-2-pyrimidinamine;
N-[4-chloro-3-(trifluoromethyl)phenyl]-4-{6-methyl-2-[3-(trifluoromethyl)phenyl]pyrazolo[1,5-b]pyridazin-3-yl}-2-pyrimidinamine;
N-(3,4-difluorophenyl)-4-{6-methyl-2-[3-(trifluoromethyl)phenyl]pyrazolo[1,5-b]pyridazin-3-yl}-2-pyrimidinamine;
N-(2,3-dihydro-1,4-benzodioxin-6-yl)-4-{6-methyl-2-[3-(trifluoromethyl)phenyl]pyrazolo[1,5-b]pyridazin-3-yl}-2-pyrimidinamine;
4-[2-(4-fluorophenyl)-6-methylpyrazolo[1,5-b]pyridazin-3-yl]-N-phenyl-2-pyrimidinamine;
N-(2,3-dihydro-1,4-benzodioxin-6-yl)-4-[2-(4-fluorophenyl)-6-methylpyrazolo[1,5-b]pyridazin-3-yl]-2-pyrimidinamine;
4-[2-(4-fluorophenyl)-6-methylpyrazolo[1,5-b]pyridazin-3-yl]-N-[3-(trifluoromethyl)phenyl]-2-pyrimidinamine;
N-[4-chloro-3-(trifluoromethyl)phenyl]-4-[2-(4-fluorophenyl)-6-methylpyrazolo[1,5-b]pyridazin-3-yl]-2-pyrimidinamine;
N-(3,4-difluorophenyl)-4-[2-(4-fluorophenyl)-6-methylpyrazolo[1,5-b]pyridazin-3-yl]-2-pyrimidinamine;
4-(2-cyclopropylpyrazolo[1,5-b]pyridazin-3-yl)-N-phenylpyrimidin-2-amine;
4-(2-cyclopropylpyrazolo[1,5-b]pyridazin-3-yl)-N-(3,4-difluorophenyl)pyrimidin-2-amine;
4-(2-cyclohexylpyrazolo[1,5-b]pyridazin-3-yl)-N-phenylpyrimidin-2-amine;
4-(2-cyclohexylpyrazolo[1,5-b]pyridazin-3-yl)-N-(3,4-difluorophenyl)pyrimidin-2-amine; or
a salt, solvate, or physiologically functional derivative thereof.

Another aspect of the present invention includes pharmaceutical compositions that include a therapeutically effective amount of the novel compounds as herein described, or a salt, solvate, or a physiologically functional derivative thereof and one or more of pharmaceutically acceptable carriers, diluents and excipients. Preferably the composition further includes at least one additional agent for the treatment or prophylaxis of diabetes.

Another aspect of the present invention includes a pharmaceutical composition that includes a therapeutically effective amount of a compound as herein described, or a salt, solvate, or a physiologically functional derivative thereof, and one or more of pharmaceutically acceptable carriers, diluents and excipients for preventing or treating conditions mediated by GSK-3.

Another aspect of the present invention includes a method of treating a disorder in a mammal, said disorder being mediated by inappropriate GSK-3 activity through the administration to said mammal of a therapeutically effective amount of a compound as described herein, or a salt, solvate, or a physiologically functional, derivative thereof. Preferably the disorder is Type II Diabetes.

Another aspect of the present invention includes a novel compound as herein described, or a salt, solvate, or a physiologically functional derivative thereof for use in therapy.

Another aspect of the present invention includes the use of a compound as herein described, or a salt, solvate, or a physiologically functional derivative thereof in the preparation of a medicament for use in the treatment of a disorder mediated by inappropriate GSK-3 activity. Preferably the disorder is Type II Diabetes.

Another aspect of the present invention includes a method of treating diabetes in a mammal, including administering to said mammal a therapeutically effective amount of a novel compound as herein described, or salt, solvate or physiologically functional derivative thereof.

Another aspect of the present invention in includes a method of treating diabetes in a mammal, including administering to said mammal therapeutically effective amounts of (i) a compound as herein described, or salt, solvate or physiologically functional derivative thereof and (ii) at least one additional anti-diabetic therapy.

DETAILED DESCRIPTION OF THE PREFERRED EMBODIMENT

As used herein, the term "lower" refers to a group having between one and six carbons. Similarly, preferred groups may also be referred to by a representation of the number of carbon atoms such as "$C_x$-$C_y$."

As used herein, the term "alkyl" refers to a straight or branched chain hydrocarbon, having from one to twelve carbon atoms, optionally substituted with one or more substituent selected from lower alkyl, lower haloalkyl, lower alkoxy, lower alkylthio, lower alkylsulfinyl, lower alkylsulfonyl, oxo, mercapto, amino optionally substituted by alkyl, carboxy, carbamoyl optionally substituted by alkyl, aminosulfonyl optionally substituted by alkyl, nitro, or lower perfluoroalkyl, multiple degrees of substitution being allowed. Examples of "alkyl" as used herein include, but are not limited to, methyl, ethyl, propyl, n-butyl, n-pentyl, isobutyl, and isopropyl, and the like. As used herein, the term "$C_1$-$C_6$ alkyl" refers to an alkyl group, as defined above, which contains at least 1 and at most 6 carbon atoms.

As used herein, the term "alkylene" refers to a straight or branched chain divalent hydrocarbon radical, having from one to ten carbon atoms. Alkylene groups, as used herein, may optionally be substituted with one or more substituent selected from lower alkyl, lower alkoxy, lower alkylthio, lower alkylsulfinyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and lower perfluoroalkyl, with multiple degrees of substitution being allowed. Examples of "alkylene" as used herein include, but are not limited to, methylene, ethylene, n-propylene, n-butylene, and the like. As used herein, the terms "$C_1$-$C_3$ alkylene" and "$C_1$-$C_4$ alkylene" refer to an alkylene group, as defined above, which contains at least 1, and at most 3 or 4, carbon atoms respectively.

As used herein, the term "alkenyl" refers to a hydrocarbon radical having from two to ten carbons and at least one carbon-carbon double bond, optionally substituted with one or more substituent selected from lower alkyl, lower alkoxy, lower alkylthio, lower alkylsulfinyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and lower perfluoroalkyl, multiple degrees of substitution being allowed. Examples of "alkenyl" as used herein include, ethenyl, propenyl, 1-butenyl, 2-butenyl, and isobutenyl. As used herein, the term "$C_1$-$C_6$ alkenyl" refers to an alkenyl group as defined above containing at least 1, and at most 6, carbon atoms.

As used herein, the term "alkenylene" refers to an straight or branched chain divalent hydrocarbon radical having from two to ten carbon atoms and one or more carbon-carbon double bonds, optionally substituted with one or more substituent selected from lower alkyl, lower alkoxy, lower alkylthio, lower alkylsulfinyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and lower perfluoroalkyl, multiple degrees of substitution being allowed. Examples of "alkenylene" as used herein include, but are not limited to, ethene-1,2-diyl, propene-1,3-diyl, methylene-1,1-diyl, and the like. As used herein, the term "$C_1$-$C_3$ alkenylene" refers to an alkenylene group as defined above containing at least 1, and at most 3, carbon atoms.

As used herein, the term "alkynyl" refers to a hydrocarbon radical having from two to ten carbons and at least one carbon-carbon triple bond, optionally substituted with one or more substituent selected from lower alkyl, lower alkoxy, lower alkylthio, lower alkylsulfinyl, lower alkylsulfonyl, oxo, aryl, hydroxy, mercapto, amino optionally substituted by alkyl, carboxy, carbamoyl optionally substituted by alkyl, aminosulfonyl optionally substituted by alkyl, nitro, cyano, halogen and lower perfluoroalkyl, with multiple degrees of substitution being allowed. Examples of "alkynyl" as used herein, include but are not limited to acetylenyl, 1-propynyl, 1-butynyl, 2-butynyl, 1-pentynyl, and 1-hexynyl.

As used herein, the term "alkynylene" refers to a straight or branched chain divalent hydrocarbon radical having from two to ten carbon atoms and one or more carbon-carbon triple bond, optionally substituted with one or more substituent selected from lower alkyl, lower alkoxy, lower alkylthio, lower alkylsulfinyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and lower perfluoroalkyl, with multiple degrees of substitution being allowed. Examples of "alkynylene" as used herein include, but are not limited to, ethyne-1,2-diyl, propyne-1,3-diyl, and the like. As used herein, the term $C_1$-$C_6$ alkynylene, "$C_1$-$C_3$ alkenylene" refers to an alkenylene group as defined above containing at least 1, and at most 3, carbon atoms.

As used herein, the term "halogen" or "halo" refers to fluoro (—F), chloro (—Cl), bromo (—Br), or iodo (—I).

As used herein, the term "$C_1$-$C_6$ haloalkyl" refers to a straight or branched chain hydrocarbon containing at least 1, and at most 6, carbon atoms substituted with at least one halogen, where halogen above is defined. Examples of branched or straight chained "$C_1$-$C_6$ haloalkyl" groups useful in the present invention include, but are not limited to, methyl, ethyl, propyl, isopropyl, isobutyl and n-butyl substituted independently with one or more halogens, e.g., fluoro, chloro, bromo and iodo. Further examples include groups such as perfluoroalkyl, for example, trifluoromethyl (—$CF_3$).

As used herein, the term "$C_3$-$C_7$ cycloalkyl" refers to a non-aromatic cyclic hydrocarbon ring having from three to seven carbon atoms, which optionally includes a $C_1$-$C_4$ alkylene linker through which it may be attached. As used herein "cycloalkyl" groups may optionally be substituted with one or more substituent selected from lower alkyl lower alkoxy, lower alkylthio, lower alkylsulfinyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, and lower perfluoroalkyl, with multiple degrees of substitution being allowed. Exemplary "$C_3$-$C_7$ cycloalkyl" groups include, but are not limited to, cyclopropyl, cyclobutyl, cyclopentyl, cyclohexyl and cycloheptyl.

As used herein, the term "$C_3$-$C_7$ cycloalkylene" refers to a non-aromatic alicyclic divalent hydrocarbon radical having from three to seven carbon atoms, optionally substituted with one or more substituent selected from lower alkyl, lower alkoxy, lower alkylthio, lower alkylsulfinyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "$C_3$-$C_7$ cycloalkenyl" refers to a non-aromatic cyclic hydrocarbon ring having from three to seven carbon atoms, and one or more carbon-carbon double bonds, which optionally includes a $C_1$-$C_4$ alkylene linker through which it may be attached, and which may optionally be substituted with one or more substituent selected from lower alkyl, lower alkoxy, lower alkylthio, lower alkylsulfinyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Exemplary "$C_3$-$C_7$ cycloalkenyl" groups include, but are not limited to, cyclobutenyl, cyclopentenyl, cyclohexenyl and cycloheptenyl.

As used herein, the term "$C_3$-$C_7$ cycloalkenylene" refers to a non-aromatic alicyclic divalent hydrocarbon radical having from three to seven carbon atoms, and one or more carbon-carbon double bonds optionally substituted with one or more substituent selected from the group which includes lower alkyl, lower alkoxy, lower alkylthio, lower alkylsulfinyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, lower perfluoroalkyl, multiple degrees of substitution being allowed. Examples of "cycloalkenylene" as used herein include, but are not limited to, 4,5-cyclopentene-1,3-diyl, 3,4-cyclohexene-1,1-diyl, and the like.

As used herein, the term "heterocyclic" or the term "heterocyclyl" refers to a three to twelve-membered heterocyclic, non-aromatic, ring, which is unsaturated or has one or more degrees of unsaturation, which contains one or more heteroatomic substitutions selected from S, SO, $SO_2$, O, or N, optionally substituted with one or more substituent selected from lower alkyl, lower alkoxy, lower alkylthio, lower alkylsulfinyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused with one or more of another "heterocyclic" ring(s) or cycloalkyl ring(s). Examples of "heterocyclic" groups include, but are not limited to, tetrahydrofuran, pyran, 1,4-dioxane, 1,3-dioxane, piperidine, pyrrolidine, morpholine, tetrahydrothiopyran, tetrahydrothiophene, and the like.

As used herein, the term "aryl" refers to an optionally substituted benzene ring or to an optionally substituted benzene ring system fused to one or more optionally substituted benzene rings to form, for example, anthracene, phenanthrene, or napthalene ring systems. Exemplary optional substituents include lower alkyl, lower alkoxy, lower alkylthio, lower alkylsulfinyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heterocyclyl, heteroaryl, or aryl, with multiple degrees of substitution being allowed. Examples of "aryl" groups include, but are not limited to, phenyl, 2-naphthyl, 1-naphthyl, biphenyl, as well as substituted derivatives thereof.

As used herein, the term "arylene" refers to a di-radical benzene ring or to a di-radical benzene ring system fused to one or more optionally substituted benzene rings, either optionally substituted with one or more substituent selected from $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, $C_1$-$C_6$ perfluoroalkyl, heteroaryl and aryl, with multiple degrees of substitution being allowed. Examples of "arylene" include, but are not limited to, benzene-1,4-diyl, naphthalene-1,8-diyl, anthracene-1,4-diyl, and the like.

As used herein, the term "aralkyl" refers to an aryl or heteroaryl group, as defined herein, attached through a lower alkylene linker, wherein lower alkylene is as defined herein. Examples of "aralkyl" include, but are not limited to, benzyl, phenylpropyl, 2-pyridylmethyl, 3-isoxazolylmethyl, 5-methyl-3-isoxazolylmethyl, and 2-imidazoyl ethyl.

As used herein, the term "heteroaryl" refers to a monocyclic five to seven membered aromatic ring, or to a fused bicyclic aromatic ring system comprising two of such monocyclic five to seven membered aromatic rings. These heteroaryl rings contain one or more nitrogen, sulfur, and/or oxygen heteroatoms, where N-oxides and sulfur oxides and dioxides are permissible heteroatom substitutions and may be optionally substituted one ore more times with lower alkyl, lower alkoxy, lower alkylthio, lower alkylsulfinyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, with multiple degrees of substitution being allowed. Examples of "heteroaryl" groups used herein include furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, indazole, and substituted versions thereof.

As used herein, the term "heteroarylene" refers to a di-radical five- to seven-membered aromatic ring radical, or to a di-radical polycyclic heterocyclic aromatic ring, containing one or more nitrogen, oxygen, or sulfur heteroatoms, where N-oxides and sulfur monoxides and sulfur dioxides are permissible heteroaromatic substitutions, optionally substituted one or more times with substituents selected from lower alkyl, lower alkoxy, lower alkylthio, lower alkylsulfinyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, with multiple degrees of substitution being allowed. For polycyclic aromatic ring system di-radicals, one or more of the rings may contain one or more heteroatoms. Examples of "heteroarylene" groups as used herein include furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term. "alkoxy" refers to the group —$OR_a$, where $R_a$ is alkyl as defined above and the term "$C_1$-$C_6$ alkoxy" refers to the group —$OR_a$, where $R_a$ is $C_1$-$C_6$ alkyl as defined above.

As used herein the term "aralkoxy" refers to the group —$OR_aR_b$, where $R_a$ is alkylene and $R_b$ is aryl, both as defined above.

As used herein, the term "alkylthio" refers to the group —$SR_a$, where $R_a$ is alkyl as defined above.

As used herein, the term "alkylsulfinyl" refers to the group —$S(O)R_a$, where $R_a$ is alkyl as defined above.

As used herein, the term "alkylsulfonyl" refers to the group —$S(O)_2R_a$, where $R_a$ is alkyl as defined above.

As used herein, the term "oxo" refers to the group =O.

As used herein, the term "mercapto" refers to the group —SH.

As used herein, the term "carboxy" refers to the group —COOH.

As used herein, the term "cyano" refers to the group —CN.

As used herein the term "cyanoalkyl" refers to the group —$R_a$CN wherein $R_a$ is $C_1$-$C_3$ alkylene as defined above. Exemplary "cyanoalkyl" groups useful in the present invention include, but are not limited to, cyanomethyl, cyanoethyl, and cyanopropyl.

As used herein, the term "aminosulfonyl" refers to the group —$SO_2NH_2$.

As used herein, the term "carbamoyl" refers to the group —C(O)$NH_2$.

As used herein, the term "thio" shall refer to the group —S—.

As used herein, the term "sulfinyl" shall refer to the group —S(O)—.

As used herein, the term "sulfonyl" shall refer to the group —$S(O)_2$— or —$SO_2$—.

As used herein, the term "acyl" refers to the group —C(O)$R_a$, where $R_a$ is alkyl, cycloalkyl, or heterocyclyl as defined herein.

As used herein, the term "aroyl" refers to the group —C(O)$R_a$, where $R_a$ is aryl as defined herein.

As used herein, the term "heteroaroyl" refers to the group —C(O)$R_a$, where $R_a$ is heteroaryl as defined herein.

As used herein, the term "alkoxycarbonyl" refers to the group —C(O)$OR_a$, where $R_a$ is alkyl as defined herein.

As used herein, the term "acyloxy" refers to the group —OC(O)$R_a$, where $R_a$ is alkyl, cycloalkyl, or heterocyclyl as defined herein.

As used herein, the term "aroyloxy" refers to the group —OC(O)$R_a$, where $R_a$ is aryl as defined herein.

As used herein, the term "heteroaroyloxy" refers to the group —OC(O)$R_a$, where $R_a$ is heteroaryl as defined herein.

As noted above, the present invention includes salts, solvates, and pharmaceutically functional derivatives of the compounds of the present invention. Salts of the present invention include addition salts, metal salts, or optionally alkylated ammonium salts. Examples of such salts include hydrochloric, hydrobromic, hydroiodic, phosphoric, sulfuric, trifluoroacetic, trichloroacetic, oxalic, maleic, pyruvic, malonic, succinic, citric, mandelic, benzoic, cinnamic, methane sulphonic, ethane sulphonic, picric, and the like. Further salts include lithium, sodium, potassium, magnesium, and the like. Reference is also made to Journal of Pharmaceutical Science, 1997, 66, 2, incorporated herein by reference, as relevant to salts.

Typically, the salts of the present invention are pharmaceutically acceptable salts. Salts encompassed within the term "pharmaceutically acceptable salts" refer to non-toxic salts of the compounds of this invention. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, which are not pharmaceutically acceptable, may be useful in the preparation of compounds of this invention and these salts form a further aspect of the invention.

As used herein, the term "solvate" refers to a complex of variable stoichiometry formed by a solute of the present invention and a solvent. Such solvents for the purpose of the invention should not interfere with the biological activity of the solute. Examples of suitable solvents include, but are not limited to, water, methanol, ethanol, and acetic acid. Preferably, the solvent used is a pharmaceutically acceptable solvent. Examples of suitable pharmaceutically acceptable solvents include water, ethanol, and acetic acid. Most preferably, the solvent used is water.

As used herein, the term "physiologically functional derivative" refers to any pharmaceutically acceptable derivative of a compound of the present invention that, upon administration to a mammal, is capable of providing, either directly or indirectly, a compound of the present invention or an active metabolite thereof. Such derivatives, for example, an ester or an amide of the present invention, are clear to those skilled in the art, without undue experimentation. Reference is made to the teaching of Burger's Medicinal Chemistry and Drug Discovery, $5^{th}$ Edition, Vol 1: Principles and Practice, which is incorporated herein by reference to the extent of teaching physiologically functional derivatives.

As used herein, the term "effective amount" means that amount of a drug or pharmaceutical agent that will elicit the biological or medical response of a tissue, system, animal or human that is being sought, for instance, by a researcher or clinician.

Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The compounds of the present invention have the ability to crystallize in more than one form, a characteristic that is known as polymorphism, and such polymorphic forms ("polymorphs") are within the scope of the present invention. Polymorphism generally can occur as a response to changes in temperature, pressure, or both and can also result from variations in the crystallization process. Polymorphic forms can be distinguished by various physical characteristics that are known in the art, such as x-ray diffraction patterns, solubility, and melting point.

Certain of the compounds described herein may contain one or more chiral atoms, or may otherwise be capable of existing as two enantiomers. Accordingly, the compounds of this invention may include mixtures of enantiomers, purified enantiomers, or enantiomerically enriched mixtures. Also included within the scope of the invention are the individual isomers of the compounds of the present invention, as well as any wholly or partially equilibrated mixtures thereof. The present invention also includes the individual isomers of the compounds represented by the formulas above as mixtures with isomers thereof in which one or more chiral centers are inverted.

While, for use in therapy, therapeutically effective amounts of a compound of the present invention may be administered as the raw chemical, the active ingredient also may be prepared as a pharmaceutical formulation. Accordingly, the invention further provides pharmaceutical formulations that include effective and therapeutically effective amounts of compounds of the present invention along with one or more pharmaceutically acceptable carriers, diluents, or excipients. The carrier(s), diluent(s) or excipient(s) should be acceptable in the sense of being compatible with the other ingredients of the formulation and not deleterious to the recipient of the formulation. In accordance with an aspect of the invention, there is provided a process for the preparation of pharmaceutical formulations that includes mixing a compound of the present invention with one or more pharmaceutically acceptable carriers, diluents or excipients.

Pharmaceutical formulations may be presented in unit dose forms containing a predetermined amount of active ingredient per unit dose. Such a unit contains an amount of compound of the present invention, for example, 0.5 mg to 1 g of a compound of the present invention, depending on the condition being treated, the route of administration, and the age, weight, and condition of the recipient. Preferred unit dosage formulations are those containing a daily dose or sub-dose, or an appropriate fraction thereof, of the active ingredient. Such pharmaceutical formulations may be prepared by any of the methods well known in the pharmacy art.

Pharmaceutical formulations may be adapted for administration by any appropriate route, for example by oral (including buccal or sublingual), rectal, nasal, topical (including buccal, sublingual, or transdermal), vaginal, or parenteral (including subcutaneous, intramuscular, intravenous, or intradermal) routes. Such formulations may be prepared by any method known in the art of pharmacy, for example by bringing into association the active ingredient with the carrier(s), diluent(s), or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water, or mixtures thereof. Powders are prepared by comminuting the compound to a suitable fine size and mixing the comminuted compound with a similarly comminuted pharmaceutical carrier such as an edible carbohydrate, for example, starch or mannitol. Flavorings, preservatives, dispersing and/or coloring agents can also be present.

Capsules may be prepared by preparing a powder mixture as described above, and filling formed gelatin sheaths with the powder. Glidants and lubricants such as colloidal silica, talc, magnesium stearate, calcium stearate, or polyethylene glycol can be added to the powder mixture before the filling operation. A disintegrating or solubilizing agent such as agar-agar calcium carbonate, or sodium carbonate can also be added to improve the availability of the medicament when the capsule is ingested. Moreover, when desired or necessary, suitable binders, lubricants, disintegrating agents, and coloring agents can also be incorporated into such mixtures. Suitable binders include starch, gelatin, natural sugars such as glucose or beta-lactose, corn sweeteners, natural and synthetic gums, such as acacia, tragacanth or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrating agents include, without limitation, starch, methyl cellulose, agar, bentonite, xanthan gum, and the like.

Tablets may be prepared, for example, by preparing a powder mixture of the present invention, potentially through granulating or slugging, adding a lubricant, a disintegrant, and then pressing the mixture into tablets. A powder mixture is prepared as described above. Optionally, a binder may be added, such as carboxymethylcellulose, an aliginate, gelatin, or polyvinyl pyrrolidone, a solution retardant may be added, such as paraffin, a resorption accelerator may be added, such as a quaternary salt and/or an absorption agent may be added, such as bentonite, kaolin, or dicalcium phosphate. The powder mixture can be wet-granulated with a binder such as syrup, starch paste, acadia mucilage, or solutions of cellulosic or polymeric materials and then forced through an appropriate screen. As an alternative to granulating, the powder mixture can be run through the tablet machine, resulting in imperfectly formed slugs that are broken into granules. The granules can be lubricated to prevent sticking to the tablet forming dies by means of the addition of stearic acid, a stearate salt, talc, or mineral oil. The lubricated mixture is then compressed into tablets. The compounds of the present invention can also be combined with a free flowing inert carrier and compressed into tablets directly without going through either granulating or slugging steps. A clear or opaque protective coating consisting of a sealing coat of shellac, a coating of sugar, or a coating of polymeric material, and a polish coating of wax can be provided. Dyestuffs can be added to these coatings as well.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxyethylene sorbitol ethers, preservatives, flavor additives such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of the present invention may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986), incorporated herein by reference to such extent.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated as an ointment, the active ingredient may be employed with either a paraffinic or water-miscible ointment base. Alternatively, the active ingredient may be formulated in a cream with an oil-in-water base or a water-in-oil base.

Pharmaceutical formulations adapted for topical administrations to the eye include eye drops wherein the active ingredient is dissolved or suspended in a suitable carrier, especially an aqueous solvent. Pharmaceutical formulations adapted for topical administration in the mouth include lozenges, pastilles, and mouthwashes. Pharmaceutical formulations adapted for rectal administration may be presented as suppositories or as enemas. Pharmaceutical formulations adapted for nasal administration, where the carrier is a solid, include a coarse powder, having a particle size for example in the range 20 to 500 microns, which is administered by rapid inhalation through the nasal passages from a container of the powder that is held close to the nose. Suitable formulations, wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose-pressurized aerosols, nebulizers, or insufflators. Pharmaceutical formulations adapted for vaginal administration may be presented as pessaries, tampons, creams, gels, pastes, foams, or spray formulations. Pharmaceutical formulations adapted for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and/or thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

In addition to the ingredients particularly mentioned above, the formulations may include other agents conventional in the art having regard to the type of formulation in question, for example those suitable for oral administration may include flavoring agents.

As mentioned briefly above, a therapeutically effective amount of a compound of the present invention will depend upon a number of factors including, for example, age, weight, the precise condition to be treated and its severity, the nature of the formulation, and the route of administration. The determination of the therapeutically effective amount ultimately is at the discretion of an attendant physician or veterinarian. Nevertheless, an effective amount of a compound of the present invention for the treatment of a GSK-3 mediated disorder, for example type II diabetes, generally will be in the range of about 0.1 to 100 mg/kg body weight of the recipient (mammal) per day. More usually the range will be between about 1 to 10 mg/kg body weight per day. For example, for a 70 kg adult mammal the actual amount per day would usually be from 70 to 700 mg. This amount may be given in a single dose per day or more usually in a number (such as two, three, four, five or six) of sub-doses per day such that the total daily dose is the same. An effective amount of a salt or solvate, or physiologically functional derivative thereof, may be determined as a proportion of the effective amount of the compound of formula (I) per se. No toxicological effects are indicated/expected when a compound of the present invention is administered in the above mentioned dosage range.

The compounds of the present invention may be employed alone or in combination with other therapeutic agents for the treatment of GSK-3 mediated conditions. In particular, in type II diabetes treatment, combinations of the compounds of the present invention with other anti-diabetic agents is envisaged. Combination therapies according to the present invention include the administration of at least one compound of the present invention or salt, solvate, or physiologically functional derivative thereof, and the use of at least one other diabetic treatment method. Preferably, combination therapies according to the present invention comprise the administration of at least one compound of the present invention and at least one other pharmaceutically active agent, such as insulin, α-glucosidase inhibitors, biguanides, insulin secretagogues, or insulin sensitizers. Non-limiting examples of α-glucosidase inhibitors include acarbose, emiglitate, miglitol, and voglibose. Non-limiting examples of biguanides include metformin, buformin, and phenformin. Non-limiting examples of insulin secretagogues include sulphonylureas. Non-limiting examples of insulin sensitizers include peroxisome proliferator activated receptor (PPAR) ligands, such as PPAR-γ agonists, for example Actos™ and Avandia™. The compound(s) of the present invention and other pharmaceutically active agent(s) may be administered together or separately. When administered separately the administration may occur simultaneously or sequentially in any order. The amounts of the compound(s) of the present invention and the other pharmaceutically active agent(s) and the relative timings of administration will be selected in order to achieve the desired combined therapeutic effect.

The compounds of the present invention and at least one additional diabetic treatment therapy may be employed in combination concomitantly or sequentially in any therapeutically appropriate combination with such other anti-diabetic therapies. The administration in combination of a compound of the present invention with other anti-diabetic agents may be in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one agent is administered first and the other second or vice versa. Such sequential administration may be close in time or remote in time.

The mammal requiring treatment with a compound of the present invention is typically a human being.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the working Examples.

Compounds of general formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as the reaction conditions and order of their execution shall be consistent with the preparation of compounds of Formula (I). Those skilled in the art will recognize if a stereocenter exists in compounds of Formula (I). Accordingly, the present invention includes both possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994).

For example, a general method (A) for preparing compounds of the general formula (I) involves the reaction of a compound of general formula (II) with a compound of general formula (III):

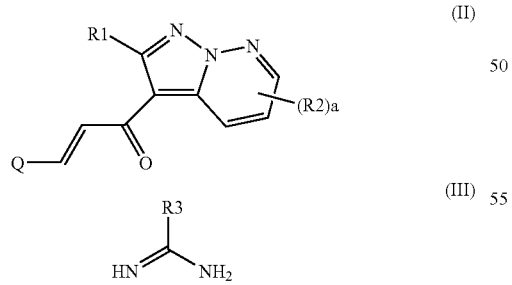

wherein Q is alkyloxy, alkylthio, or dialkylamino.

The general method (A) can be readily carried out by mixing a compound of general formula (II) with a compound of general formula (III) in a suitable solvent, optionally in the presence of a base, and heating the reaction mixture to about 50-150° C. Typically the solvent is a lower alcohol such as methanol, ethanol, isopropanol, and the like, and the base can be, for example, a sodium alkoxide, potassium carbonate, or an amine base such as triethylamine.

Compounds of general formula (II) may be conveniently prepared by reacting a compound of general formula (IV) with a dimethylformamide dialkylacetal, to give compounds of formula (II) wherein Q is Me$_2$N, or with a trialkyl orthoformate or a dialkoxymethyl acetate, to give compounds of formula (II) wherein Q is an alkoxy group. Conveniently, a dimethylformamide dialkylacetal is dimethylformamide dimethyl acetal or dimethylformamide di-tert-butyl acetal and the reaction carried out by mixing the compound of general formula (IV) with the dimethylformamide dialkylacetal and optionally heating the reaction. Preferred trialkyl orthoformates include trimethyl orthoformate and triethyl orthoformate. In a similar manner, diethoxymethyl acetate can be employed to prepare compounds of general formula (II) wherein Q is EtO—.

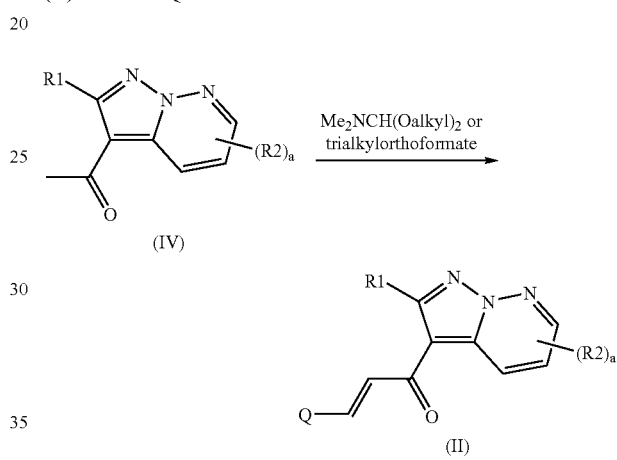

Compounds of general formula (IV) can be prepared from compounds of general formula (V) and general formula (VI) by a cycloaddition procedure. Typically the cycloaddition procedure is carried out by combining compounds of general formula (V) with compounds of general formula (VI) in a suitable solvent and treating the mixture with a base. Optionally the reaction can be heated. Preferably the solvent is dichloromethane, chloroform, acetonitrile, diethyl ether, and the like, and the base is an amine such as triethylamine, diisopropylethylamine or diazabicycloundecene (DBU). In another preferred method, compounds of general formula (V) and (VI) are combined in a mixture of solvents and treated with a base. Preferably the solvent mixtures are DMSO and water, or methanol and water, and the base is sodium hydroxide, or potassium hydroxide.

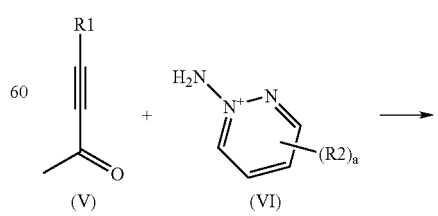

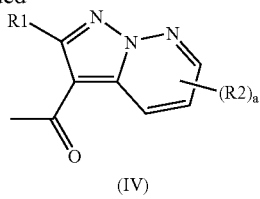

(IV)

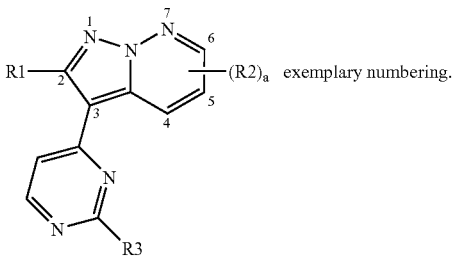

exemplary numbering.

Compounds of general formula (V) are known in the literature and can be prepared by oxidation of alcohols of general formula (VII) under conditions typically employed for the oxidation of propargylic alcohols.

This conversion can be carried out by treatment of a compound of general formula (X) with an acid or a base in a suitable solvent and optionally heating the mixture. Preferably the base is an amine such as morpholine. Preferably the acid is aqueous hydrogen iodide.

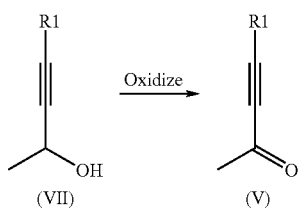

Alternatively, compounds of general formula (V) can be prepared by reaction of an ethyne of general formula (VIII) with a suitable base to form the ethynyl anion and treatment of the anion with dimethyl acetamide. Preferably the base is an alkyl lithium, such as n-butyl lithium, or a lithium dialkylamide, such as lithium diisopropylamide (LDA).

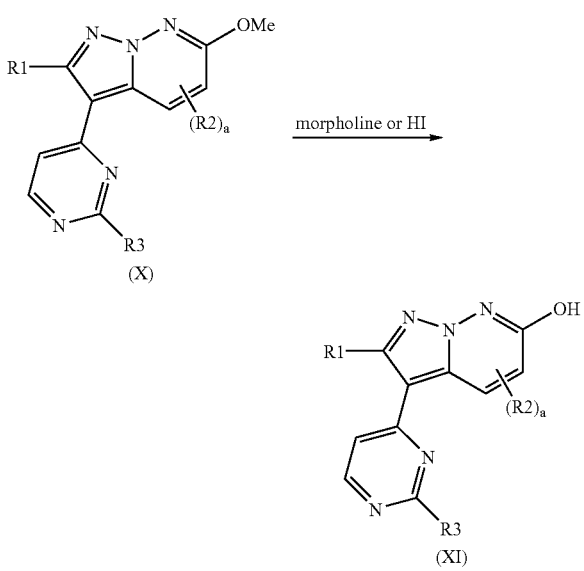

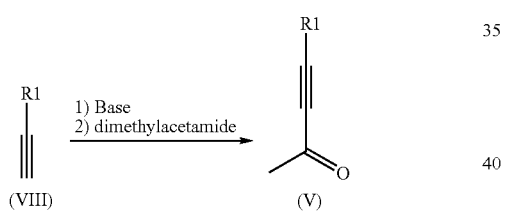

Compounds of general formula (VI) are N-aminopyridazines and are conveniently prepared by treatment of a pyridazine of general formula (IX) with an aminating reagent. Conveniently the aminating reagent is O-mesitylenesulfonylhydroxylamine (MSH) or hydroxylamine-O-sulfonic acid (HOSA). Preferably the aminating agent is hydroxylamine-o-sulfonic acid in water with the addition of a buffer to control the pH of the reaction medium.

The alcohol function in compounds of general formula (XI) can be further transformed by treatment with, for example, trifluoromethanesulfonic anhydride or N-phenyltrifluoromethylsulfonimide to afford a triflate. Triflates are known in the literature as leaving groups and can be readily displaced by treatment with an amine in a suitable solvent to give compounds of general formula (XII).

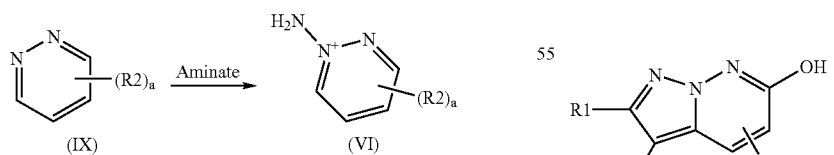

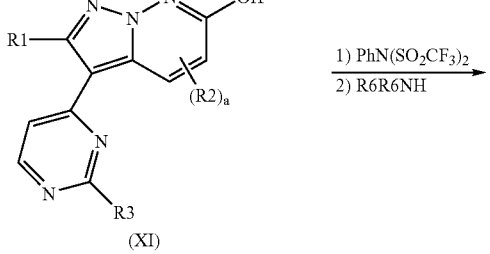

Compounds of general formula (I) can be converted to alternate compounds of general formula (I). For example, compounds of general formula (X), wherein an R2 group is a methoxy (—OMe) substituent and is located at position 6, using the numbering system described below, can be converted to compounds of general formula (X) wherein an R2 is a hydroxyl group at position 6:

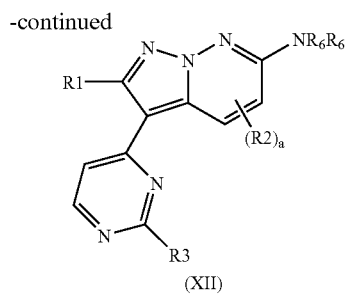

(XII)

Compounds of general formula (IV) can, similarly, be converted to alternate compounds of general formula (IV). Compounds of general formula (XIII) in which an R2 group is a methoxy substituent, and is located at position 6, can be converted to the corresponding hydroxy compound, of general formula (XIV), by treatment with an amine such as morpholine or ad acid such as aqueous hydrogen iodide. Said hydroxy derivatives of general formula (XIV) can be converted to triflates, of general formula (XV), by treatment with a trifluoromethanesulfonylating agent such as trifluoromethanesulfonic anhydride or N-phenyltrifluoromethanesulfonimide. Triflates of general formula (XV) can be converted to corresponding amino, thio, or ether derivatives by treatment with amines, thiols, or alcohols respectively, each optionally in the presence of a metal catalyst. Alternatively, triflates such as those of general formula (XV) can be reacted with a transition metal catalyst and a coupling partner to give compounds of general formula (XVI). Preferably the transition metal catalyst is a palladium or nickel complex. More preferably the catalyst is a palladium complex such as tetrakis(triphenylphosphine)-palladium(0). Coupling partners can be derivatives of tin, boron, zinc, aluminum, copper, magnesium, zirconium, and the like. Preferred coupling partners include triaklyltin derivatives or boron containing derivatives. Such reactions are well documented in the literature and are commonly referred to as Stille couplings and Suzuki couplings respectively. Under said conditions, triflates such as those of general formula (XV) can be converted to compounds of general formula (XVI) wherein the group A can represent an aryl, heteroaryl, ethenyl, ethynyl, and the like. One skilled in the art will appreciate that the aryl, heteroaryl, ethenyl, or ethynyl group can be suitably substituted.

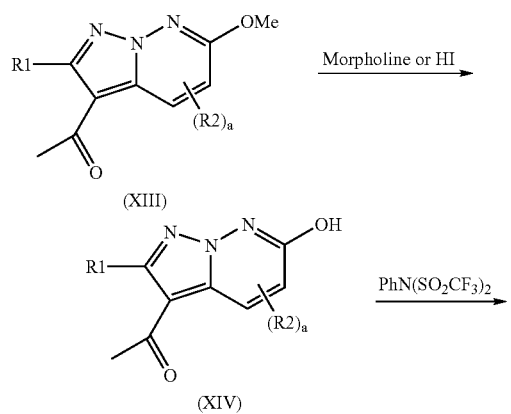

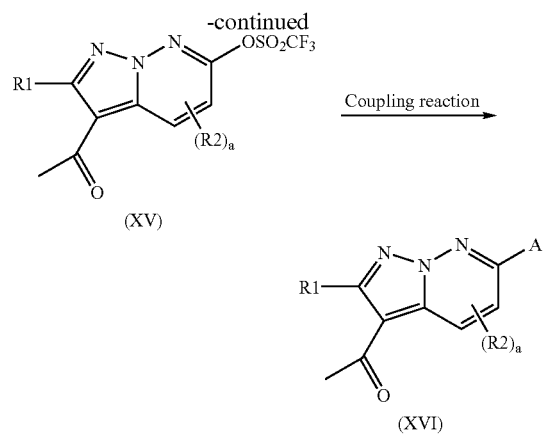

In an another method for the conversion of compounds of general formula (I) to alternative compounds of formula (I), compounds of general formula (XVII), wherein R3 is an alkylthio group, can be reacted with an amine in a suitable solvent and optionally heated to give compounds of general formula (XVIII). Preferred solvent for effecting the reaction include lower alcohols, such as methanol, ethanol and isopropanol. Even more preferably the reaction is heated to about 150 C in a sealed vessel.

A still more preferred method involves the oxidation of compounds of general formula (XVII) to the corresponding sulfoxide (XIX) or sulfone (XX), followed by reaction with an amine in a suitable solvent with optional heating. Preferred methods for effecting the said oxidation involve the use of reagents typically employed for the oxidation of sulfur compounds such as hydrogen peroxide or m-chloroperoxybenzoic acid in an inert solvent such as dichloromethane, acetonitrile and the like. Preferred solvent for effecting the reaction with an a mine include lower alcohols, such as methanol, ethanol and isopropanol. Even more preferably the reaction is heated to about 150 C in a sealed vessel.

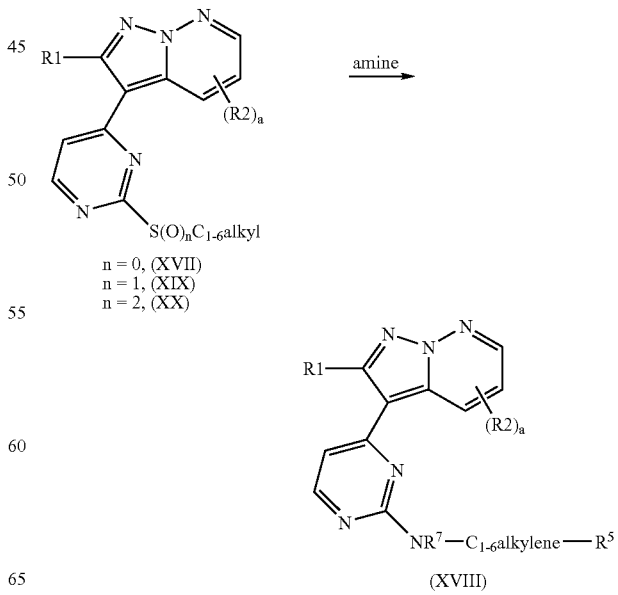

Compounds of general formula (XVII) can be conveniently prepared by treating a mixture of compounds of general formula (XXI) and compounds of general formula (VI) in a suitable solvent with a base and optionally heating the reaction mixture. Preferably the solvent is a halogenated solvent, such as dichloromethane, and the base is an amine, such as triethylamine, diazabicycloundecene (DBU) and the like, or an alkali metal hydroxide, such as sodium hydroxide or potassium hydroxide.

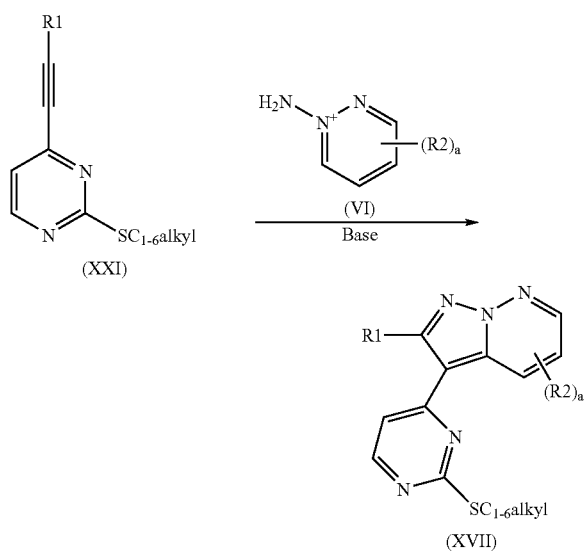

Compounds of general formula (XXI) can be conveniently prepared by treating a compound of general formula (XXII), wherein B is a halogen such as iodide, bromide or chloride, or a triflate, with an ethyne of general formula (VIII) in a suitable solvent in the presence of a palladium catalyst and optionally heating the reaction mixture. Preferably B is iodide and the palladium catalyst is tetrakis(triphenylphosphine)palladium(0), dichlorobis(triphenylphosphine)palladium(II), and the like. Preferred solvents include dichloromethane, tetrahydrofuran and the like. Compounds of general formula (XXII) are known in the literature.

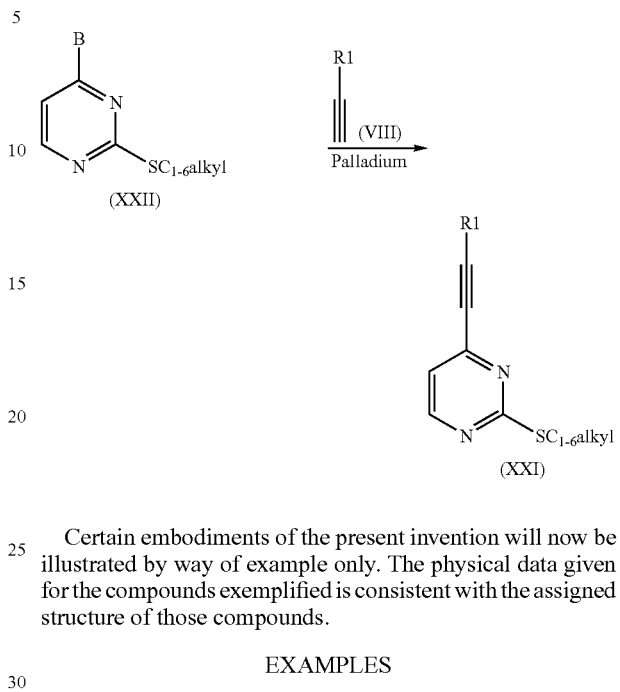

Certain embodiments of the present invention will now be illustrated by way of example only. The physical data given for the compounds exemplified is consistent with the assigned structure of those compounds.

EXAMPLES

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

| | |
|---|---|
| g (grams); | mg (milligrams); |
| L (liters); | mL (milliliters); |
| μL (microliters); | psi (pounds per square inch); |
| M (molar); | mM (millimolar); |
| i.v. (intravenous); | Hz (Hertz); |
| MHz (megahertz); | mol (moles); |
| mmol (millimoles); | RT (room temperature); |
| min (minutes); | h (hours); |
| mp (melting point); | TLC (thin layer chromatography); |
| $T_r$ (retention time); | RP (reverse phase); |
| MeOH (methanol); | I-PrOH (isopropanol); |
| TEA (triethylamine); | TFA (trifluoroacetic acid); |
| TFAA (trifluoroacetic anhydride); | THF (tetrahydrofuran); |
| DMSO (dimethylsulfoxide); | EtOAc (ethyl acetate); |
| DME (1,2-dimethoxyethane); | DCM (dichloromethane); |
| DCE (dichloroethane); | DMF (N,N-dimethylformamide); |
| DMPU (N,N'-dimethylpropyleneurea); | IBCF (isobutyl chloroformate); |
| CDI (1,1-carbonyldiimidazole); | HOSu (N-hydroxysuccinimide); |
| HOAc (acetic acid); | mCPBA (meta-chloroperbenzoic acid; |
| HOBT (1-hydroxybenzotriazole); | FMOC (9-fluorenylmethoxycarbonyl); |
| EDC (ethylcarbodiimide hydrochloride); | CBZ (benzyloxycarbonyl); |
| BOC (tert-butyloxycarbonyl); | atm (atmosphere); |
| DCC (dicyclohexylcarbodiimide); | TMS (trimethylsilyl); |
| Ac (acetyl); | TBS (t-butyldimethylsilyl); |
| TMSE (2-(trimethylsilyl)ethyl); | Me (methyl); |

-continued

TIPS (triisopropylsilyl); tBu (tert-butyl);
DMAP (4-dimethylaminopyridine);
HPLC (high pressure liquid chromatography);
BOP (bis(2-oxo-3-oxazolidinyl)phosphinic chloride);
TBAF (tetra-n-butylammonium fluoride);
Et (ethyl);
HOSA (hydroxylamine sulfonic acid);
DEAD (diethylazodicarboxylate);
DIEA (diisopropylethylamine).

All references to ether are to diethyl ether; brine refers to a saturated aqueous solution of NaCl. Unless otherwise indicated, all temperatures are expressed in ° C. (degrees Centigrade). All reactions conducted under an inert atmosphere at room temperature unless otherwise noted.

$^1$H NMR spectra were recorded on a Varian VXR-300, a Varian Unity-300; a Varian Unity-400 instrument, or a General Electric QE-300. Chemical shifts are expressed in parts per million (ppm, δ units) relative to Me$_4$Si. Coupling constants are in units of hertz (Hz). Splitting patterns describe apparent multiplicities and are designated as s (singlet), d (doublet), t (triplet), q (quartet), m (multiplet), br (broad).

Low-resolution mass spectra (MS) were recorded via LCMS on a Micromass Q, ZMD, or QuattroMicro spectrometer; high resolution MS were obtained using a JOEL SX-102A spectrometer. All mass spectra were taken under electrospray ionization (ESI), chemical ionization (CI), electron impact (EI), atmospheric pressure chemical ionization (APCI) or by fast atom bombardment (FAB) methods. Infrared (IR) spectra were obtained on a Nicolet 510 FT-IR spectrometer using a 1-mm NaCl cell. All reactions were monitored by thin-layer chromatography on 0.25 mm E. Merck silica gel plates (60F-254), visualized with UV light, 5% ethanolic phosphomolybdic acid or p-anisaldehyde solution. Flash column chromatography was performed on silica gel (230-400 mesh, Merck). Optical rotations were obtained using a Perkin Elmer Model 241 Polarimeter. Melting points were determined using a Mel-Temp II apparatus and are uncorrected.

The following examples describe the syntheses of intermediates particularly useful in the synthesis of compounds of the present invention:

Example 1

N-Cyclopropyl-4-pyrazolo[1,5-b]pyridazin-3-yl-2-pyrimidinamine

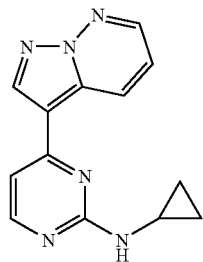

a) To a solution of (2E)-3-(dimethylamino)-1-pyrazolo[1,5-b]pyridazin-3-yl-2-propen-1-one (43 mg, 0.20 mmol) in DMF (2 mL) was added N-cyclopropylguanidine.0.5H$_2$SO$_4$ (160 mg, 0.80 mmol) and potassium carbonate (110 mg, 0.80 mmol). The reaction was heated at an oil bath temperature of 165° C. for about 18 hours. The mixture was cooled to RT and the solvent was removed in vacuo. The residue was dissolved in chloroform and filtered. The filtrate was purified by flash column chromatography (0-10% gradient MeOH/CH$_2$Cl$_2$) to give the title compound as a yellow solid (38 mg, 75%). $^1$H-NMR (400 MHz, d$^6$-DMSO) δ 9.13 (dd, 1H, J=9.0, 1.6 Hz), 8.77 (s, 1H), 8.53 (dd, 1H, J=4.4, 1.6 Hz), 8.24 (d, 1H, J=5.2 Hz), 7.38 (m, 1H), 7.10 (d, 1H, J=5.2 Hz), 2.72 (m, 1H), 0.71 (m, 2H), 0.47 (m, 2H); MS (ESI) (M+H)$^+$ 253.

b) (2E)-3-(Dimethylamino)-1-pyrazolo[1,5-b]pyridazin-3-yl-2-propen-1-one. To a solution of 1-pyrazolo[1,5-b]pyridazin-3-ylethanone (8.5 g, 52.7 mmol) in DMF (100 mL) was added dimethylformamide di-tert-butylacetal (16.1 g, 79.2 mmol). The reaction was heated at an oil bath temperature of 100° C. for about 4 hours. The solvent was removed in vacuo. The residue was triturated with diethyl ether to give the title compound as a brown solid (8 g, 70%). $^1$H-NMR (300 MHz, d$^6$-DMSO) δ 8.76 (dd, 1H, J=10.0, 2.0 Hz), 8.74 (s, 1H), 8.61 (dd, 1H, J=4.0, 2.0 Hz), 7.74 (d, 1H, J=12 Hz), 7.44 (dd, 1H, J=10.0, 4.0 Hz), 5.87 (d, 1H, J=12 Hz), 3.18 (bs, 3H), 2.97 (bs, 3H); MS (ESI) (M+H)$^+$ 217.

c) 1-Pyrazolo[1,5-b]pyridazin-3-ylethanone. To a slurry of 1-aminopyridazinium iodide (16 g, 72 mmol) in CH$_2$Cl$_2$ (200 mL) was added 3-butyne-2-one (2.4 g, 36 mmol). The reaction flask was cooled in an ice bath at 4° C. and a solution of KOH (5.0 g, 89 mmol) in water (100 mL) was added in one portion. The mixture was stirred at RT for about 4 hours. The organic layer was separated and the aqueous layer was extracted with CH$_2$Cl$_2$ (2×200 mL). The combined organic layers were dried (MgSO$_4$), filtered and concentrated in vacuo. The residue was triturated with diethyl ether to give the title compound as a red solid (4.0 g, 69%). $^1$H-NMR (300 MHz, CDCl$_3$) δ 8.78 (dd, 1H, J=9.0, 2.0 Hz), 8.51 (dd, 1H, J=4.4, 2.0 Hz), 8.47 (s, 1H), 7.35 (dd, 1H, J=9.0, 4.4 Hz), 2.63 (s, 3H); MS (ESI) (M+H)$^+$ 162.

d) 1-Aminopyridazinium iodide. Hydroxylamine-O-sulfonic acid (13.1 g, 115 mmol) was dissolved in water (25 mL) and the reaction flask was cooled in an icebath at 10° C. Aqueous KHCO$_3$ (48 mL, 2.4M) was added until the solution was at pH 5.0. Pyridazine (6.2 g, 77 mmol) was added in one portion and the flask was heated to 70° C. for about 1 hour. The pH was adjusted to 7.0 by the addition of aqueous KHCO$_3$ (approx. 10 mL, 2.4M). The reaction was cooled to 40° C. and the mixture was allowed to stir for about 1 hour. Potassium iodide (12.8 g, 77 mmol) in water (25 mL) was added. The solvent was removed in vacuo followed by the addition of 5% methanol in ethanol (100 mL). The solids were collected by filtration and dried in vacuo to give the title compound as a yellow solid (10.5 g, 61%). $^1$H-NMR (300 MHz, d$^6$-DMSO) δ 8.85 (bs, 2H), 9.27 (d, 1H, J=5.2 Hz), 9.12 (d, 1H, J=6.3 Hz), 8.49 (ddd, 1H, J=8.1, 6.3, 2.1 Hz), 8.14 (dd, 1H, J=8.1, 5.2 Hz).

e) N-Cyclopropylguanidine.0.5H$_2$SO$_4$. To a solution of O-methylisourea hydrogensulfate (50.0 g, 290 mmol) in water (150 mL) was added cyclopropyl amine (33.0 g, 581 mmol). The mixture was heated at an oil bath temperature of 100° C. for about 14 hours. The water was removed in vacuo. Ethanol (150 mL) was added and the solids isolated by filtration. The solids were dried under vacuum (1 torr) for about 18 hours to give the title compound as a white powder (47.6 g, 42%). $^1$H-NMR (300 MHz, d$^6$-DMSO) δ 2.0 (m, 1H), 0.20 (m, 2H), 0.10 (m, 2H).

Example 2

N-Cyclopropyl-N-methyl-4-pyrazolo[1,5-b]pyridazin-3-yl-2-pyrimidinamine

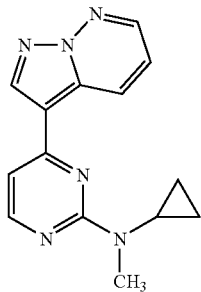

a) To a solution of N-cyclopropyl-4-pyrazolo[1,5-b]pyridazin-3-yl-2-pyrimidinamine (25 mg, 0.1 mmol) in DMF (2 mL) was added sodium hydride (6 mg, 0.25 mmol) and methyl iodide (0.013 mL, 0.15 mmol). The reaction was allowed to stir for about 1 hour. The reaction was concentrated in vacuo. Water (10 mL) was added and the aqueous layer was extracted with EtOAc (2×30 mL). The combined organic layers were dried (MgSO$_4$) filtered and concentrated in vacuo. The residue was triturated with diethylether to give the title compound as light orange solid (20 mg, 80%). $^1$H-NMR (400 MHz, CDCl$_3$) δ 9.07 (d, 1H, J=8.8 Hz), 8.46 (s, 1H), 8.35 (m, 2H) 7.12 (dd, 1H, J=8.8, 4.4 Hz), 6.89 (d, 1H, J=5.6 Hz), 3.23 (s, 3H), 2.85 (m, 1H), 0.94 (m, 2H), 0.73 (m, 2H); MS (ESI) (M+H)$^+$ 267.

Example 3

4-Pyrazolo[1,5-b]pyridazin-3-yl-N-(2,2,2-trifluoroethyl)-2-pyrimidinamine

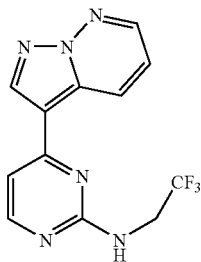

a) In a similar manner as described in Example 1a, from N-2,2,2-trifluoroethylguanidine.0.5H$_2$SO$_4$ was obtained the title compound as a yellow solid.

$^1$H-NMR (400 MHz, d$^6$-DMSO) δ 8.81 (s, 1H), 8.54 (dd, 1H, J=4.4, 2.0 Hz), 8.31 (d, 1H, J=5.6 Hz), 7.80 (bm, 1H), 7.40 (dd, 1H, J=8.8, 4.4 Hz), 7.21 (d, 1H, J=4.4 Hz), 4.17 (m, 2H); MS (APCI) (M+H)$^+$ 295.

b) N-(2,2,2-Trifluoroethyl)guanidine.0.5H$_2$SO$_4$. In a similar manner as described in Example 1e, from 2,2,2-trifluoroethyl amine was obtained the title compound (Tetrahedron Lett. (1993), 34(21), 3389; herein incorporated by reference) as a brown solid.

Example 4

N-Phenyl-4-pyrazolo[1,5-b]pyridazin-3-yl-2-pyrimidinamine

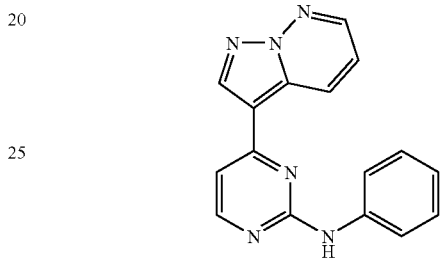

a) In a similar manner as described in Example 1a, from phenylguanidine.HNO$_3$ was obtained the title compound as a brown solid. $^1$H-NMR (300 MHz, d$^6$-DMSO) δ 9.61 (s, 1H), 9.2 (d, 1H, J=9.0 Hz), 8.93 (s, 1H), 8.63 (d, 1H, J=2.9 Hz), 8.50 (d, 1H, J=5.2 Hz), 7.78 (d, 2H, J=8.1 Hz), 7.49 (dd, 1H, J=9.0, 4.1 Hz), 7.37 (m, 3H), 7.02 (t, 1H, J=7.3 Hz); MS (ESI) (M+H)$^+$ 289.

Example 5

N-(4-Chlorophenyl)-4-pyrazolo[1,5-b]pyridazin-3-yl-2-pyrimidinamine

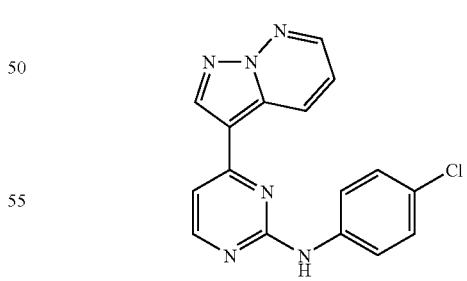

a) In a similar manner as described in Example 1a, from N-(4-chlorophenyl)guanidine.HNO$_3$ was obtained the title compound as a brown solid. $^1$H-NMR (300 MHz, d$^6$-DMSO) δ 9.76 (s, 1H), 9.19 (d, 1H, J=8.8 Hz), 8.94 (s, 1H), 8.64 (d, 1H, J=2.8 Hz), 8.51 (d, 1H, J=8.8 Hz), 7.84 (d, 2H, J=8.8 Hz), 7.53 (dd, 1H, J=9.2, 4.5 Hz), 7.42 (m, 3H); MS (ESI) (M+H)$^+$ 323.

Example 6

N-(4-Fluorophenyl)-4-pyrazolo[1,5-b]pyridazin-3-yl-2-pyrimidinamine

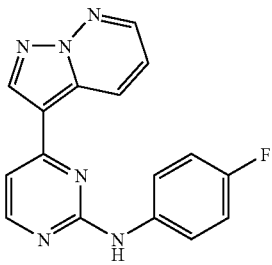

a) In a similar manner as described in Example 1a, from N-(4-fluorophenyl)guanidine.HNO$_3$ was obtained the title compound as a yellow solid. $^1$H-NMR (300 MHz, d$^6$-DMSO) δ 9.63 (s, 1H), 9.15 (d, 1H, J=8.7 Hz), 8.92 (s, 1H), 8.64 (dd, 1H, J=4.5, 1.8 Hz), 8.48 (d, 1H, J=5.3 Hz), 7.78 (dd, 2H, J=9.0, 5.0 Hz), 7.50 (dd, 1H, J=9.1, 4.6 Hz), 7.40 (d, 1H, J=5.3 Hz), 7.21 (t, 2H, J=8.9 Hz); MS (ESI) (M+H)$^+$ 307.

Example 7

3-[(4-Pyrazolo[1,5-b]pyridazin-3-yl-2-pyrimidinyl)amino]benzonitrile

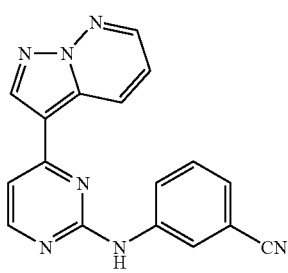

a) In a similar manner as described in Example 1a, from N-(3-cyanophenyl)guanidine.HNO$_3$ was obtained the title compound as a yellow solid. $^1$H-NMR (300 MHz, d$^6$-DMSO) δ 9.99 (s, 1H), 9.17 (d, 1H, J=9.0 Hz), 8.96 (s, 1H), 8.66 (dd, 1H, J=4.4, 1.6 Hz), 8.58 (d, 1H, J=5.3 Hz), 8.41 (s, 1H), 7.97 (d, 1H, J=8.2 Hz), 7.60-7.44 (m, 4H); MS (APCI) (M+H)$^+$ 314.

b) N-(3-Cyanophenyl)guanidine.HNO$_3$. To a solution of 3-aminobenzonitrile (3.31 g, 28 mmol) in EtOH (28 mL) was added cyanamide (2.5 mL of a 50% w/w solution in water). HNO$_3$ (1.98 mL, 14.2 M) is added dropwise. The mixture was heated at an oil bath temperature of 100° C. for about 3 hours. The flask was allowed to cool to RT. Et$_2$O (20 mL) was added and the solids isolated by filtration. The solids were dried under vacuum (1 torr) for about 18 hours to give the title compound as a beige powder (2.9 g, 46%). $^1$H-NMR (300 MHz, d$^6$-DMSO) δ 9.80 (s, 1H), 7.77 (m, 2H), 7.69-7.57 (m, 6H); MS (ESI) (M+H)$^+$ 161.

Example 8

4-[(4-Pyrazolo[1,5-b]-pyridazin-3-yl-2-pyrimidinyl)amino]benzoic acid

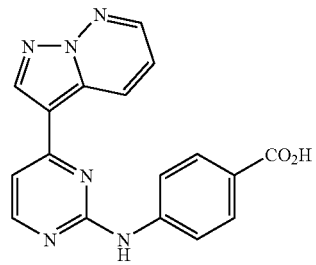

a) In a similar manner as described in Example 1a, 4-{[amino(imino)methyl]amino}benzoic acid.HCl was obtained the title compound as a yellow solid. $^1$H-NMR (300 MHz, d$^6$-DMSO) δ 9.99 (s, 1H), 9.25 (d, 1H, J=9.0 Hz), 8.96 (s, 1H), 8.65 (dd, 1H, J=4.5, 2.6 Hz), 8.57 (d, 1H, J=5.2 Hz), 7.93 (m, 4H), 7.53 (dd, 1H, J=8.9, 4.4 Hz), 7.50 (d, 1H, J=5.5 Hz); MS (APCI) (M+H)$^+$ 333.

Example 9

4-Pyrazolo[1,5-b]pyridazin-3-yl-N-[3-(trifluoromethyl)phenyl]-2-pyrimidinamine

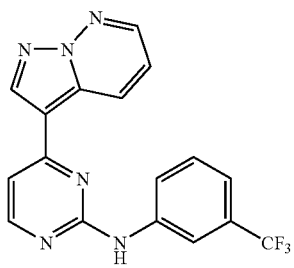

a) In a similar manner as described in Example 1a, from N-[3-(trifluoromethyl)phenyl]guanidine was obtained the title compound as a brown solid. $^1$H-NMR (300 MHz, d$^6$-DMSO) δ 9.98 (s, 1H), 9.17 (d, 1H, J=8.9 Hz), 8.95 (s, 1H), 8.65 (bs, 1H), 8.57 (d, 1H, J=5.4 Hz), 8.32 (bs, 1H), 8.00 (d, 1H, J=8.1 Hz), 7.59 (t, 1H, J=8.0 Hz), 7.48 (m, 2H), 7.34 (d, 1H, J=8.1 Hz); MS (ESI) (M+H)$^+$ 357.

Example 10

N-(3-Nitrophenyl)-4-pyrazolo[1,5-b]pyridazin-3-yl-2-pyrimidinamine

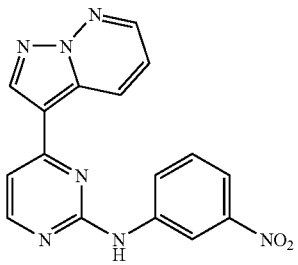

a) In a similar manner as described in Example 1a, from N-(3-nitrophenyl)guanidine was obtained the title compound as a brown solid. $^1$H-NMR (300 MHz, d$^6$-DMSO) δ 10.15 (s, 1H), 9.18 (d, 1H, J=8.9 Hz), 8.97 (s, 1H), 8.93 (s, 1H), 8.66 (d, 1H, J=4.4 Hz), 8.60 (d, 1H, J=5.1 Hz), 8.11 (d, 1H, J=8.1 Hz), 7.85 (d, 1H, J=8.1 Hz), 7.64 (t, 1H, J=8.1 Hz), 7.50 (m, 2H); MS (ESI) (M+H)$^+$ 357.

b) N-(3-Nitrophenyl)guanidine.HCl. In a similar manner as described in Example 1e, from 3-nitrophenyl aniline was obtained the title compound (Anal. Biochem. (1999), 276(2), 251) as a brown solid.

Example 11

N-(2-Chlorophenyl)-4-pyrazolo[1,5-b]pyridazin-3-yl-2-pyrimidinamine

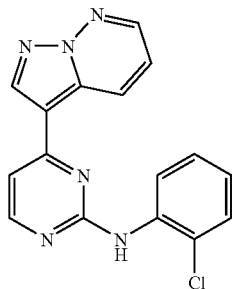

a) In a similar manner as described in Example 1a, from N-(2-chlorophenyl)guanidine was obtained the title compound as a brown solid. $^1$H-NMR (300 MHz, d$^6$-DMSO) δ 9.06 (s, 1H), 8.90 (s, 1H), 8.84 (d, 1H, J=9.0 Hz), 8.60 (bs, 1H), 8.44 (d, 1H, J=5.2 Hz), 7.81 (d, 1H, J=8.1 Hz), 7.59 (d, 1H, J=7.9 Hz), 7.39 (m, 3H), 7.26 (t, 1H, J=7.6 Hz); MS (ESI) (M+H)$^+$ 323.

b) N-(2-Chlorophenyl)guanidine.HCl. Prepared from 2-chlorophenyl aniline as described in (J. Med. Chem. (1996), 39(20), 4017).

Example 12

N-(4-Methoxyphenyl)-4-pyrazolo[1,5-b]pyridazin-3-yl-2-pyrimidinamine

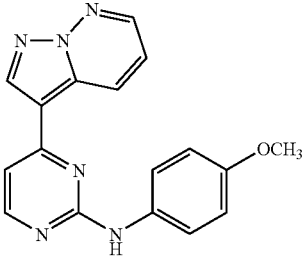

a) In a similar manner as described in Example 1a, from N-(4-methoxyphenyl)guanidine was obtained the title compound as a brown solid. $^1$H-NMR (300 MHz, d$^6$-DMSO) δ 9.41 (s, 1H), 9.15 (bs, 1H), 8.90 (s, 1H), 8.62 (d, 1H, J=2.6 Hz), 8.44 (d, 1H, J=5.3 Hz), 7.64 (d, 2H, J=8.9 Hz), 7.47 (dd, 1H, J=9.1, 4.5 Hz), 7.33 (d, 1H, J=5.2 Hz), 6.95 (d, 1H, J=8.9 Hz), 3.78 (s, 3H); MS (ESI) (M+H)$^+$ 319.

Example 13

4-Pyrazolo[1,5-b]pyridazin-3-yl-N-(3,4,5-trimethoxyphenyl)-2-pyrimidinamine

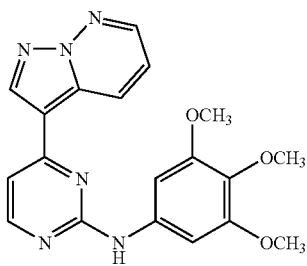

a) In a similar manner as described in Example 1a, from N-(3,4,5-trimethoxyphenyl)guanidine was obtained the title compound as a brown solid. $^1$H-NMR (300 MHz, d$^6$-DMSO) δ 9.50 (s, 1H), 9.21 (d, 1H, J=9.7 Hz), 8.92 (s, 1H), 8.63 (d, 1H, J=2.7 Hz), 8.50 (d, 1H, J=5.2 Hz), 7.47 (dd, 1H, J=9.1, 4.5 Hz), 7.38 (d, 1H, J=5.2 Hz), 7.18 (s, 2H); MS (ESI) (M+H)$^+$ 379.

b) N-(3,4,5-Trimethoxyphenyl)guanidine.HNO$_3$. In a similar manner as described in Example 7b, from 3,4,5-trimethoxy aniline was obtained the title compound (J. Med. Chem. (1975), 18(11), 1077) as a brown solid.

Example 14

N-[3-(1,3-Oxazol-5-yl)phenyl]-4-pyrazolo[1,5-b]pyridazin-3-yl-2-pyrimidinamine

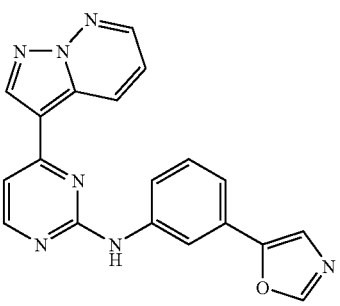

a) In a similar manner as described in Example 1a, from N-[3-(1,3-oxazol-5-yl)phenyl]guanidine was obtained the title compound as a brown solid. $^1$H-NMR (300 MHz, d$^6$-DMSO) δ 9.78 (s, 1H), 9.18 (d, 1H, J=8.9 Hz), 8.95 (s, 1H), 8.64 (d, 1H, J=3.1 Hz), 8.55 (d, 1H, J=5.2 Hz), 8.46 (s, 1H), 8.24 (s, 1H), 7.75 (d, 1H, J=7.9 Hz), 7.67 (s, 1H), 7.49-7.39 (m, 3H), 7.35 (dd, 1H, J=9.0, 4.5 Hz); MS (ESI) (M+H)$^+$ 356.

b) N-[3-(1,3-Oxazol-5-yl)phenyl]guanidine.HNO$_3$. In a similar manner as described in Example 7b, from 3-(1,3-oxazol-5-yl)aniline was obtained the title compound as a brown solid. $^1$H-NMR (300 MHz, d$^6$-DMSO) δ 9.70 (s, 1H), 8.52 (s, 1H), 7.80 (s, 1H), 7.70-7.43 (m, 7H), 7.27 (d, 1H, J=7.9 Hz); MS (ESI) (M+H)$^+$ 203.

Example 15

N-(4-Pyrazolo[1,5-b]pyridazin-3-yl-2-pyrimidinyl)-1H-benzimidazol-6-amine

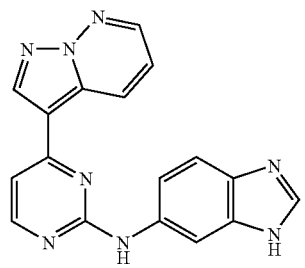

a) In a similar manner as described in Example 1a, from N-(1H-benzimidazol-6-yl)guanidine.HNO$_3$ was obtained the title compound as a brown solid. $^1$H-NMR (300 MHz, d$^6$-DMSO) δ 12.35 (bs, 1H), 9.59 (s, 1H), 9.21 (d, 1H, J=9.2 Hz), 8.93 (s, 1H), 8.64 (d, 1H, J=2.7 Hz), 8.50 (d, 1H, J=5.2 Hz), 8.18 (s, 1H), 8.16 (s, 1H), 7.58 (d, 1H, J=8.5 Hz), 7.45-7.41 (m, 2H), 7.37 (d, 1H, J=5.2 Hz); MS (ESI) (M+H)$^+$ 329.

c) N-(1H-Benzimidazol-6-yl)guanidine.HNO$_3$. In a similar manner as described in Example 7b, from 1H-benzimidazol-6-amine was obtained the title compound as a brown solid. $^1$H-NMR (400 MHz, d$^6$-DMSO) δ 9.76 (s, 1H), 9.40 (s, 1H), 7.85 (d, 1H, J=8.8 Hz), 7.69 (d, 1H, J=1.8 Hz), 7.42 (bs, 4H), 7.37 (dd, 1H, J=8.8, 1.8 Hz); MS (ESI) (M+H)$^+$ 176.

Example 16

N-(4-Pyrazolo[1,5-b]pyridazin-3-yl-2-pyrimidinyl)-1,3-benzoxazol-2-amine

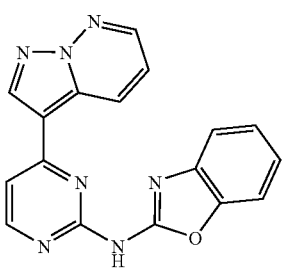

a) In a similar manner as described in Example 1a, from N-(1,3-benzoxazol-2-yl)guanidine was obtained the title compound as a brown solid. $^1$H-NMR (300 MHz, d$^6$-DMSO) δ 11.68 (s, 1H), 10.23 (d, 1H, J=9.1 Hz), 9.02 (s, 1H), 8.68-8.65 (m, 2H), 7.73-7.62 (m, 4H), 7.38-7.25 (m, 2H); MS (ESI) (M+H)$^+$ 330.

Example 17

N-(6-Chloro-1H-benzimidazol-2-yl)-N-(4-pyrazolo[1,5-b]pyridazin-3-yl-2-pyrimidinyl)amine

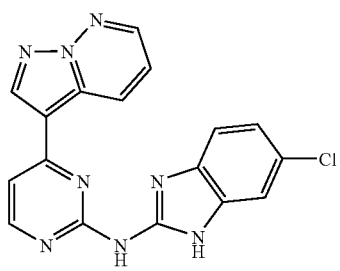

a) In a similar manner as described in Example 1a, from N-(6-Chloro-1H-benzimidazol-2-yl)guanidine was obtained the title compound as a brown solid. $^1$H-NMR (400 MHz, d$^6$-DMSO) δ 12.20 (s, 1H), 11.32 (s, 1H), 9.50 (d, 1H, J=8.0 Hz), 8.96 (s, 1H), 8.62 (dd, 1H, J=4.4, 1.8 Hz), 8.59 (d, 1H, J=5.5 Hz), 7.56 (d, 1H, J=5.5 Hz), 7.48 (dd, 1H, J=9.0, 4.4 Hz), 7.53 (m, 1H), 7.40 (m, 1H), 7.06 (m, 1H); MS (ESI) (M+H)$^+$ 363.

Example 18

N-(4-Chlorobenzyl)-4-pyrazolo[1,5-b]pyridazin-3-yl-2-pyrimidinamine

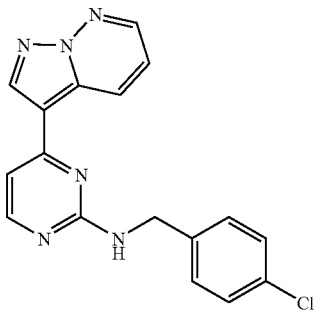

a) In a similar manner as described in Example 1a, from N-(4-chlorobenzyl)guanidine was obtained the title compound as a brown solid. $^1$H-NMR (400 MHz, d$^6$-DMSO) δ 9.20 (bs, 1H), 8.78 (bs, 1H), 8.54 (bs, 1H), 8.27 (d, 1H, J=5.1 Hz), 7.82 (m, 1H), 7.39 (m, 5H), 7.12 (d, 1H, J=5.4 Hz), 4.54 (s, 2H); MS (ESI) (M+H)$^+$ 337.

b) N-(4-Chlorobenzyl)guanidine.HO$_2$CCF$_3$. Prepared from 4-chlorobenzylamine as described in (J. Med. Chem. (1975), 18(3), 304), herein incorporated by reference.

Example 19

N$^1$,N$^1$-Dimethyl-N$^3$-(4-pyrazolo[1,5-b]pyridazin-3-yl-2-pyrimidinyl)-1,3-propanediamine

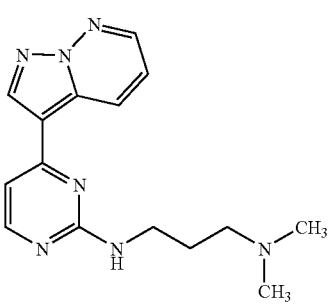

a) In a similar manner as described in Example 1a, from N-[3-(dimethylamino)propyl]guanidine.0.5H$_2$SO$_4$ was obtained the title compound as a yellow solid. $^1$H-NMR (400 MHz, d$^6$-DMSO) δ 9.10 (bs, 1H), 8.76 (s, 1H), 8.53 (dd, 1H, J=4.4, 2.0 Hz), 8.21 (d, 1H, J=5.2 Hz), 7.38 (dd, 1H, J=9.2, 4.4 Hz), 7.21 (bs, 1H), 7.05 (d, 1H, J=5.2 Hz), 2.87 (m, 2H), 2.50 (m, 2H), 2.27 (bs, 6H), 1.73 (m, 2H); MS (APCI) (M+H)$^+$ 298.

b) N-[3-(Dimethylamino)propyl]guanidine.0.5H$_2$SO$_4$. In a similar manner as described in Example 1e, from N-3-(dimethylamino)propylamine was obtained the title compound as a white solid. $^1$H-NMR (300 MHz, D$_2$O) δ 3.19 (t, 2H, J=6.6 Hz), 3.04 (m, 2H), 2.75 (s, 6H), 1.93 (m, 2H).

Example 20

N-[3-(4-Morpholinyl)propyl]-4-pyrazolo[1,5-b]pyridazin-3-yl-2-pyrimidinamine

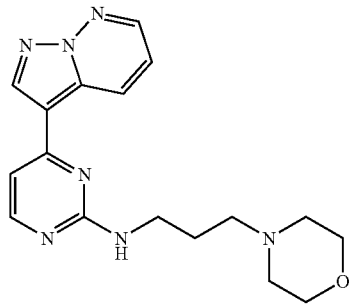

a) In a similar manner as described in Example 1a, from N-[3-(4-morpholinyl)propyl]guanidine.0.5H$_2$SO$_4$ was obtained the title compound as a yellow solid. $^1$H-NMR (300 MHz, d$^6$-DMSO) δ 9.10 (bs, 1H), 8.84 (s, 1H), 8.61 (dd, 1H, J=4.2, 2.0 Hz), 8.29 (d, 1H, J=5.1 Hz), 7.46 (dd, 1H, J=9.0, 4.2 Hz), 7.27 (bs, 1H), 7.11 (d, 1H, J=5.1 Hz), 3.58 (m, 2H), 3.40 (m, 2H), 3.31 (m, 2H), 2.54 (m, 2H), 2.40 (m, 4H), 1.78 (m, 2H); MS (APCI) (M+H)$^+$ 340.

b) N-[3-(4-Morpholinyl)propyl]guanidine.0.5H$_2$SO$_4$. In a similar manner as described in Example 1e, from N-3-(4-morpholinyl)propylamine was obtained the title compound (Bioorg. Med. Chem. Lett. (1997), 7(6), 675, incorporated herein by reference) as a white solid. $^1$H-NMR (400 MHz, d$^6$-DMSO) δ 3.58 (bm, 4H), 3.15 (m, 4H), 3.05 (m, 4H), 1.85 (m, 2H).

Example 21

N-[3-(4-Methyl-1-piperazinyl)propyl]-4-pyrazolo[1,5-b]pyridazin-3-yl-2-pyrimidinamine

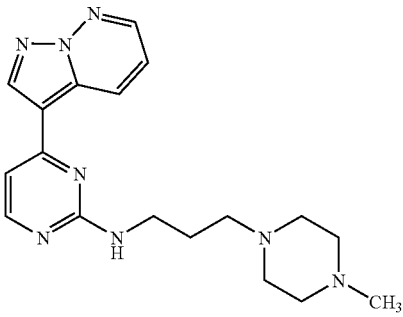

a) In a similar manner as described in Example 1a, from N-[3-(4-methyl-1-piperazinyl)propyl]guanidine.0.5H$_2$SO$_4$ was obtained the title compound as a yellow solid. $^1$H-NMR (400 MHz, d$^6$-DMSO) δ 9.00 (bs, 1H), 8.76 (s, 1H), 8.53 (dd, 1H, J=4.4, 2.0 Hz), 8.21 (d, 1H, J=5.6 Hz), 7.37 (dd, 1H, J=8.8, 4.0 Hz), 7.20 (bs, 1H), 7.03 (d, 1H, J=5.2 Hz), 3.32 (m, 6H), 2.34 (m, 6H), 2.11 (m, 3H), 1.68 (m, 2H); MS (APCI) (M+H)$^+$ 353.

b) N-[3-(4-Methyl-1-piperazinyl)propyl]guanidine.0.5H₂SO₄. In a similar manner as described in Example 1e, from N-3-(4-methyl-1-piperazinyl)propylamine was obtained the title compound (Bioorg. Med. Chem. Lett. (1997), 7(6), 675) as a white solid.

Example 22

1-{3-[(4-Pyrazolo[1,5-b]pyridazin-3-yl-2-pyrimidinyl)amino]propyl}-2-pyrrolidinone

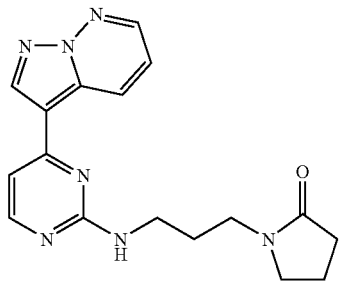

a) In a similar manner as described in Example 1a, from N-[3-(2-oxo-1-pyrrolidinyl)propyl]guanidine.HO₂CCF₃ was obtained the title compound as a yellow solid. ¹H-NMR (300 MHz, d⁶-DMSO) δ 9.08 (bs, 1H), 8.84 (s, 1H), 8.61 (m, 1H), 8.30 (d, 1H, J=5.1 Hz), 7.47 (dd, 1H, J=8.9, 4.4 Hz), 7.22 (bs, 1H), 7.13 (d, 1H, J=5.3 Hz), 3.35 (m, 4H), 2.52 (m, 2H), 2.23 (m, 2H), 1.95 (m, 2H), 1.79 (m, 2H); MS (ESI) (M+H)⁺ 338.

b) N-[3-(2-Oxo-1-pyrrolidinyl)propyl]guanidine.HO₂CCF₃. In a similar manner as described in Example 1e, from 1-(3-aminopropyl)-2-pyrrolidinone was obtained the title compound as a white solid.

Example 23

N-[3-Chloro-4-(4-methyl-1-piperazinyl)phenyl]-4-pyrazolo[1,5-b]pyridazin-3-yl-2-pyrimidinamine

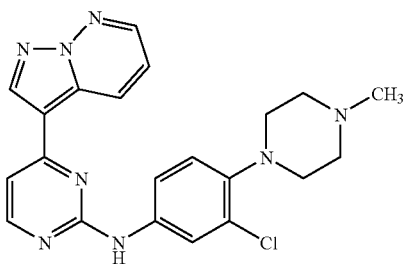

a) In a similar manner as described in Example 1a, from N-[3-chloro-4-(4-methyl-1-piperazinyl)phenyl]guanidine-.HNO₃ was obtained the title compound as a yellow solid. ¹H-NMR (300 MHz, d⁶-DMSO) δ 9.95 (s, 1H), 9.16 (d, 1H, J=8.6 Hz), 8.93 (s, 1H), 8.64 (m, 1H), 8.50 (d, 1H, J=2.4 Hz), 7.54 (dd, 1H, J=8.6, 2.4 Hz), 7.49 (dd, 1H, J=9.1, 4.4 Hz), 7.41 (d, 1H, J=5.2 Hz), 7.19 (d, 1H, J=8.8 Hz), 2.95 (m, 4H), 2.51 (m, 4H), 2.28 (s, 3H); MS (ESI) (M+H)⁺ 421.

b) N-[3-Chloro-4-(4-methyl-1-piperazinyl)phenyl]guanidine.HNO₃. In a similar manner as described in Example 7b, from 3-chloro-4-(4-methyl-1-piperazinyl)aniline was obtained the title compound as a white solid.

Example 24

N-[4-(4-Methyl-1-piperazinyl)phenyl]-4-pyrazolo[1,5-b]pyridazin-3-yl-2-pyrimidinamine

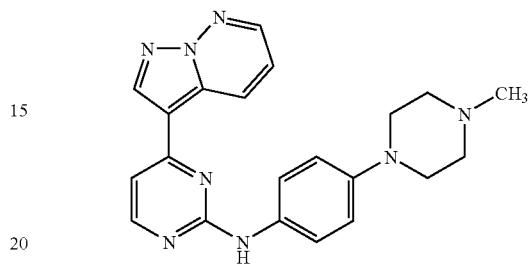

a) In a similar manner as described in Example 1a, from N-[4-(4-methyl-1-piperazinyl)phenyl]guanidine.HCl was obtained the title compound as a yellow solid.

¹H-NMR (300 MHz, CDCl₃) δ 8.89 (d, 1H, J=9.0 Hz), 8.52 (s, 1H), 8.40 (m, 2H), 7.49 (d, 2H, J=8.8 Hz), 7.30 (s, 1H), 7.12 (dd, 1H, J=9.0, 4.3 Hz), 7.04 (m, 2H), 6.95 (m, 1H), 3.26 (m, 4H), 2.66 (m, 4H), 2.42 (s, 3H); MS (ESI) (M+H)⁺ 387.

b) N-[4-(4-Methyl-1-piperazinyl)phenyl]guanidine.HCl. Prepared from 4-(4-methyl-1-piperazinyl)aniline as described in (J. Med. Chem. (1993), 36(19), 2716).

Example 25

N-[3-Methyl-4-(4-methyl-1-piperazinyl)phenyl]-4-pyrazolo[1,5-b]pyridazin-3-yl-2-pyrimidinamine

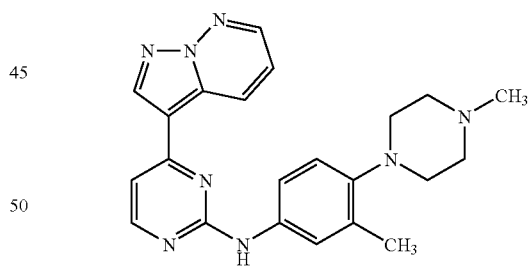

a) In a similar manner as described in Example 1a, from N-[3-methyl-4-(4-methyl-1-piperazinyl)phenyl]guanidine-.HNO₃ was obtained the title compound as a brown solid. ¹H-NMR (400 MHz, d⁶-DMSO) δ 9.35 (s, 1H), 9.11 (d, 1H, J=8.2 Hz), 8.86 (s, 1H), 8.58 (dd, 1H, J=4.6, 1.9 Hz), 8.41 (d, 1H, J=5.1 Hz), 7.55 (d, 1H, J=2.4 Hz), 7.43-7.40 (m, 2H), 7.30 (d, 1H, J=5.3 Hz), 7.00 (d, 1H, J=8.6 Hz), 2.83-2.81 (m, 4H), 2.50-2.48 (m, 4H), 2.24 (m, 6H); MS (ESI) (M+H)⁺ 401.

b) N-[3-Methyl-4-(4-methyl-1-piperazinyl)phenyl]guanidine.HNO₃. In a similar manner as described in Example 7b, from 3-methyl-4-(4-methyl-1-piperazinyl)aniline was obtained the title compound as a brown solid.

Example 26

N-[4-(4-Methyl-1-piperazinyl)-3-(trifluoromethyl)phenyl]-4-pyrazolo[1,5-b]pyridazin-3-yl-2-pyrimidinamine

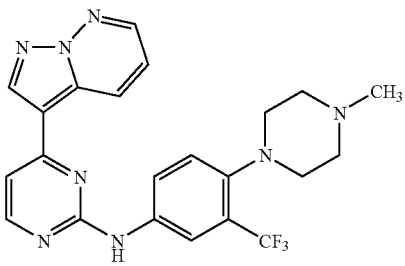

a) In a similar manner as described in Example 1a, from N-[4-(4-methyl-1-piperazinyl)-3-(trifluoromethyl)phenyl]guanidine.HNO$_3$ was obtained the title compound as a yellow solid. $^1$H-NMR (400 MHz, d$^6$-DMSO) δ 9.80 (s, 1H), 9.10 (d, 1H, J=8.1 Hz), 8.89 (s, 1H), 8.60 (dd, 1H, J=4.4, 2.0 Hz), 8.48 (d, 1H, J=5.3 Hz), 8.14 (d, 1H, J=2.4 Hz), 7.93 (d, 1H, J=8.8 Hz), 7.53 (d, 1H, J=8.8 Hz), 7.42 (m, 2H), 2.284 (m, 4H), 2.48 (m, 4H), 2.24 (s, 3H); MS (ESI) (M+H)$^+$ 455.

b) N-[4-(4-Methyl-1-piperazinyl)-3-(trifluoromethyl)phenyl] guanidine.HNO$_3$. In a similar manner as described in Example 7b, from 4-(4-methyl-1-piperazinyl)-3-(trifluoromethyl)phenylamine was obtained the title compound as a white solid.

Example 27

N-[3-Chloro-4-(4-morpholinyl)phenyl]-4-pyrazolo[1,5-b]pyridazin-3-yl-2-pyrimidinamine

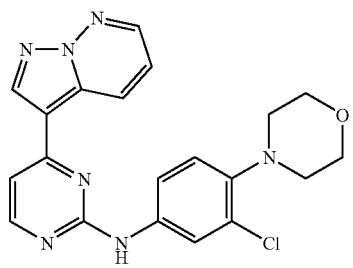

a) In a similar manner as described in Example 1a, from N-[3-chloro-4-(4-morpholinyl)phenyl]guanidine.HNO$_3$ was obtained the title compound as a yellow solid. $^1$H-NMR (300 MHz, d$^6$-DMSO) δ 9.67 (s, 1H), 9.17 (d, 1H, J=9.3 Hz), 8.93 (s, 1H), 8.64 (dd, 1H, J=4.4, 1.8 Hz), 8.51 (d, 1H, J=5.2 Hz), 8.06 (d, 1H, J=2.5 Hz), 7.58 (dd, 1H, J=8.7, 2.4 Hz), 7.50 (dd, 1H, J=9.1, 4.5 Hz), 7.42 (d, 1H, J=5.4 Hz), 7.21 (d, 1H, J=8.6 Hz), 3.77 (m, 4H), 2.97 (m, 4H); MS (ESI) (M+H)$^+$ 408.

b) N-[3-Chloro-4-(4-morpholinyl)phenyl]guanidine.HNO$_3$. In a similar manner as described in Example 7b, from 3-chloro-4-(4-morpholinyl)aniline was obtained the title compound as a brown solid. $^1$H-NMR (300 MHz, d$^6$-DMSO) δ 9.50 (s, 1H), 7.37 (bs, 5H), 7.23 (s, 2H), 3.77 (m, 4H), 2.99 (m, 4H); MS (ESI) (M+H)$^+$ 255.

Example 28

N-{4-[(Diethylamino)methyl]phenyl}-4-pyrazolo[1,5-b]pyridazin-3-yl-2-pyrimidinamine

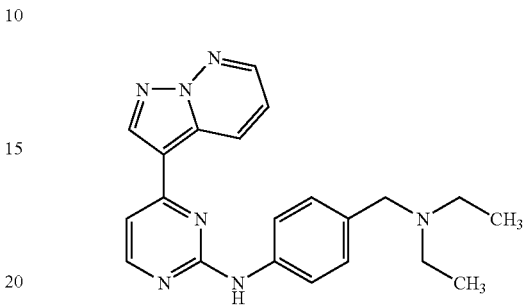

a) In a similar manner as described in Example 1a, from N-[4-(4-methyl-1-piperazinyl)-3-(trifluoromethyl)phenyl]guanidine.HNO$_3$ was obtained the title compound as a yellow solid. $^1$H-NMR (400 MHz, d$^6$-DMSO) δ 9.75 (bs, 1H), 9.40 (bs, 1H), 9.17 (d, 1H, J=8.8 Hz), 8.89 (s, 1H), 8.62 (d, 1H, J=2.7 Hz), 8.48 (d, 1H, J=5.1 Hz), 7.82 (bs, 2H), 7.45-7.39 (m, 3H), 4.24 (bs, 2H), 3.22 (bs, 4H), 1.20 (bs, 6H); MS (ESI) (M+H)$^+$ 374.

b) N{4-[(Diethylamino)methyl]phenyl}guanidine.HNO$_3$. In a similar manner as described in Example 7b, from 4-[(diethylamino)methyl]aniline was obtained the title compound as a brown solid.

Example 29

N-[2-(Diethylamino)ethyl]-4-[(4-pyrazolo[1,5-b]pyridazin-3-yl-2-pyrimidinyl)amino]benzamide

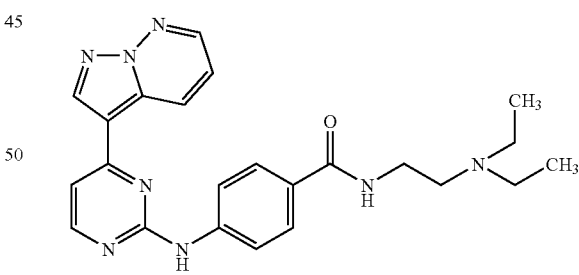

a) In a similar manner as described in Example 1a, from 4-{[amino(imino)methyl]amino}-N-[2-(diethylamino)ethyl]benzamide.HNO$_3$ was obtained the title compound as a yellow solid. $^1$H-NMR (300 MHz, d$^6$-DMSO) δ 9.89 (s, 1H), 9.24 (d, 1H, J=7.5 Hz), 8.95 (s, 1H), 8.66 (dd, 1H, J=4.5, 1.9 Hz), 8.56 (d, 1H, J=5.2 Hz), 7.90-7.83 (m, 4H), 7.52 (dd, 1H, J=9.0, 4.5 Hz), 7.47 (d, 1H, J=5.4 Hz), 5.42 (bs, 2H), 3.35 (bs, 2H), 2.60 (bs, 4H), 1.02 (bs, 6H); MS (ESI) (M+H)$^+$ 431.

b) 4{[Amino(imino)methyl]amino}N-[2-(diethylamino)ethyl]benzamide.HNO$_3$. In a similar manner as described in Example 7b, from 4-amino-N-[2-(diethylamino)ethyl]benzamide was obtained the title compound as a brown solid.

Example 30

N-Cyclopropyl-4-(2-methylpyrazolo[1,5-b]pyridazin-3-yl)-2-pyrimidinamine

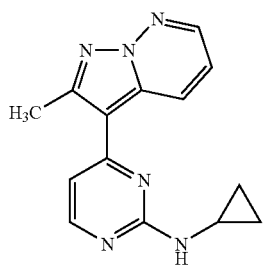

a) To a solution (2E)-3-(dimethylamino)-1-(2-methylpyrazolo[1,5-b]pyridazin-3-yl)-2-propen-1-one (50 mg, 0.22 mmol) in DMF (2.5 mL) was added N-cyclopropylguanidine.0.5$H_2SO_4$ (130 mg, 0.66 mmol) and potassium carbonate (152 mg, 1.10 mmol). The reaction was heated at an oil bath temperature of 135° C. for about 18 hours. The mixture was cooled to RT and the solvent was removed in vacuo. The residue was dissolved in chloroform and filtered. The filtrate was concentrated in vacuo then dissolved in $CH_2Cl_2$ and triturated with diethylether to give the title compound as a yellow solid (22 mg, 38%). $^1$H-NMR (300 MHz, $CDCl_3$) δ 9.02 (d, 1H, J=8.8 Hz), 8.39 (d, 1H, J=5.2 Hz), 8.35 (dd, 1H, J=4.4, 2.0 Hz), 7.15 (dd, 1H, J=8.8, 4.4 Hz), 6.94 (d, 1H, J=5.3 Hz), 5.45 (s, 1H), 2.89 (m, 1H), 2.83 (s, 3H), 0.91 (m, 2H), 0.68 (m, 2H); MS (ESI) (M+H)$^+$ 267.

b) (2E)-3-(Dimethylamino)-1-(2-methylpyrazolo[1,5-b]pyridazin-3-yl)-2-propen-1-one. 1-(2-Methylpyrazolo[1,5-b]pyridazin-3-yl)ethanone (165 mg, 0.95 mmol) was added to DMF dimethylacetal (6.0 mL). The reaction was heated at an oil bath temperature of 120° C. for about 3 days. The solvent was removed in vacuo. The residue was triturated with diethylether to give the title compound as a brown solid (60 mg, 26%). $^1$H-NMR (300 MHz, $CDCl_3$) δ 8.68 (dd, 1H, J=9.1, 2.0 Hz), 8.32 (dd, 1H, J=4.5, 2.0 Hz), 7.83 (d, 1H, J=12.4 Hz), 7.14 (dd, 1H, J=9.1, 4.5 Hz), 5.59 (d, 1H, J=12.4 Hz), 2.91-3.10 (bm, 6H), 2.81 (s, 3H); MS (APCI) (M+H)$^+$ 231.

c) 1-(2-Methylpyrazolo[1,5-b]pyridazin-3-yl)ethanone. To a slurry of 1-aminopyridazinium iodide (709 mg, 3.2 mmol) in DMSO (6.0 mL) was added 3-pentyne-2-one (1.45 g, 6.4 mmol) as a solution (2:1 by $^1$H NMR) in THF. The reaction flask was cooled in an ice bath at 4° C. then KOH (178 mg, 3.2 mmol) and $K_2CO_3$ (219 mg, 1.59 mmol) were added in one portion. The bath was removed and the mixture was stirred at RT for about 4 hours. Water was added (20 mL). The organic layer was separated and the aqueous layer was extracted with $CH_2Cl_2$ (3×20 mL). The combined organic layers were dried ($MgSO_4$), filtered and concentrated in vacuo. The residue was triturated with diethyl ether and EtOAc to give the title compound as a red solid (165 mg, 29%). $^1$H-NMR (300 MHz, $CDCl_3$) δ 8.69 (dd, 1H, J=9.1, 2.0 Hz), 8.42 (dd, 1H, J=4.7, 2.0 Hz), 7.29 (dd, 1H, J=9.1, 4.7 Hz), 2.82 (s, 3H), 2.62 (s, 3H).

d) 3-Pentyn-2-one. Propyne was condensed in THF at −78° C. until saturated. nBuLi (10 mL, 25 mmol) was added in one portion. The reaction mixture was stirred for 10 minutes then dimethylacetamide (2.3 mL, 25 mmol) was added. The cooling bath was removed an the mixture was stirred at RT for about 1 hour. Water was added (100 mL) followed by the addition of diethylether (200 mL). The combined organic layers were dried ($MgSO_4$), filtered and concentrated in vacuo to about 2 mL. The THF solution was used in the next step.

Example 31

N-Cyclopropyl-4-(2-ethylpyrazolo[1,5-b]pyridazin-3-yl)-2-pyrimidinamine

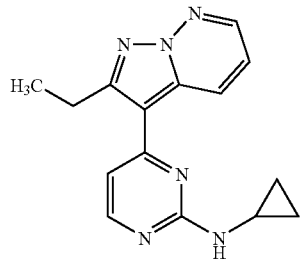

a) To a solution (2E)-3-(dimethylamino)-1-(2-ethylpyrazolo[1,5-b]pyridazin-3-yl)-2-propen-1-one (75 mg, 0.31 mmol) in DMF (2.0 mL) was added N-cyclopropylguanidine.0.5$H_2SO_4$ (181 mg, 0.92 mmol) and potassium carbonate (212 mg, 1.54 mmol). The reaction was heated at an oil bath temperature of 135° C. for about 18 hours. The mixture was cooled to RT and the solvent was removed in vacuo. The residue was dissolved in chloroform and filtered. The filtrate was concentrated in vacuo then dissolved in $CH_2Cl_2$ and triturated with diethylether and hexanes to give the title compound as an orange solid (32 mg, 36%). $^1$H-NMR (300 MHz, $CDCl_3$) δ 8.96 (d, 1H, J=8.7 Hz), 8.38 (d, 1H, J=5.4 Hz), 8.34 (dd, 1H, J=4.4, 1.9 Hz), 7.14 (dd, 1H, J=9.0, 4.5 Hz), 6.92 (d, 1H, J=5.4 Hz), 5.47 (s, 1H), 3.23 (q, 2H, J=7.5 Hz), 2.88 (m, 1H), 1.50 (t, 3H, J=7.5 Hz), 0.91 (m, 2H), 0.67 (m, 2H); MS (ESI) (M+H)$^+$ 281.

b) (2E)-3-(Dimethylamino)-1-(2-ethylpyrazolo[1,5-b]pyridazin-3-yl)-2-propen-1-one. 1-(2-Ethylpyrazolo[1,5-b]pyridazin-3-yl)ethanone (350 mg, 1.85 mmol) was added to DMF dimethylacetal (9.0 mL). The reaction was heated at an oil bath temperature of 120° C. for about 3 days. The solvent was removed in vacuo. The residue was triturated with diethylether to give the title compound as a brown solid (75 mg, 17%). The crude material was used without purification in the next step.

c) 1-(2-Ethylpyrazolo[1,5-b]pyridazin-3-yl)ethanone. To a slurry of 1-aminopyridazinium iodide (1.60 g, 7.2 mmol) in DMSO (14.0 mL) was added 3-hexyne-2-one (1.57 mL, 14.4 mmol). The reaction flask was cooled in an ice bath at 4° C. then KOH (403 mg, 7.2 mmol) and $K_2CO_3$ (500 mg, 3.6 mmol) were added in one portion. The bath was removed and the mixture was stirred at RT for about 1 hour. Water was added (60 mL). The organic layer was separated and the aqueous layer was extracted with $CH_2Cl_2$ (3×50 mL). The combined organic layers were dried ($MgSO_4$), filtered and concentrated in vacuo. The residue was triturated with diethyl ether and EtOAc to give the title compound as a red solid (350 mg, 26%). $^1$H-NMR (300 MHz, $CDCl_3$) δ 8.67 (dd, 1H, J=9.0, 2.0 Hz), 8.42 (dd, 1H, J=4.5, 2.0 Hz), 7.29 (dd, 1H, J=9.0, 4.5 Hz), 3.23 (q, 2H, J=7.5 Hz), 2.66 (s, 3H), 1.50 (t, 3H, J=7.5 Hz); MS (ESI) (M+H)+ 245.

Example 32

4-(2-Butylpyrazolo[1,5-b]pyridazin-3-yl)-N-cyclopropyl-2-pyrimidinamine

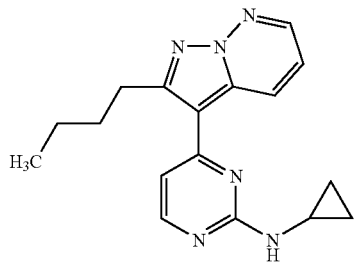

a) To a solution (2E)-3-(dimethylamino)-1-(2-methylpyrazolo[1,5-b]pyridazin-3-yl)-2-propen-1-one (50 mg, 0.22 mmol) in DMF (2.5 mL) was added N-cyclopropylguanidine.0.5H$_2$SO$_4$ (130 mg, 0.66 mmol) and potassium carbonate (152 mg, 1.10 mmol). The reaction was heated at an oil bath temperature of 135° C. for about 18 hours. The mixture was cooled to RT and the solvent was removed in vacuo. The residue was dissolved in chloroform and filtered. The filtrate was concentrated in vacuo then disolved in CH$_2$Cl$_2$ and triturated with diethylether to give the title compound as a yellow solid (22 mg, 38%). $^1$H-NMR (400 MHz, CDCl$_3$) δ 8.87 (d, 1H, J=7.2 Hz), 8.30 (d, 1H, J=5.2 Hz), 8.24 (dd, 1H, J=4.4, 2.0 Hz), 7.03 (dd, 1H, J=9.0, 4.4 Hz), 6.81 (d, 1H, J=5.3 Hz), 5.43 (s, 1H), 3.10 (t, 2H, J=7.5 Hz), 2.79 (m, 1H), 1.79 (m, 2H), 1.45 (m, 2H), 0.92 (t, 3H, J=7.5 Hz), 0.81 (m, 2H), 0.58 (m, 2H); MS (ESI) (M+H)+ 309.

b) (2E)-1-(2-Butylpyrazolo[1,5-b]pyridazin-3-yl)-3-(dimethylamino)-2-propen-1-one. 1-(2-Methylpyrazolo[1,5-b]pyridazin-3-yl)ethanone (165 mg, 0.95 mmol) was added to DMF dimethylacetal (6.0 mL). The reaction was heated at an oil bath temperature of 120° C. for about 3 days. The solvent was removed in vacuo. The residue was triturated with diethylether to give the title compound as a brown solid (60 mg, 26%). The crude material was used without purification in the next step.

c) 1-(2-Butylpyrazolo[1,5-b]pyridazin-3-yl)ethanone. To a slurry of 1-aminopyridazinium iodide (1.60 g, 7.2 mmol) in DMSO (14.0 mL) was added 3-hexyne-2-one (1.57 mL, 14.4 mmol). The reaction flask was cooled in an ice bath at 4° C. then KOH (403 mg, 7.2 mmol) and K$_2$CO$_3$ (500 mg, 3.6 mmol) were added in one portion. The bath was removed and the mixture was stirred at RT for about 1 hour. Water was added (60 mL). The organic layer was separated and the aqueous layer was extracted with CH$_2$Cl$_2$ (3×50 mL). The combined organic layers were dried (MgSO$_4$), filtered and concentrated in vacuo. The residue was triturated with diethyl ether and EtOAc to give the title compound as a red solid (350 mg, 26%). $^1$H-NMR (300 MHz, CDCl$_3$) δ 8.65 (dd, 1H, J=9.0, 1.5 Hz), 8.42 (dd, 1H, J=4.4, 1.5 Hz), 7.29 (dd, 1H, J=9.0, 4.4 Hz), 3.18 (t, 2H, J=7.5 Hz), 2.65 (s, 3H), 1.88 (m, 2H), 1.54 (m, 2H), 1.02 (t, 3H, J=7.5 Hz); MS (APCI) (M+H)+ 218.

d) 3-Octyn-2-one. To a solution of hexyne (2.3 mL, 20.0 mmol) in THF (20.0 mL) at −78° C. was added nBuLi (8.0 mL, 20 mmol) in one portion. The reaction mixture was stirred for 10 minutes then dimethylacetamide (1.85 mL, 20 mmol) was added. The cooling bath was removed an the mixture was stirred at RT for about 1 hour. Water was added (100 mL) followed by the addition of diethylether (200 mL). The combined organic layers were dried (MgSO$_4$), filtered and concentrated in vacuo to give the title compound as an oil. The crude material was used without purification in the next step.

Example 33

N-[4-(4-Methyl-1-piperazinyl)phenyl]-4-(2-methylpyrazolo[1,5-b]pyridazin-3-yl)-2-pyrimidinamine

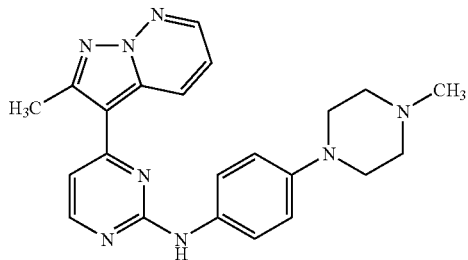

a) In a similar manner as described in Example 30a, from N-[4-(4-methyl-1-piperazinyl)phenyl]guanidine.HCl was obtained the title compound as a yellow solid. $^1$H-NMR (300 MHz, CDCl$_3$) □ 8.65 (dd, 1H, J=9.0, 1.8 Hz), 8.40 (d, 1H, J=5.2 Hz), 8.29 (dd, 1H, J=4.4, 2.0 Hz), 7.47 (d, 2H, J=8.9 Hz), 7.01 (dd, 1H, J=9.1, 4.6 Hz), 6.95 (m, 3H), 3.23 (m, 4H), 2.78 (s, 3H), 2.66 (m, 4H), 2.40 (s, 3H); MS (APCI) (M+H)+ 401.

Example 34

4-(2-Ethylpyrazolo[1,5-b]pyridazin-3-yl)-N-[4-(4-methyl-1-piperazinyl)phenyl]2-pyrimidinamine

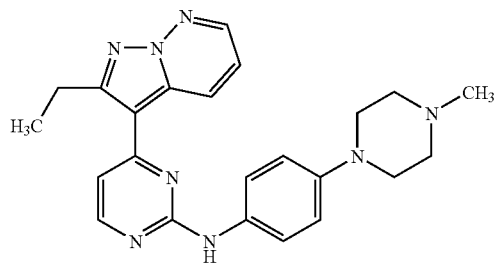

a) In a similar manner as described in Example 31a, from N-[4-(4-methyl-1-piperazinyl)phenyl]guanidine.HCl was obtained the title compound as a yellow solid. $^1$H-NMR (300 MHz, CDCl$_3$) □ 8.66 (dd, 1H, J=9.1, 1.9 Hz), 8.43 (d, 1H, J=5.2 Hz), 8.31 (dd, 1H, J=4.4, 1.9 Hz), 7.51 (d, 2H, J=8.9 Hz), 6.9-7.1 (m, 5H), 3.25 (m, 4H), 3.16 (q, 2H, J=7.5 Hz), 2.65 (m, 4H), 2.42 (s, 3H), 1.49 (t, 3H, J=7.5 Hz); MS (ESI) (M+H)+ 415.

Example 35

4-(2-Butylpyrazolo[1,5-b]pyridazin-3-yl)-N-[4-(4-methyl-1-piperazinyl)phenyl]-2-pyrimidinamine

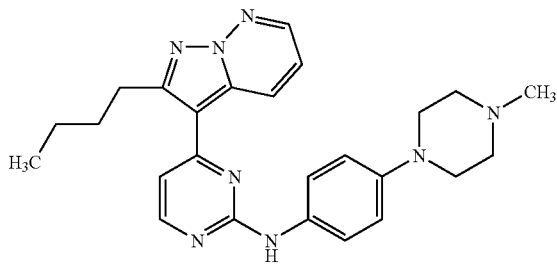

a) In a similar manner as described in Example 32a, from N-[4-(4-methyl-1-piperazinyl)phenyl]guanidine.HCl was obtained the title compound as a yellow solid. $^1$H-NMR (400 MHz, CDCl$_3$) δ 8.57 (dd, 1H, J=9.0, 1.9 Hz), 8.36 (d, 1H, J=5.3 Hz), 8.24 (dd, 1H, J=4.4, 2.0 Hz), 7.43 (d, 2H, J=8.9 Hz), 6.95 (dd, 1H, J=9.0, 4.4 Hz), 6.91 (d, 2H, J=8.9 Hz), 6.88 (d, 1H, J=5.2 Hz), 3.17 (m, 4H), 3.09 (t, 2H, J=7.5 Hz), 2.58 (m, 4H), 2.34 (s, 3H), 1.82 (m, 2H), 1.44 (m, 2H), 0.93 (t, 3H, J=7.5 Hz); MS (ESI) (M+H)$^+$ 443.

Example 36

N-Cyclopropyl-4-(6-methoxypyrazolo[1,5-b]pyridazin-3-yl)-2-pyrimidinamine

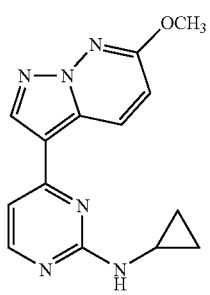

a) In a similar manner as described in Example 1a, from (2E)-3-(dimethylamino)-1-(6-methoxypyrazolo[1,5-b]pyridazin-3-yl)-2-propen-1-one was obtained the title compound as a brown solid. $^1$H-NMR (300 MHz, CDCl$_3$) δ 8.95 (d, 1H, J=9.5 Hz), 8.30 (d, 1H, J=5.1 Hz), 8.28 (s, 1H), 6.91 (d, 1H, J=5.2 Hz), 6.83 (d, 1H, J=9.4 Hz), 5.39 (s, 1H), 4.09 (s, 3H), 2.88 (m, 1H), 0.87 (m, 2H), 0.64 (m, 2H); MS (ESI) (M+H)$^+$ 283.

b) (2E)-3-(Dimethylamino)-1-(6-methoxypyrazolo[1,5-b]pyridazin-3-yl)-2-propen-1-one. In a similar manner as described in Example 30b, from 1-(6-methoxypyrazolo[1,5-b]pyridazin-3-yl)ethanone was obtained the title compound as a brown solid. $^1$H-NMR (300 MHz, d$^6$-DSMO) δ 8.53 (d, 1H, J=9.5 Hz), 8.47 (s, 1H), 7.63 (d, 1H, J=12.4 Hz), 7.06 (d, 1H, J=9.5 Hz), 5.76 (d, 1H, J=12.4 Hz), 3.96 (s, 3H), 3.10 (bs, 3H), 2.90 (bs, 3H); MS (ESI) (M+H)$^+$ 247.

c) 1-(6-Methoxypyrazolo[1,5-b]pyridazin-3-yl)ethanone. 3-Methoxypyridazine.HCl (16.6 g, 151 mmol) was added to pH 8.0 buffer (250 mL) and heated at 70° C. HOSA (25.6 g, 227 mmol) in water (10 mL) was neutralized to about pH 7.5 by the addition of aqueous KHCO$_3$ (110 mL, 2.4 M). The HOSA solution was added dropwise via addition funnel over one hour. The reaction was cooled to RT and CH$_2$Cl$_2$ (250 mL) was added. The reaction mixture was cooled in an ice bath and 3-butyne-2-one (5.3 mL, 75 mmol) was added in one portion followed by the dropwise addition of KOH (9.52 g, 169 mmol) in water (25 mL). The reaction mixture was allowed to warm to RT and stirred for about 2 hours. The aqueous layer was extracted with EtOAc (2×300 mL). The combined organic layers were washed with water (100 mL), dried (MgSO$_4$), and concentrated in vacuo. The residue was triturated with EtOAc and hexanes to give the title compound as a red solid (5.6 g, 39%). $^1$H-NMR (300 MHz, CDCl$_3$) δ 8.54 (d, 1H, J=9.5 Hz), 8.24 (s, 1H), 6.95 (d, 1H, J=9.5 Hz), 4.09 (s, 3H), 2.55 (s, 3H); MS (ESI) (M+H)$^+$ 192.

d) 3-Methoxypyridazine.HCl. To a solution of 3-chloro-6-methoxypyridazine (2.9 g, 20.0 mmol) in methanol (30 mL) was added Pd/C (145 mg, 10% w/w). Hydrogen gas was bubbled through the solution and then a balloon of hydrogen gas was left over the reaction for about 12 hours. The reaction was filtered through Celite and the filtrate collected and concentrated in vacuo. The oil was used without further purification. $^1$H-NMR (300 MHz, CDCl$_3$) δ 9.47 (d, 1H, J=5.0 Hz), 8.26 (dd, 1H, J=9.1, 4.8 Hz), 7.70 (d, 1H, J=8.9 Hz), 4.19 (s, 3H).

Example 37

4-(6-Methoxypyrazolo[1,5-b]pyridazin-3-yl)-N-[4-(4-methyl-1-piperazinyl)phenyl]-2-pyrimidinamine

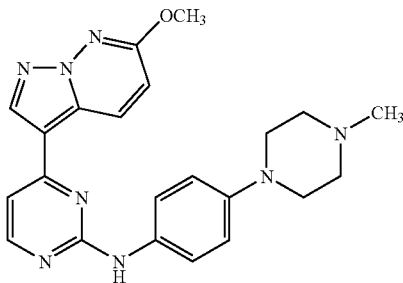

a) To a solution (2E)-3-(dimethylamino)-1-(6-methoxypyrazolo[1,5-b]pyridazin-3-yl)-2-propen-1-one (40 mg, 0.16 mmol) in DMF (2.0 mL) was added N-[4-(4-methyl-1-piperazinyl)phenyl]guanidine.HCl (99 mg, 0.32 mmol) and potassium carbonate (112 mg, 0.80 mmol). The reaction was heated at an oil bath temperature of 130° C. for about 18 hours. The mixture was cooled to RT and the solvent was removed in vacuo. The residue was dissolved in chloroform and filtered. The filtrate was concentrated in vacuo then disolved in CH$_2$Cl$_2$ and triturated with diethylether to give the title compound as a yellow solid (12 mg, 18%). $^1$H-NMR (400 MHz, CDCl$_3$) δ 8.67 (d, 1H, J=9.5 Hz), 8.35 (d, 1H, J=5.2 Hz), 8.29 (s, 1H), 7.46 (d, 2H, J=8.9 Hz), 6.98 (m, 3H), 6.90 (s, 1H), 6.75 (d, 1H, J=9.5 Hz), 4.09 (s, 3H), 3.23 (m, 4H), 2.64 (m, 4H), 2.39 (s, 3H); MS (ESI) (M+H)$^+$ 417.

Example 38

3-[2-(Cyclopropylamino)-4-pyrimidinyl]pyrazolo[1,5-b]pyridazin-6-ol

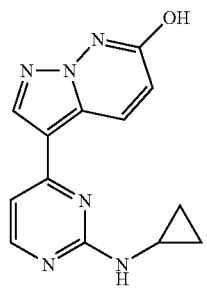

a) A solution of N-cyclopropyl-4-(6-methoxypyrazolo[1,5-b]pyridazin-3-yl)-2-pyrimidinamine (510 mg, 1.81 mmol) in morpholine (15 mL) was heated at an oil bath temperature of 130° C. for about 16 hours. The reaction mixture was cooled and the solvent removed in vacuo. The residue was disolved in $CH_2Cl_2$ and triturated with diethylether to give the title compound as a yellow solid (400 mg, 82%). $^1$H-NMR (300 MHz, d$^6$-DMSO) δ 8.96 (d, 1H, J=9.7 Hz), 8.49 (s, 1H), 8.23 (d, 1H, J=5.0 Hz), 7.35 (s, 1H), 7.06 (d, 1H, J=5.1 Hz), 6.97 (d, 1H, J=9.5 Hz), 2.74 (m, 1H), 0.73 (m, 2H), 0.49 (bs, 2H); MS (ESI) (M+H)$^+$ 269.

Example 39

N-Cyclopropyl-4-(6-isopropoxypyrazolo[1,5-b]pyridazin-3-yl)-2-pyrimidinamine

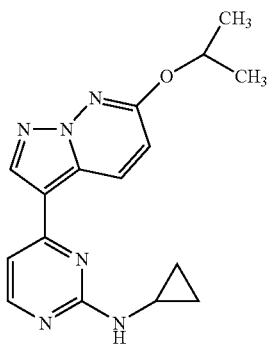

a) In a similar manner as described in Example 1a, from (2E)-3-(dimethylamino)-1-(6-isopropoxypyrazolo[1,5-b]pyridazin-3-yl)-2-propen-1-one was obtained the title compound as a brown solid. $^1$H-NMR (300 MHz, CDCl$_3$) δ 8.91 (d, 1H, J=9.5 Hz), 8.29 (d, 1H, J=5.2 Hz), 8.25 (s, 1H), 6.90 (d, 1H, J=5.3 Hz), 6.76 (d, 1H, J=9.7 Hz), 5.41 (septet, 1H, J=6.2 Hz), 5.35 (bs, 1H), 2.85 (m, 1H), 1.43 (d, 6H, J=6.2 Hz), 0.87 (m, 2H), 0.63 (m, 2H); MS (ESI) (M+H)$^+$ 311.

b) (2E)-3-(Dimethylamino)-1-(6-isopropoxypyrazolo[1,5-b]pyridazin-3-yl)-2-propen-1-one. In a similar manner as described in Example 30b, from 1-(6-isopropoxypyrazolo[1,5-b]pyridazin-3-yl)ethanone (150 mg, 0.7 mmol) was obtained the title compound as a brown solid. This material was used in the next step without further purification. MS (ESI) (M+H)$^+$ 275.

c) 1-(8-Isopropoxypyrazolo[1,5-b]pyridazin-3-yl)ethanone. To a solution of 1-(6-hydroxypyrazolo[1,5-b]pyridazin-3-yl)ethanone (200 mg, 1.13 mmol) in THF (8.0 mL) was added PPh$_3$ (445 mg, 1.70 mmol), DEAD (296 mg, 1.70 mmol) and iPrOH (0.432 mL, 5.65 mmol). The mixture was stirred at RT for about 14 hours. Water (20 mL) was added and the aqueous layer was washed with EtOAc (3×40 mL). The combined organic layers were dried (MgSO$_4$) and concentrated in vacuo to give the title compound as a white solid. This material was used in the next step without further purification. MS (ESI) (M+H)$^+$ 220.

d) 1-(6-Hydroxypyrazolo[1,5-b]pyridazin-3-yl)ethanone. To 1-(6-methoxypyrazolo[1,5-b]pyridazin-3-yl)ethanone (600 mg, 3.14 mmol) was added HI (10.0 mL, 57% in water). The reaction mixture was heated at an oil bath temperature of 90° C. for about 12 hours. The mixture was cooled to RT, the water layer was brought to pH 8.0 and washed with EtOAc (3×100 mL). The combined organic layers were dried (MgSO$_4$) and concentrated in vacuo to give the title compound as a yellow amorphous solid (365 mg, 63%). $^1$H-NMR (300 MHz, d$^6$-DMSO) δ 12.25 (bs, 1H), 8.48 (s, 1H), 8.43 (d, 1H, J=9.5 Hz), 7.07 (d, 1H, J=9.5 Hz), 2.47 (s, 3H); MS (ESI) (M+H)$^+$ 178.

Example 40

N-[4-(6-Isopropoxypyrazolo[1,5-b]pyridazin-3-yl)-2-pyrimidinyl]-N-[4-(4-methyl-1-piperazinyl)phenyl]amine

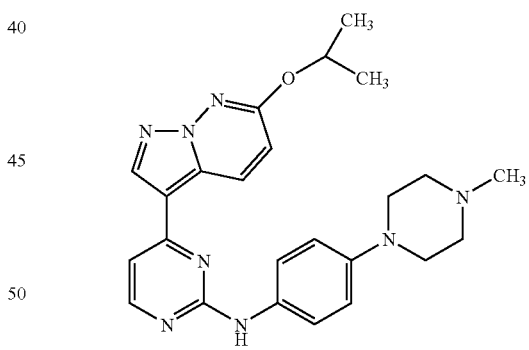

a) In a similar manner as described in Example 37a, from (2E)-3-(dimethylamino)-1-(6-isopropoxypyrazolo[1,5-b]pyridazin-3-yl)-2-propen-1-one was obtained the title compound as a brown solid. $^1$H-NMR (300 MHz, CDCl$_3$) δ 8.64 (d, 1H, J=9.6 Hz), 0.34 (d, 1H, J=5.2 Hz), 8.26 (s, 1H), 7.46 (d, 2H, J=8.8 Hz), 6.97 (m, 3H), 6.87 (s, 1H), 6.67 (d, 1H, J=9.6 Hz), 5.41 (m, 1H), 3.23 (m, 4H), 2.64 (m, 4H), 2.40 (s, 3H), 1.43 (d, 6H, J=6.1 Hz); MS (ESI) (M+H)$^+$ 445.

Example 41

3-[2-(Cyclopropylamino)-4-pyrimidinyl]pyrazolo[1,5-b]pyridazin-6-yl trifluoromethanesulfonate

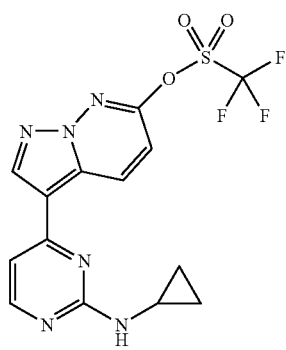

a) To a solution of 3-[2-(cyclopropylamino)-4-pyrimidinyl]pyrazolo[1,5-b]pyridazin-6-ol (10.0 g, 37.3 mmol) in DMF (100 mL) was added N-phenyltrifluoromethylsulfonimide (15.0 g, 42.0 mmol) and DIEA (13 mL, 80 mmol). The reaction mixture was stirred at RT for about 2 hours. Water (500 mL) was added and the aqueous layer was washed with EtOAc (3×1 L). The combined organic layers were dried (MgSO$_4$) and concentrated in vacuo to give the a yellow amorphous solid. The solid was dissolved in CH$_2$Cl$_2$ and purified by silica-gel column chromatography (gradient, 0-10% MeOH in CH$_2$Cl$_2$) to give the title compound as a white solid (7.4 g, 50%). $^1$H-NMR (300 MHz, CDCl$_3$) δ 9.36 (d, 1H, J=9.5 Hz), 8.54 (s, 1H), 8.35 (bs, 1H), 7.17 (d, 1H, J=9.4 Hz), 6.98 (d, 1H, J=5.3 Hz), 5.65 (bs, 1H), 2.85 (m, 1H), 0.90 (m, 2H), 0.67 (m, 2H); MS (ESI) (M+H)$^+$ 401.

Example 42

4-[6-(2-Chlorophenyl)pyrazolo[1,5-b]pyridazin-3-yl]-N-cyclopropyl-2-pyrimidinamine

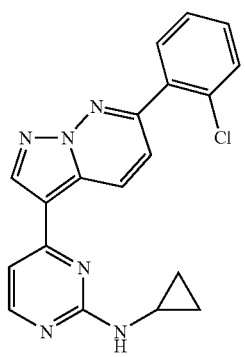

a) To a solution of 3-[2-(cyclopropylamino)-4-pyrimidinyl]pyrazolo[1,5-b]pyridazin-6-yl trifluoromethanesulfonate (21.0 mg, 0.08 mmol) in DMF (1 mL) was added Pd(PPh$_3$)$_2$Cl$_2$ (5 mg, 0.007 mmol), 2-chlorophenyl boronic acid (15 mg, 0.096 mmol), and Na$_2$CO$_3$ (21.0 mg in 0.5 mL water). The reaction mixture was heated at an oil bath temperature of 100° C. for about 12 hours. The mixture was cooled to RT and water (20 mL) was added. The aqueous layer was washed with EtOAc (3×50 mL). The combined organic layers were dried (MgSO$_4$) and concentrated in vacuo and purified by silica-gel column chromatography (30% EtOAc/hexanes) to give the title compound as a brown solid (15 mg, 55%). $^1$H-NMR (300 MHz, CDCl$_3$) δ 9.14 (d, 1H, J=9.2 Hz), 8.52 (s, 1H), 8.32 (d, 1H, J=5.3 Hz), 7.74-7.71 (m, 1H), 7.56-7.52 (m, 2H), 7.46-7.42 (m, 2H), 5.61 (bs, 1H), 2.88 (m, 1H), 0.89 (m, 2H), 0.66 (m, 2H); MS (ESI) (M+H)$^+$ 363.

Example 43

N-Cyclopropyl-4-[6-(2-thienyl)pyrazolo[1,5-b]pyridazin-3-yl]-2-pyrimidinamine

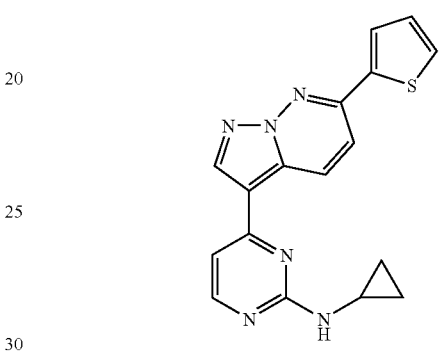

a) In a similar manner as described in Example 42a, from thiophene-2-boronic acid was obtained the title compound as a brown solid. $^1$H-NMR (300 MHz, CDCl$_3$) δ 9.09 (d, 1H, J=9.3 Hz), 8.8 (s, 1H), 8.20 (d, 1H, J=5.5 Hz), 7.76 (d, 1H, J=3.3 Hz), 7.63 (d, 1H, J=9.5 Hz), 7.54 (d, 1H, J=4.9 Hz), 7.19 (t, 1H, J=4.4 Hz), 6.99 (d, 1H, J=5.8 Hz), 2.91 (m, 1H), 0.95 (m, 2H), 0.74 (m, 2H); MS (ESI) (M+H)$^+$ 335.

Example 44

N-Cyclopropyl-4-[6-(4-fluorophenyl)pyrazolo[1,5-b]pyridazin-3-yl]-2-pyrimidinamine

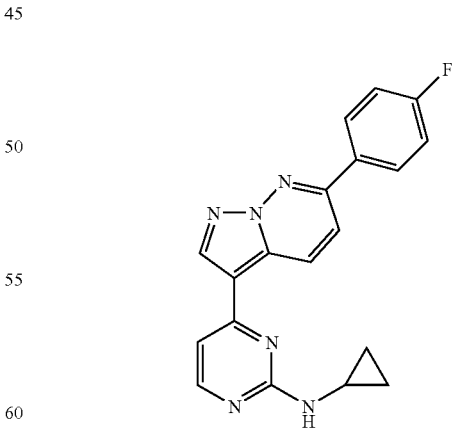

a) In a similar manner as described in Example 42a, from 4-fluorophenyl boronic acid was obtained the title compound as a brown solid. $^1$H-NMR (300 MHz, CDCl$_3$) δ 9.16 (d, 1H, J=9.3 Hz), 8.48 (s, 1H), 8.33 (d, 1H, J=4.6 Hz), 8.09 (dd, 2H, J=8.8, 5.2 Hz), 7.60 (d, 1H, J=9.3 Hz), 7.22 (t, 2H, J=8.6 Hz), 6.96 (d, 1H, J=5.2 Hz), 5.47 (bs, 1H), 2.88 (m, 1H), 0.90 (m, 2H), 0.67 (m, 2H); MS (APCI) (M+H)+ 347.

Example 45

N-Cyclopropyl-4-(6-vinylpyrazolo[1,5-b]pyridazin-3-yl)-2-pyrimidinamine

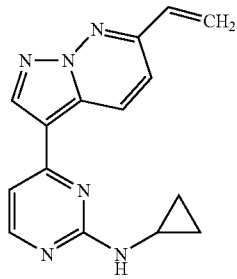

a) To a solution of 3-[2-(cyclopropylamino)-4-pyrimidinyl]pyrazolo[1,5-b]pyridazin-6-yl trifluoromethanesulfonate (100 mg, 0.25 mmol) in DMF (3 mL) was added Pd$_2$(dba)$_3$ (12 mg, 0.0125 mmol), LiCl (32 mg, 0.75 mmol), AsPh$_3$ (31 mg, 0.10 mmol), and vinyl-tributylstannane (120 mg, 0.375 mmol). The reaction mixture was heated at an oil bath temperature of 60° C. for about 4 hours. The mixture was cooled to RT and water (20 mL) was added. The aqueous layer was washed with EtOAc (3×50 mL). The combined organic layers were dried (MgSO$_4$) and concentrated in vacuo and purified by silica-gel column chromatography (gradient, 10-80% EtOAc in hexanes) to give the title compound as an off-white solid (26 mg, 37%). $^1$H-NMR (300 MHz, CDCl$_3$) δ 9.05 (d, 1H, J=9.3 Hz), 8.44 (s, 1H), 8.30 (d, 1H, J=5.3 Hz), 7.40 (d, 1H, J=9.4 Hz), 6.92 (m, 2H), 6.22 (d, 1H, J=17.7 Hz), 5.75 (d, 1H, J=11.2 Hz), 5.48 (bs, 1H), 2.86 (m, 1H), 0.90 (m, 2H), 0.66 (m, 2H); MS (ESI) (M+H)+ 279.

Example 46

N-Cyclopropyl-4-[6-(4-morpholinyl)pyrazolo[1,5-b]pyridazin-3-yl]-2-pyrimidinamine

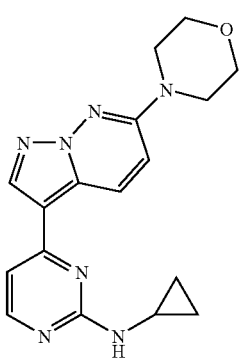

a) This product is isolated by silica-gel column chromatography from Example 41a.
$^1$H-NMR (300 MHz, d$^6$-DMSO) δ 8.88 (d, 1H, J=9.8 Hz), 8.47 (s, 1H), 8.22 (d, 1H, J=5.0 Hz), 7.37 (m, 2H), 7.04 (d, 1H, J=5.2 Hz), 3.73 (t, 4H, J=4.6 Hz), 3.49 (t, 4H, J=4.7 Hz), 2.74 (m, 1H), 0.73 (m, 2H), 0.50 (m, 2H); MS (ESI) (M+H)+ 338.

Example 47

N-Cyclopentyl-3-[2-(cyclopropylamino)-4-pyrimidinyl]pyrazolo[1,5-b]pyridazin-6-amine

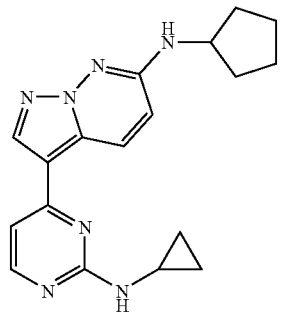

a) To a solution of 3-[2-(cyclopropylamino)-pyrimidinyl]pyrazolo[1,5-b]pyridazin-6-yl trifluoromethanesulfonate (107 mg, 0.268 mmol) in DMF (2 mL) was added DIEA (0.093 mL, 0.536 mmol) and cyclopentylamine (0.026 mL, 0.268 mmol). The reaction mixture was heated at an oil bath temperature of 50° C. for about 1 hour at which point N-phenyltrifluoromethylsulfonimide (95 mg, 0.268 mmol) was added followed by an additional portion (equivalent) of cyclopentylamine and DIEA. This was repeated two more times. The mixture was cooled to RT and water (20 mL) was added. The aqueous layer was washed with EtOAc (3×50 mL). The combined organic layers were dried (MgSO$_4$) and concentrated in vacuo and purified by silica-gel column chromatography (gradient, 0-10% MeOH in CH$_2$Cl$_2$). The residue was suspended in EtOAc and triturated with hexanes to give the title compound as a yellow solid (26 mg, 29%). $^1$H-NMR (300 MHz, CDCl$_3$) δ 8.71 (d, 1H, J=9.5 Hz), 8.17 (s, 2H), 6.89 (d, 1H, J=5.7 Hz), 6.55 (d, 1H, J=9.3 Hz), 5.92 (bs, 1H), 4.43 (m, 1H), 4.30 (m, 1H), 2.84 (m, 1H), 2.16 (m, 2H), 1.71 (m, 4H), 1.50 (m, 2H), 0.87 (m, 2H), 0.66 (m, 2H); MS (APCI) (M+H)+ 336.

Example 48

N-Cyclopropyl-4-[6-(1-pyrrolidinyl)pyrazolo[1,5-b]pyridazin-3-yl]-2-pyrimidinamine

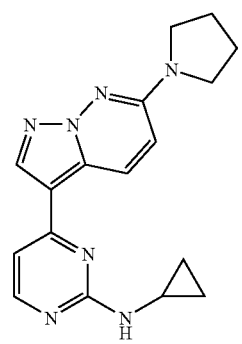

a) In a similar manner as described in Example 47a, from pyrrolidine was obtained the title compound as a yellow solid. $^1$H-NMR (300 MHz, CDCl$_3$) δ 8.83 (d, 1H, J=9.5 Hz), 8.29 (d, 1H, J=5.4 Hz), 8.20 (s, 1H), 6.92 (d, 1H, J=5.4 Hz), 6.74

(d, 1H, J=9.6 Hz), 5.36 (s, 1H), 3.60 (m, 4H), 2.88 (m, 1H), 2.09 (m, 4H), 0.90 (m, 2H), 0.67 (m, 2H); MS (ESI) (M+H)+ 322.

Example 49

N-Cyclopropyl-4-[6-(2-fluoro-4-pyridinyl)pyrazolo[1,5-b]pyridazin-3-yl]-2-pyrimidinamine

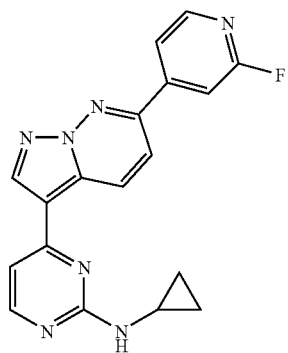

a) In a similar manner as described in Example 42a, from 2-fluoropyridyl-4-boronic acid was obtained the title compound as a brown solid. $^1$H-NMR (400 MHz, CDCl$_3$) δ 9.29 (bs, 1H), 8.56 (s, 1H), 8.42 (d, 1H, J=5.3 Hz), 8.37 (dd, 1H, J=9.5, 5.0 Hz), 7.90 (d, 1H, J=5.1 Hz), 7.63 (m, 2H), 6.98 (d, 1H, J=5.1 Hz), 5.41 (s, 1H), 2.88 (m, 1H), 0.91 (m, 2H), 0.67 (m, 2H); MS (ESI) (M+H)+ 348.

Example 50

N-Cyclopropyl-4-[6-(phenylsulfanyl)pyrazolo[1,5-b]pyridazin-3-yl]-2-pyrimidinamine

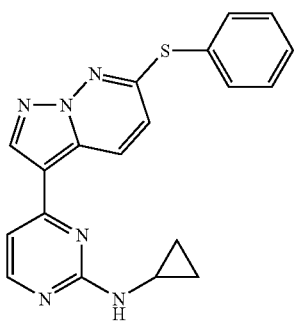

a) To a solution of 3-[2-(cyclopropylamino)-4-pyrimidinyl]pyrazolo[1,5-b]pyridazin-6-yl trifluoromethanesulfonate (250 mg, 0.625 mmol) in DMSO (8 mL) was added Pd(PPh$_3$)$_4$ (29 mg, 0.025 mmol), benzene thiol (0.064 mL, 0.625 mmol), and NaOtBu (120 mg, 1.31 mmol). The reaction mixture was heated at an oil bath temperature of 100° C. for about 2 hours. The mixture was cooled to RT and water (40 mL) was added. The aqueous layer was washed with EtOAc (3×60 mL). The combined organic layers were dried (MgSO$_4$) and concentrated in vacuo and purified by silica-gel column chromatography (gradient 50-100% EtOAc in hexanes) to give the title compound as a yellow solid (80 mg, 36%). $^1$H-NMR (400 MHz, CDCl$_3$) δ 8.90 (d, 1H, J=9.1 Hz), 8.34 (s, 1H), 8.29 (bs, 1H), 7.67 (m, 2H), 7.47 (m, 3H), 6.92 (d, 1H, J=5.3 Hz), 6.88 (d, 1H, J=9.4 Hz), 5.38 (s, 1H), 2.82 (m, 1H), 0.85 (m, 2H), 0.61 (m, 2H); MS (ESI) (M+H)+ 361.

Example 51

4-[6-(4-Fluorophenyl)pyrazolo[1,5-b]pyridazin-3-yl]-N-(4-methoxyphenyl)-2-pyrimidinamine

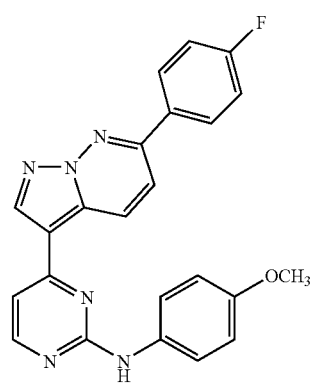

a) To a solution of 6-(4-fluorophenyl)-3-[2-(methylthio)pyrimidin-4-yl]pyrazolo[1,5-b]pyridazine (42 mg, 0.124 mmol) in MeOH (2 mL) was added Oxone (77 mg, 0.124 mmol) in water (1 mL). The reaction mixture was stirred for about 2 hours then water (10 mL) was added. The aqueous layer was washed with EtOAc (3×40 mL) and aqueous NaHCO$_3$ (1×20 mL). The combined organic layers were dried (MgSO$_4$) and concentrated in vacuo to give a brown solid. This solid was added to iPrOH (1.0 mL) and 4-methoxyaniline (20 mg, 0.162 mmol) in a sealed tube. The reaction mixture was heated at an oil bath temperature of 130° C. for about 16 hours. The mixture was cooled to RT and the solid collected by filtration to give the title compound as a brown solid (17 mg, 33%). $^1$H-NMR (300 MHz, d$^6$-DMSO) δ 9.41 (s, 1H), 9.14 (d, 1H, J=9.1 Hz), 8.88 (s, 1H), 8.41 (d, 1H, J=5.1 Hz), 8.22 (dd, 2H, J=8.5, 5.6 Hz), 8.02 (d, 1H, J=9.3 Hz), 7.62 (d, 2H, J=8.8 Hz), 7.42 (t, 2H, J=8.8 Hz), 7.30 (d, 1H, J=5.2 Hz), 6.94 (d, 2H, J=8.8 Hz), 3.75 (s, 3H); MS (ESI) (M+H)+ 413.

b) 6-(4-Fluorophenyl)-3-[2-(methylthio)pyrimidin-4-yl]pyrazolo[1,5-b]pyridazine. In a similar manner as described in Example 44a, from 3-[2-(methylthio)pyrimidin-4-yl]pyrazolo[1,5-b]pyridazin-6-yl trifluoromethanesulfonate was obtained the title compound as a brown solid. $^1$H-NMR (300 MHz, CDCl$_3$) δ 9.02 (d, 1H, J=9.3 Hz), 8.54 (m, 2H), 8.10 (m, 2H), 7.69 (d, 1H, J=9.4 Hz), 7.31 (d, 1H, J=5.4 Hz), 7.21 (m, 2H), 2.71 (s, 3H); MS (ESI) (M+H)+ 338.

c) 3-[2-(Methylthio)pyrimidin-4-yl]pyrazolo[1,5-b]pyridazin-6-yl trifluoromethanesulfonate. In a similar manner as described in Example 41a, from 3-[2-(methylthio)pyrimidin-4-yl]pyrazolo[1,5-b]pyridazin-6-ol was obtained the title compound as a brown solid. $^1$H-NMR (300 MHz, DMSO d$^6$) δ 8.62 (d, 1H, J=9.9 Hz), 8.62 (s, 1H), 8.52 (d, 1H, J=5.4 Hz), 7.60 (d, 1H, J=5.4 Hz), 7.46 (d, 1H, J=9.9 Hz), 2.58 (s, 3H); MS (ESI) (M+H)+ 392.

d) 3-[2-(Methylthio)pyrimidin-4-yl]pyrazolo[1,5-b]pyridazin-6-ol. In a similar manner as described in Example 38a, from 6-methoxy-3-[2-(methylthio)pyrimidin-4-yl]

pyrazolo[1,5-b]pyridazine was obtained the title compound as a brown solid. $^1$H-NMR (300 MHz, DMSO d$^6$) δ 8.57 (d, 1H, J=9.6 Hz), 8.53 (s, 1H), 8.49 (d, 1H, J=5.5 Hz), 7.57 (d, 1H, J=5.5 Hz), 6.91 (d, 1H, J=9.6 Hz), 2.57 (s, 3H); MS (ESI) (M+H)$^+$ 260.

e) 6-Methoxy-3-[2-(methylthio)pyrimidin-4-yl]pyrazolo[1,5-b]pyridazine. In a similar manner as described in Example 36c, from 4-ethynyl-2-(methylthio)pyrimidine was obtained the title compound as a brown-solid. $^1$H-NMR (300 MHz, CDCl$_3$) δ 8.79 (d, 1H, J=9.6 Hz), 8.45 (d, 1H, J=5.3 Hz), 8.30 (s, 1H), 7.21 (d, 1H, J=5.4 Hz), 6.88 (d, 1H, J=9.4 Hz), 4.08 (s, 3H), 2.63 (s, 3H); MS (APCI) (M+H)$^+$ 274.

f) 4-Ethynyl-2-(methylthio)pyrimidine. To a solution of 4-iodo-2-(methylthio)pyrimidine (9.0 g, 35.7 mmol) in DMF (150 mL) was added TMS-acetylene (7.0 g, 71.43 mmol), TEA (15 mL, 107 mmol), CuI (0.70 g, 3.57 mmol), and Pd(PPh$_3$)$_2$Cl$_2$ (1.25 g, 1.79 mmol). The reaction mixture was heated at an oil bath temperature of 50° C. for about 1 hour. The mixture was cooled to RT and water (40 mL) was added. The aqueous layer was washed with EtOAc (3×60 mL). The combined organic layers were dried (MgSO$_4$) and concentrated in vacuo and purified by silica-gel column chromatography (gradient 10-40% EtOAc in hexanes) to give a yellow oil. The oil was dissolved in MeOH (20 mL) and cooled to 4° C. followed by addition of KF (2.0 g, 35 mmol). The mixture was stirred for about 5 minutes and poured onto a pad of silica-gel. The pad was washed with 50% EtOAc in hexanes. The fractions containing product were concentrated in vacuo to give the title compound as a yellow solid (4.0 g, 75%). $^1$H-NMR (300 MHz, CDCl$_3$) δ 8.51 (d, 1H, J=5.0 Hz), 7.07 (d, 1H, J=5.0 Hz), 3.34 (s, 1H), 2.57 (s, 3H); MS (ESI) (M+H)$^+$ 151.

g) 4-Iodo-2-(methylthio)pyrimidine. 4-Chloro-2-(methylthio)pyrimidine (24.5 g, 153 mmol) was added slowly to HI (100 mL, 30% in H$_2$O). The reaction was stirred at RT for about 14 hours. The mixture was neutralized with aqueous NaHCO$_3$. The solid was collected by filtration and dried under vacuum to give the title compound as a white solid (35 g, 91%).

Example 52

4-[6-(4-Fluorophenyl)pyrazolo[1,5-b]pyridazin-3-yl]-N-[4-(4-methyl-1-piperazinyl)phenyl]-2-pyrimidinamine

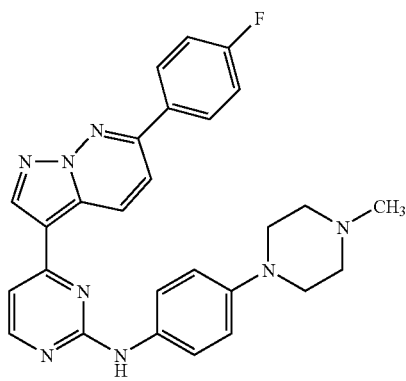

a) In a similar manner as described in Example 51a, from 4-(4-methylpiperazin-1-yl)aniline was obtained the title compound as a brown solid. $^1$H-NMR (400 MHz, CDCl$_3$) δ 8.88 (d, 1H, J=9.3 Hz), 8.48 (s, 1H), 8.38 (d, 1H, J=5.1 Hz), 8.07 (dd, 2H, J=8.8, 5.3 Hz), 7.50 (t, 3H, J=8.4 Hz), 7.22 (t, 2H, J=8.7 Hz), 7.02-6.98 (m, 3H), 6.94 (s, 1H), 3.23 (t, 4H, J=4.9 Hz), 2.63 (m, 4H), 2.38 (s, 3H); MS (ESI) (M+H)$^+$ 481.

Example 53

N$^1$,N$^1$-Dimethyl-N$^4$-{4-[6-(4-morpholinyl)pyrazolo[1,5-b]pyridazin-3-yl]-2-pyrimidinyl}-1,4-benzenediamine

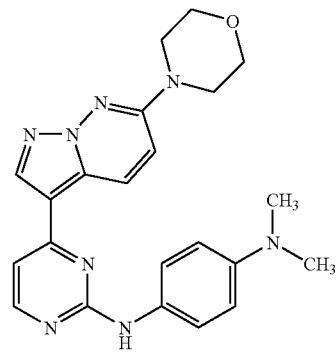

a) To a solution 3-[2-(methylthio)pyrimidinyl-4-yl]-6-morpholin-4-ylpyrazolo[1,5-b]pyridazine (116 mg, 0.354 mmol) in MeOH (10 mL) was added Oxone (456 mg, 0.741 mmol) in water (4 mL). The reaction mixture was stirred for about 2 hours then water (20 mL) was added. The aqueous layer was washed with EtOAc (3×80 mL) and aqueous NaHCO$_3$ (1×30 mL). The combined organic layers were dried (MgSO$_4$) and concentrated in vacuo to give a brown solid. This solid was added to iPrOH (2.0 mL) and N,N-dimethylbenzene-1,4-diamine (72 mg, 0.53 mmol) in a sealed tube. The reaction mixture was heated at an oil bath temperature of 130° C. for about 16 hours. The mixture was cooled to RT and the solid collected by filtration to give the title compound as a brown solid (18.6 mg, 13%). $^1$H-NMR (300 MHz, CDCl$_3$) δ 8.65 (d, 1H, J=9.8 Hz), 8.35 (d, 1H, J=5.4 Hz), 8.27 (s, 1H), 7.46 (d, 2H, J=8.9 Hz), 6.97 (d, 1H, J=5.2 Hz), 6.88-6.82 (m, 4H), 3.90 (t, 4H, J=4.8 Hz), 3.61 (t, 4H, J=4.9 Hz), 3.01 (s, 6H); MS (ESI) (M+H)$^+$ 417.

b) 3-[2-(Methylthio)pyrimidin-4-yl]-6-morpholin-4ylpyrazolo[1,5-b]pyridazine. To a solution of 3-[2-(methylthio)pyrimidin-4-yl]pyrazolo[1,5-b]pyridazin-6-yl trifluoromethanesulfonate (165 mg, 0.635 mmol) in DMF (2 mL) was added morpholine (60 mg, 0.697 mmol). The reaction was stirred for about 12 hours then water (40 mL) was added. The aqueous layer was washed with EtOAc (3×60 mL). The combined organic layers were dried (MgSO$_4$) and concentrated in vacuo and purified by trituration with EtOAc/hexanes to give the title compound as a white solid (85 mg, 41%).

Example 54

1-(Dimethylamino)-3-[4-({4-[6-(4-morpholinyl) pyrazolo[1,5-b]pyridazin-3-yl]-2-pyrimidinyl}amino)phenoxy]-2-propanol

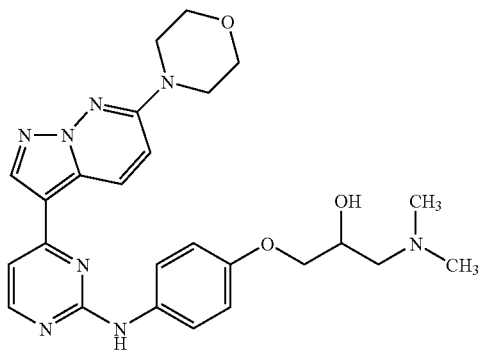

a) In a similar manner as described in Example 53a, from 1-(4-aminophenoxy)-3-(dimethylamino)propan-2-ol was obtained the title compound as a brown solid. $^1$H-NMR (400 MHz, d$^6$-DMSO) δ 9.31 (s, 1H), 8.78 (bd, 1H, J=9.1 Hz), 8.52 (s, 1H), 8.34 (d, 1H, J=5.3 Hz), 7.58 (d, 2H, J=9.0 Hz), 7.35 (d, 1H, J=9.9 Hz), 7.19 (d, 1H, J=5.3 Hz), 6.91 (d, 2H, J=9.0 Hz), 4.81 (d, 1H, J=4.4 Hz), 3.94-3.80 (m, 3H), 3.74 (t, 4H, J=4.8 Hz), 3.50 (t, 4H, J=4.7 Hz), 2.38 (dd, 1H, J=12.3, 5.6 Hz), 2.27 (dd, 1H, J=12.4, 6.5 Hz); MS (ESI) (M+H)$^+$ 491.

Example 55

N-(1,3-benzodioxol-5-yl)-4-pyrazolo[1,5-b]pyridazin-3-yl-2-pyrimidinamine

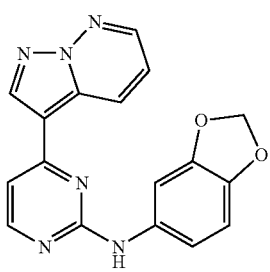

In a similar manner as described in Example 51, from 1,3-benzodioxolan-6-amine was obtained the title compound. $^1$H-NMR (300 MHz, d$^6$-DMSO) δ 9.47 (s, 1H), 9.17 (d, 1H, J=9.1 Hz), 8.90 (s, 1H), 8.64 (d, 1H, J=1.8 Hz), 8.46 (d, 1H, J=5.3 Hz), 7.46 (m, 2H), 7.36 (d, 1H, J=5.2 Hz), 7.15 (d, 1H, J=8.6 Hz), 6.93 (d, 1H, J=8.4 Hz), 6.02 (s, 2H); MS (ESI) (M+H)$^+$ 333.

Example 56

N-(2,3-Dihydro-1,4-benzodioxin-6-yl)-4-pyrazolo[1,5-b]pyridazin-3-yl-2-pyrimidinamine

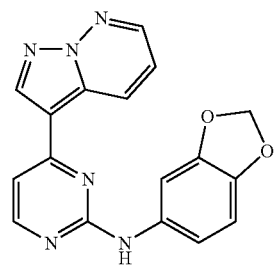

In a similar manner as described in Example 51, from 1,4-benzodioxan-6-amine was obtained the title compound. $^1$H-NMR (300 MHz, d$^6$-DMSO) δ 9.52 (s, 1H), 9.20 (d, 1H, J=9.6 Hz), 8.92 (s, 1H), 8.64 (s 1H), 8.49 (d, 1H, J=5.1 Hz), 7.57 (s, 1H), 7.51 (m, 1H), 7.39 (d, 1H, J=5.2 Hz), 7.27 (d, 1H, J=8.2 Hz), 6.99 (d, 1H, 8.7 Hz), 4.17 (m, 2H), 2.12 (m, 2H); MS (ESI) (M+H)$^+$ 347.

Example 57

N-[3-Methoxy-5-(trifluoromethyl)phenyl]-pyrazolo[1,5-b]pyridazin-3-yl-2-pyrimidinamine

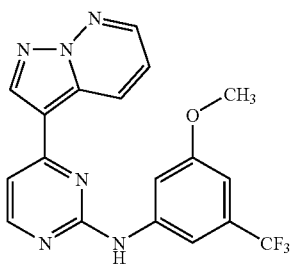

a) In a similar manner as described in Example 1a, from N-(3-methoxy-(5-trifluoromethyl)phenyl)guanidine nitrate was obtained the title compound. $^1$H-NMR (300 MHz, d$^6$-DMSO) δ 9.89 (s, 1H), 9.14 (d, 1H, J=8.8 Hz), 8.90 (s, 1H), 8.62 (s 1H), 8.53 (d, 1H, J=5.2 Hz), 7.82 (s, 1H), 7.65 (s, 1H), 7.45 (m, 2H), 6.83 (s, 1H), 3.31 (s, 3H) MS (ESI) (M+H)$^+$ 388.

b) N-(3-Methoxy-(5-trifluoromethyl)phenyl)guanidine nitrate

In a similar manner as described in Example 7b, from 3-methoxy-(5-trifluoromethyl)phenylguanidine nitrate was obtained the title compound. $^1$H-NMR (300 MHz, d$^6$-DMSO) δ 9.75 (s, 1H), 7.54 (br s, 3H), 7.49-7.09 (m, 3H), 3.83 (s, 3H); MS (ESI) (M+H)$^+$ 234.

Example 58

4-[(4-Pyrazolo[1,5-b]pyridazin-3-yl-2-pyrimidinyl)amino]benzonitrile

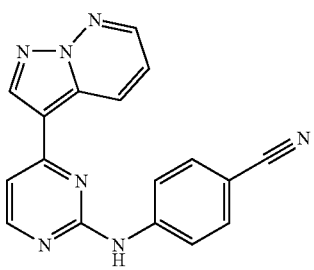

a) In a similar manner as described in Example 1a, from N-(4-cyanophenyl)guanidine nitrate was obtained the title compound. ¹H-NMR (300 MHz, d⁶-DMSO) δ 10.09 (s, 1H), 9.15 (d, 1H, J=8.6 Hz), 8.91 (s, 1H), 8.61 (s 1H), 8.54 (d, 1H, J=4.7 Hz), 7.97 (d, 2H, J=8.1 Hz), 7.76 (d, 2H, J=8.2 Hz), 7.48 (s, 2H); MS (ESI) (M+H)⁺ 314.

b) N-(4-Cyanophenyl)guanidine nitrate

In a similar manner as described in Example 7b, from 4-aminobenzonitrile was obtained the title compound. ¹H-NMR (300 MHz, d⁶-DMSO) δ 10.0 (s, 1H), 7.87 (d, 2H, J=9.3 Hz), 7.73 (br s, 3H), (d, 2H, J=8.5 Hz); MS (ESI) (M+H)⁺ 161.

Example 59

N-(4-Nitrophenyl)-4-pyrazolo[1,5-b]pyridazin-3-yl-2-pyrimidinamine

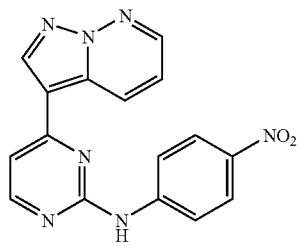

In a similar manner as described in Example 1a, from N-(4-nitrophenyl)guanidine nitrate was obtained the title compound. ¹H-NMR (300 MHz, d⁶-DMSO) δ 10.32 (s, 1H), 9.17 (d, 1H, J=9.0 Hz), 8.91 (s, 1H), 8.62 (d 1H, J=4.0 Hz), 8.57 (d, 1H, J=5.3 Hz), 8.22 (d, 2H, J=8.9 Hz), 8.02 (d, 2H, J=9.0 Hz), 7.52 (m, 2H); MS (ESI) (M+H)⁺ 334.

Example 60

N-(3-Methoxyphenyl)-4-pyrazolo[1,5-b]pyridazin-3-yl-2-pyrimidinamine

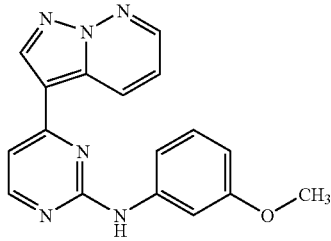

In a similar manner as described in Example 51a, from 3-methoxyaniline was obtained the title compound. ¹H-NMR (300 MHz, d⁶-DMSO) δ 9.56 (s, 1H), 9.21 (d, 1H, J=9.1 Hz), 8.89 (s, 1H), 8.62 (m, 1H), 8.49 (d, 1H, J=5.3 Hz), 7.47-7.20 (m, 6H), 3.75 (s, 3H); MS (ESI) (M+H)⁺ 319.

Example 61

N-(3,5-Dimethylphenyl)-4-pyrazolo[1,5-b]pyridazin-3-yl-2-pyrimidinamine

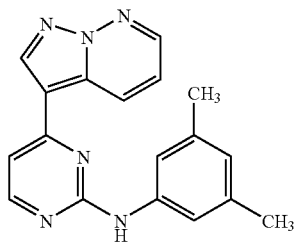

a) In a similar manner as described in Example 1a, from N-(3,5-dimethylphenyl)guanidine nitrate was obtained the title compound. ¹H-NMR (300 MHz, d⁶-DMSO) δ 9.47 (s, 1H), 9.18 (d, 1H, J=8.8 Hz), 8.92 (s, 1H), 8.62 (m, 1H), 8.50 (d, 1H, J=5.1 Hz), 7.48-7.37 (m, 4H), 6.67 (s, 1H), 2.29 (s, 6H); MS (ESI) (M+H)⁺ 317.

b) N-(3,5-Dimethylphenyl)guanidine nitrate

In a similar manner as described in Example 7b, from 3,5-dimethylaniline was obtained the title compound.

Example 62

4-[2-(4-methoxyphenyl)pyrazolo[1,5-b]pyridazin-3-yl]-N-phenylpyrimidin-2-amine

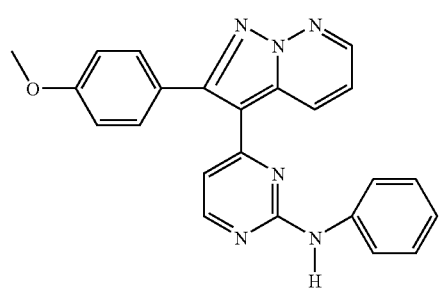

To a solution of 100 mg (0.31 mmol) of (2E)-3-(dimethylamino)-1-[2-(4-methoxyphenyl)pyrazolo[1,5-b]pyridazin-3-yl]prop-2-en-1-one in 5 ml of N,N-dimethylformamide were added 103 mg (0.39 mmol) of N-phenylguanidinium nitrate and 153 mg (1.11 mmol) of potassium carbonate. The mixture was stirred at 120° C. for 28 hours. Removal of solvent followed by column chromatography with dichloromethane:methanol=100:1 gave the crude product. The crude product was washed with dichloromethane to afford the desired compound in 30% yield.

$^1$H-NMR(400 MHz, DMSO-d$_6$) ppm: 9.6 (s, 1H), 8.86 (d J=8.9 Hz, 1H), 8.57 (m, 1H), 8.30 (d J=5.2 Hz, 1H), 7.67 (d J=8.0 Hz, 2H), 7.55 (d J=8.6 Hz, 2H), 7.39 (m, 1H), 7.23 (dd J=8.0 Hz, 2H), 7.05 ((d J=8.6 Hz, 2H), 6.92 (dd J=7.3 Hz, 1H), 6.56 (d J=5.2 Hz, 1H), 3.80 (s, 3H).

ES-MS: 395 (M+1). ES-HRMS for C$_{23}$H$_{19}$N$_6$O: Found 395.1608. Calcd 395.1620. Elemental Analysis for C$_{23}$H$_{18}$N$_6$O.1.12H$_2$O: Found C, 66.64; H, 4.66; N, 20.12. Calcd C, 66.63; H, 4.92; N, 20.27.

b) (2E)-3-(dimethylamino)-1-[2-(4-methoxyphenyl)pyrazolo[1,5-b]pyridazin-3-yl]prop-2-en-1-one 1.4 g (5.2 mmol) of 1-[2-(4-methoxyphenyl)pyrazolo[1,5-b]pyridazin-3-yl]ethanone was mixed with 8.4 ml (31.6 mmol) of N,N-dimethylformamide di-tert-butyl acetal in 15 ml of N,N-dimethylformamide. The mixture was heated at 110° C. for 2.5 hours. Solvent was removed under vacuum, ether was added and the mixture was kept at 4° C. overnight. Filtration gave 1.1 g of product as a solid in 65% yield.

$^1$H-NMR(300 MHz, DMSO-d$_6$) ppm: 8.53 (m, 2H), 7.68 (d J=8.2 Hz, 2H), 7.57 (d J=12.5 Hz, 1H), 7.38 (m, 1H), 7.08 (d J=8.2 Hz, 2H), 5.14 (d J=12.5 Hz, 1H), 3.84 (s, 3H), 3.06 (br, 3H), 2.57 (br, 3H). ES-MS: 322 (M).

c) 1-[2-(4-methoxyphenyl)pyrazolo[1,5-b]pyridazin-3-yl]ethanone

To a solution of 1.33 ml (18.3 mmol) of pyridazine in 90 ml of Hydrion buffer(pH=8) was added a solution of 3.1 g (27.4 mmol) of hydroxylamine-O-sulfonic acid neutralized with 2.5M potassium bicarbonate at 70° C. The reaction was stirred at 70° C. for 3 hours followed by cooling to 0° C. To the cooled reaction, 1.6 g (9.2 mmol) of 4-(4-methoxyphenyl)but-3-yn-2-one in 200 ml of dichloromethane and 1.51 g (22.9 mmol) of potassium hydroxide were added. The reaction was then stirred at room temperature overnight. The reaction was extracted with dichloromethane (3 times) and the combined dichloromethane layer was washed with brine (3 times) and then dried over magnesium sulfate. Removal of solvent under vacuum, and purification by column chromatography with hexane:ethyl acetate=4:1 gave 1.4 g of product as a solid in 57% yield.

$^1$H-NMR(300 MHz, DMSO-d$_6$) ppm: 8.7 (m, 2H), 7.6 (d J=8.5 Hz, 2H), 7.58 (m, 1H), 7.1 (d J=8.5 Hz, 2H), 3.87 (s, 3H), 2.24 (s, 3H). ES-MS: 268 (M+1).

d) 4-(4-methoxyphenyl)but-3-yn-2-one

To a solution of 5 g (37.9 mmol) of 1-Ethynyl-4-methoxybenzene in 100 ml of tetrahydrofuran was added 28.4 ml (45.4 mmol) of 1.6M n-Butyllithium at −78° C. The reaction was warmed gradually from −78° C. to room temperature over a period of 2 hours. The reaction was then cooled back to −78° C. and 5.8 ml (45.7 mmol) of boron trifluoride etherate was added, after 5 mins., 4.7 ml (49.8 mmol) of acetic anhydride was added. The reaction was warmed gradually from −78° C. to room temperature over a period of 2 hours. To the reaction mixture 1N sodium hydroxide was added until the solution was neutral. The mixture was extracted with ether (3 times) and the combined ether extracts were washed with brine (3 times) and dried over magnesium sulfate. The removal of solvent under vacuum followed by purification by column chromatography with hexane:ethyl acetate=20:1 as eluant gave 1.6 g of product as a liquid in 24% yield.

$^1$H-NMR(300 MHz, CDCl$_3$) ppm: 7.56 (d J=8.8 Hz, 2H), 6.93 (d J=8.8 Hz, 2H), 3.88 (s, 3H), 2.47 (s, 3H). ES-MS: 175 (M+1).

e) N-phenylguanidinium nitrate, see, e.g., above Example 4.

$^1$H-NMR(300 MHz, DMSO-d$_6$) ppm: 9.59 (s, 1H), 7.23-7.47 (m, 9H). LC-MS: 136 (M−NO$_3$).

Example 63

4-[2-(4-methoxyphenyl)pyrazolo[1,5-b]pyridazin-3-yl]-N-[3-(trifluoromethyl)phenyl]pyrimidin-2-amine

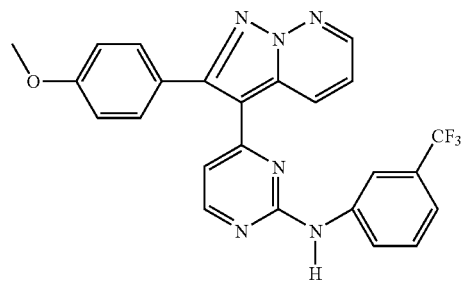

a) In a similar manner as described in Example 62a, from N-[3-(trifluoromethyl)phenyl] guanidinium nitrate was obtained the title compound as a brown solid. $^1$H-NMR (400 MHz, DMSO-d$_6$) ppm: 9.98 (s, 1H), 8.86 (d J=8.6 Hz, 1H), 8.59 (d J=2.7 Hz, 1H), 8.37 (d J=5.1 Hz, 1H), 8.24 (s, 1H), 7.92 (d J=8.0, 1H), 7.56 (d J=8.6 Hz, 2H), 7.46 (m, 1H) 7.39 (m, 1H), 7.25 (d J=7.5 Hz, 1H), 7.1 (d J=8.6 Hz, 2H), 6.62 (d J=5.1 Hz, 1H), 3.8 (s, 3H).

$^{19}$F-NMR(DMSO) ppm: −61.4 ES-MS: 463 (M+1). ES-HRMS for C$_{24}$H$_{18}$N$_6$OF$_3$: Found 463.1489. Calcd 463.1494. Elemental Analysis for C$_{24}$H$_{17}$N$_6$OF$_3$.0.15H$_2$O: Found C, 61.97; H, 3.76; N, 17.89. Calcd C, 61.97; H, 3.75; N, 18.07.

b) N-[3-(trifluoromethyl)phenyl]guanidinium nitrate $^1$H-NMR(300 MHz, DMSO-d$_6$) ppm: 9.81 (br, 1H), 7.54-7.70 (m, 8H). LC-MS: 204 (M−NO$_3$).

Example 64

N-(3,4-difluorophenyl)-4-[2-(4-methoxyphenyl)pyrazolo[1,5-]pyridazin-3-yl]pyrimidin-2-amine

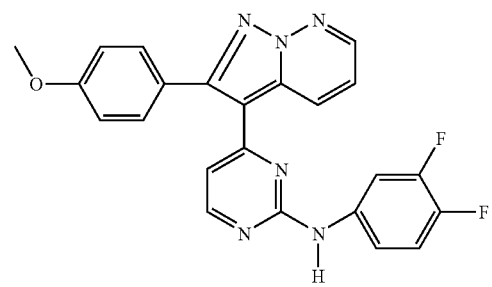

a) In a similar manner as described in Example 62a, from N-(3,4-difluorophenyl)guanidinium nitrate was obtained the title compound as a brown solid.

$^1$H-NMR(400 MHz, DMSO-$d_6$) ppm: 9.84 (s, 1H), 8.82 (d J=8.6 Hz, 1H), 8.59 (d J=2.7 Hz, 1H), 8.35 (d J=5.1 Hz, 1H), 7.89 (m, 1H), 7.55 (d J=8.6 Hz, 2H), 7.41 (m, 2H), 7.28 (m, 1H), 7.04 (d J=8.6 Hz, 2H), 6.63 (d J=5.1 Hz, 1H), 3.79 (s, 3H). $^{19}$F-NMR(DMSO) ppm: −138.08 and −148.23. ES-MS: 431 (M+1). ES-HRMS for $C_{23}H_{17}N_6OF_2$: Found 431.1440. Calcd 431.1432. Elemental Analysis for $C_{23}H_{16}N_6OF_2$·0.31$H_2O$: Found C, 63.36; H, 3.76; N, 19.08; Calcd C, 63.36; H, 3.84; N, 19.28.

b) N-(3,4-difluorophenyl)guanidinium nitrate $^1$H-NMR(300 MHz, DMSO-$d_6$) ppm: 9.64 (s, 1H), 7.40-7.56 (m, 6H), 7.11 (m, 1H). LC-MS: 172 (M−NO$_3$).

Example 65

N-(2,3-dihydro-1,4-benzodioxin-6-yl)-4-[2-(4-methoxyphenyl)pyrazolo[1,5-b]pyridazin-3-yl]pyrimidin-2-amine

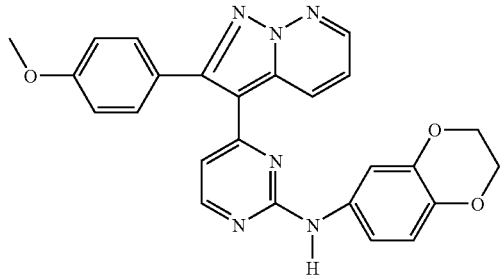

a) In a similar manner as described in Example 62a, from N-(2,3-dihydro-1,4-benzodioxin-6-yl)guanidinium nitrate was obtained the title compound as a brown solid.

$^1$H-NMR (400 MHz, DMSO-$d_6$): 9.40 (s, 1H), 8.87 (d J=8.0 Hz, 1H), 8.57 (m, 1H), 8.24 (d J=5.1 Hz, 1H), 7.54 (d J=8.6 Hz, 2H), 7.38 (m, 1H), 7.32 (d J=1.8 Hz, 1H), 7.07 (m, 3H), 6.73 (d J=8.8 Hz, 1H), 6.48 (d J=5.1 Hz, 1H), 4.18 (m, 4H), 3.80 (s, 3H). ES-MS: 453 (M+1). ES-HRMS for $C_{25}H_{21}N_6O_3$: Found: 453.1671. Calcd: 453.1675. Elemental Analysis for $C_{25}H_{20}N_6O_3$·0.31$H_2O$: Found C, 65.55; H, 4.46; N, 18.27. Calcd C, 65.55; H, 4.54; N, 18.35.

b) N-(2,3-dihydro-1,4-benzodioxin-6-yl)guanidinium nitrate $^1$H-NMR (300 MHz, DMSO-$d_6$) ppm: 9.31 (s, 1H), 7.19 (br, 4H), 6.90 (d J=8.6 Hz, 1H), 6.77 (d J=2.5 Hz, 1H), 6.69 (dd J=8.62.5 Hz), 4.24 (br, 4H). LC-MS: 194 (M−NO$_3$).

Example 66

N-[4-chloro-3-(trifluoromethyl)phenyl]-4-[2-(4-methoxyphenyl)pyrazolo[1,5-b]pyridazin-3-yl]pyrimidin-2-amine

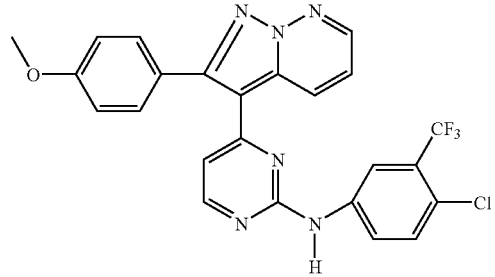

In a similar manner as described in Example 62a, from N-[4-chloro-3-(trifluoromethyl)phenyl]guanidinium nitrate was obtained the title compound as a brown solid. $^1$H-NMR (300 MHz, DMSO-$d_6$) ppm: 10.15 (s, 1H), 8.88 (d J=8.9 Hz, 1H), 8.65 (m, 1H), 8.43 (d J=5.2 Hz, 1H), 8.38 (m, 1H), 8.02 (d J=8.6 Hz, 1H), 7.60 (m, 3H), 7.45 (m, 1H), 7.09 (d J=8.6 Hz, 1H), 6.70 (d J=5.2 Hz, 1H). 3.84 (s, 3H).

$^{19}$F-NMR (DMSO) ppm: −61.62 ES-MS: 497 (M+1). ES-HRMS for $C_{24}H_{17}N_6OClF_3$: Found 497.1101. Calcd 497.1104. Elemental Analysis for $C_{24}H_{16}N_6OClF_3$: Found C, 58.14; H, 3.41; N, 16.89. Calcd C, 58.01; H, 3.25; N, 16.91.

Example 67

N-phenyl-4-{2-[4-(trifluoromethyl)phenyl]pyrazolo[1,5-b]pyridazin-3-yl}pyrimidin-2-amine

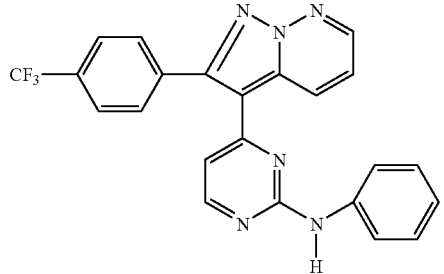

a) In a similar manner as described in Example 62a, from Example 67b and N-phenylguanidinium nitrate was obtained the title compound as a brown solid. $^1$H-NMR (300 MHz, DMSO-$d_6$) ppm: 9.68 (s, 1H), 8.86 (d J=8.8 Hz, 1H), 8.69 (m, 1H), 8.43 (d J=5.2 Hz, 1H), 7.91 (m, 4H), 7.63 (d J=7.9 Hz, 2H), 7.49 (m, 1H), 7.22 (dd J=7.9, 7.3 Hz, 2H), 6.94 (t J=7.3 Hz, 1H), 6.69 (d J=5.1 Hz).

$^{19}$F-NMR (DMSO) ppm: −61.46. ES-MS: 432 (M). ES-HRMS for $C_{23}H_{16}N_6F_3$: Found 433.1389. Calcd 433.1389. Elemental Analysis for $C_{23}H_{15}N_6F_3$: Found C, 64.14; H, 3.56; N, 19.58. Calcd C, 63.89; H, 3.50; N, 19.44.

b) (2E)-3-(dimethylamino)-1-[2-(4-trifluoromethylphenyl)pyrazolo[1,5-b]pyridazin-3-yl]prop-2-en-1-one In a similar manner as described in Example 62b, from Example 67c was obtained the title compound as a brown solid.

$^1$H-NMR (300 MHz, DMSO-$d_6$) ppm: 8.61 (br, 1H), 8.52 (d J=8.8 Hz, 1H), 7.98 (d J=8.1 Hz, 2H), 7.98 (d J=8.1 Hz, 2H), 7.60 (d J=12.3 Hz, 1H), 7.56 (m, 1H), 5.10 (d J=12.3 Hz, 1H), 3.06 (br, 3H), 2.61 (br, 3H). $^{19}$F-NMR (DMSO) ppm: −61.46 ES-MS: 360 (M).

c) 1-[2-(4-trifluoromethylphenyl)pyrazolo[1,5-b]pyridazin-3-yl]ethanone

In a similar manner as described in Example 62c, from pyridazine and 4-(4-trifluoromethylphenyl)but-3-yn-2-one was obtained the title compound as a brown solid.

$^1$H-NMR (300 MHz, DMSO-$d_6$) ppm: 8.75 (br, 1H), 8.73 (br, 1H), 7.93 (m, 4H), 7.64 (m, 1H), 2.31 (s, 3H). $^{19}$F-NMR (DMSO) ppm: −61.50 ES-MS: 306 (M+1).

d) 4-(4-trifluorophenyl)but-3-yn-2-one

In a similar manner as described in Example 62c, from pyridazine and 1-ethynyl-4-(trifluoromethyl)benzene was obtained the title compound as a yellow oil.

$^1$H-NMR (300 MHz, CDCl$_3$) ppm: 7.63 (m, 4H), 2.52 (s, 3H). CI-MS: 211 (M−1).

Example 68

N-[3-(trifluoromethyl)phenyl]-4-{2-[4-(trifluoromethyl)phenyl]pyrazolo[1,5-b]pyridazin-3-yl}pyrimidin-2-amine

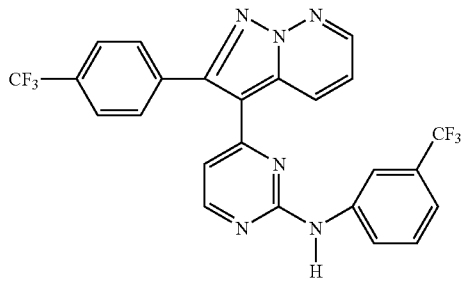

In a similar manner as described in Example 67a, from N-[3-(trifluoromethyl)phenyl]guanidinium nitrate was obtained the title compound as a brown solid. $^1$H-NMR (300 MHz, DMSO-d$_6$) ppm: 10.07 (s, 1H), 8.86 (d J=8.9 Hz, 1H), 8.71 (m, 1H), 8.49 (d J=5.1 Hz, 1H), 8.22 (s, 1H), 7.9 (m, 5H), 7.46 (m, 2H), 7.28 (d J=7.6 Hz, 1H), 6.74 (d J=5.1 Hz, 1H).

$^{19}$F-NMR (DMSO) ppm: −61.47 and −61.49. ES-MS: 500 (M). ES-HRMS for C$_{24}$H$_{15}$N$_6$F$_6$: Found 501.1271. Calcd 501.1262. Elemental Analysis for C$_{24}$H$_{14}$N$_6$F$_6$.0.42H$_2$O: Found C, 56.74; H, 2.86; N, 16.54. Calcd C, 56.75; H, 2.94; N, 16.54.

Example 69

N-(3,4-difluorophenyl)-4-{2-[4-(trifluoromethyl)phenyl]pyrazolo[1,5-]pyridazin-3-yl}pyrimidin-2-amine

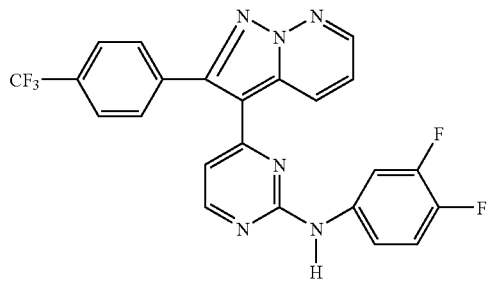

In a similar manner as described in Example 67a, from N-(3,4-difluorophenyl)guanidinium nitrate was obtained the title compound as a brown solid.

$^1$H-NMR (300 MHz, DMSO-d$_6$) ppm: 9.91 (s, 1H), 8.81 (d J=8.6 Hz, 1H), 8.71 (m, 1H), 8.49 (d J=5.1 Hz, 1H), 7.89 (m, 5H), 7.51 (m, 1H), 7.27 (m, 2H), 6.81 (d J=5.1 Hz, 1H). $^{19}$F-NMR (DMSO) ppm: −61.56, −137.88 and −148.18. ES-MS: 469 (M+1). ES-HRMS for C$_{23}$H$_{14}$N$_6$F$_5$: Found 469.1212. Calcd 469.1200. Elemental Analysis for C$_{23}$H$_{13}$N$_6$F$_5$.1.10H$_2$O: Found C, 56.74; H, 2.97; N, 16.85. Calcd C, 56.59; H, 3.14; N, 17.21.

Example 70

N-(2,3-dihydro-1,4-benzodioxin-6-yl)-4-{2-[4-(trifluoromethyl)phenyl]pyrazolo[1,5-b]pyridazin-3-yl}pyrimidin-2-amine

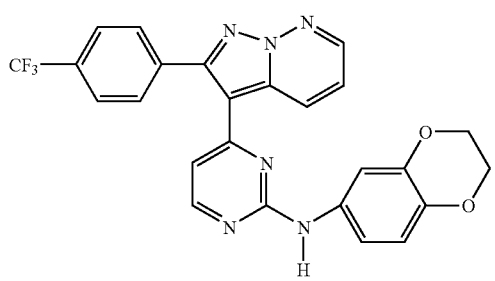

In a similar manner as described in Example 67a, from N-(2,3-dihydro-1,4-benzodioxin-6-yl)guanidinium nitrate was obtained the title compound as a brown solid.

$^1$H-NMR (300 MHz, DMSO-d$_6$) ppm: 9.49 (s, 1H), 8.87 (d J=9.5 Hz, 1H), 8.69 (br, 1H), 8.37 (d J=5.1 Hz, 1H), 7.91 (m, 4H), 7.49 (m, 1H), 7.29 (s, 1H), 7.05 (d J=8.8 Hz, 1H), 6.73 (d J=8.8 Hz, 1H), 6.59 (d J=5.1 Hz, 1H), 4.22 (br, 4H). $^{19}$F-NMR (DMSO) ppm: −61.45 ES-MS: 491 (M+1). ES-HRMS for C$_{25}$H$_{18}$N$_6$O$_2$F$_3$: Found 491.1451. Calcd 491.1443. Elemental Analysis for C$_{25}$H$_{17}$N$_6$O$_2$F$_3$: Found C, 61.27; H, 3.53; N, 17.21. Calcd C, 61.23; H, 3.49; N, 17.14.

Example 71

N-[4-chloro-3-(trifluoromethyl)phenyl]-4-{2-[4-(trifluoromethyl)phenyl]pyrazolo[1,5-b]pyridazin-3-yl}pyrimidin-2-amine

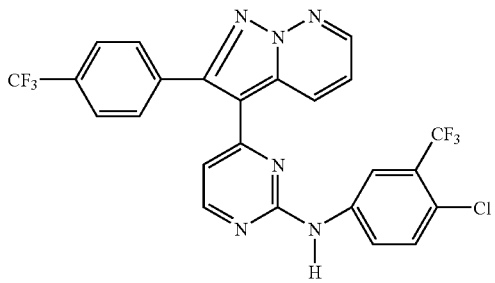

In a similar manner as described in Example 67a, from N-[4-chloro-3-(trifluoromethyl)phenyl]guanidinium nitrate was obtained the title compound as a brown solid. $^1$H-NMR (300 MHz, DMSO-d$_6$) ppm: 10.17 (s, 1H), 8.83 (d J=8.9 Hz, 1H), 8.71 (d J=3.0 Hz, 1H), 8.50 (d J=5.1 Hz, 1H), 8.30 (s, 1H), 7.89 (m, 5H), 7.50 (m, 2H), 6.79 (d J=5.1 Hz, 1H).

$^{19}$F-NMR (DMSO) ppm: −61.55 and −61.67. ES-MS: 534 (M). ES-HRMS for C$_{24}$H$_{14}$N$_6$ClF$_6$: Found 535.0875. Calcd 535.0872. Elemental Analysis for C$_{24}$H$_{13}$N$_6$ClF$_6$.0.15C$_6$H$_{14}$.0.29H$_2$O: Found C, 54.08; H, 2.79; N, 15.19. Calcd C, 54.08; H, 2.86; N, 15.20.

Example 72

4-[2-(4-chlorophenyl)pyrazolo[1,5-b]pyridazin-3-yl]-N-phenylpyrimidin-2-amine

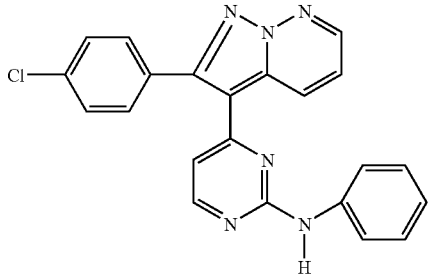

a) In a similar manner as described in Example 62a, from Example 72b and N-phenylguanidinium nitrate was obtained the title compound as a brown solid.

$^1$H-NMR (300 MHz, DMSO-d$_6$) ppm: 9.67 (s, 1H), 8.89 (d J=8.9, 1H), 8.67 (d J=2.8 Hz, 1H), 8.40 (d J=5.0 Hz, 1H), 7.66 (m, 6H), 7.47 (m, 1H), 7.25 (dd J=7.4 7.4 Hz, 2H), 6.96 (t J=7.4 Hz, 1H), 6.64 (d J=5.0 Hz, 1H). ES-MS: 399 (M+1). ES-HRMS for C$_{22}$H$_{16}$N$_6$Cl: Found 399.1139. Calcd 399.1125. Elemental Analysis for C$_2$H$_{15}$N$_8$Cl.0.38H$_2$O: Found C, 65.14; H, 3.93; N, 20.65. Calcd C, 65.13; H, 3.92; N, 20.71.

b) (2E)-1-[2-(4-chlorophenyl)pyrazolo[1,5-b]pyridazin-3-yl]-3-(dimethylamino)prop-2-en-1-one In a similar manner as described in Example 62b, from example 72c was obtained the title compound as a brown solid. $^1$H-NMR (300 MHz, DMSO-d$_6$) ppm: 8.59 (m, 1H), 8.50 (d J=8.9 Hz, 1H), 7.78 (d J=8.4 Hz, 2H), 7.59 (m, 3H), 7.39 (m, 1H), 5.13 (d J=12.5 Hz, 1H), 3.07 (br, 3H), 2.62 (br, 3H). ES-MS: 326 (M).a)

c) 1-[2-(4-chlorophenyl)pyrazolo[1,5-b]pyridazin-3-yl]ethanone

In a similar manner as described in Example 62c, from pyridazine and 4-(4-chlorophenyl)but-3-yn-2-one was obtained the title compound as a brown solid.

$^1$H-NMR (400 MHz, DMSO-d$_6$) ppm: 8.68 (m, 2H), 7.69 (d J=8.4, 2H), 7.56 (m, 3H), 2.23 (s, 3H). ES-MS: 272 (M+1).

d) 4-(4-chlorophenyl)but-3-yn-2-one

In a similar manner as described in Example 62d, from 1-Ethynyl-4-chlorobenzene was obtained the title compound as a yellow oil. (Dacca Univ. Stud., Part B (1981), 29(2), 79-85).

Example 73

4-[2-(4-chlorophenyl)pyrazolo[1,5-b]pyridazin-3-yl]-N-[3-(trifluoromethyl)phenyl]pyrimidin-2-amine

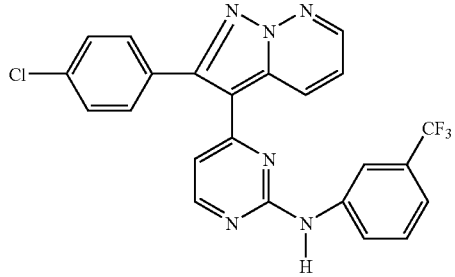

In a similar manner as described in Example 62a, from N-[3-(trifluoromethyl)phenyl]guanidinium nitrate was obtained the title compound as a brown solid. $^1$H-NMR (300 MHz, DMSO-d$_6$): 10.06 (s, 1H), 8.89 (d J=8.9 Hz, 1H), 8.69 (m, 1H), 8.46 (d J=5.1 Hz, 1H), 8.26 (s, 1H), 7.95 (d J=9.0 Hz, 1H), 7.72 (d J=8.4 Hz, 2H), 7.61 (d J=8.4 Hz, 2H), 7.50 (m, 2H), 7.30 (d J=7.6 Hz, 1H), 6.69 (d J=5.1 Hz, 1H).

$^{19}$F-NMR (DMSO): −61.44. ES-MS: 467 (M+1). ES-HRMS for C$_{23}$H$_{15}$N$_6$ClF$_3$: Found 467.0981. Calcd 467.0999. Elemental Analysis for C$_{23}$H$_{14}$N$_6$ClF$_3$.0.4H$_2$O: Found C, 58.27; H, 3.33; N, 17.57. Calcd C, 58.27; H, 3.15; N, 17.73.

Example 74

4-[2-(4-chlorophenyl)pyrazolo[1,5-b]pyridazin-3-yl]-N-(3,4-difluorophenyl)pyrimidin-2-amine

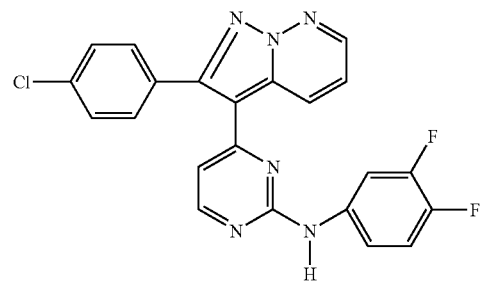

In a similar manner as described in Example 62a, from N-(3,4-difluorophenyl)guanidinium nitrate was obtained the title compound as a brown solid.

$^1$H-NMR (300 MHz, DMSO-d$_6$) ppm: 9.91 (s, 1H), 8.85 (d J=8.9 Hz, 1H), 8.68 (m, 1H), 8.45 (d J=5.2 Hz, 1H), 7.89 (m, 1H), 7.69 (d J=8.4 Hz, 2H), 7.59 (d J=8.2 Hz, 2H), 7.50 (m, 1H), 7.35 (m, 2H), 6.73 (d J=5.2 Hz, 1H). $^{19}$F-NMR (DMSO): −138.00 and −148.07. ES-MS: 435 (M+1). ES-HRMS for C$_{22}$H$_{14}$N$_6$ClF$_2$: Found 435.0940. Calcd 435.0937. Elemental Analysis for C$_{22}$H$_{13}$N$_6$ClF$_2$.0.46H$_2$O: Found C, 59.63; H, 3.14; N, 18.84; Calcd C, 59.63; H, 3.17; N, 18.97.

Example 75

4-[2-(4-chlorophenyl)pyrazolo[1,5-b]pyridazin-3-yl]-N-(2,3-dihydro-1,4-benzodioxin-6-yl)pyrimidin-2-amine

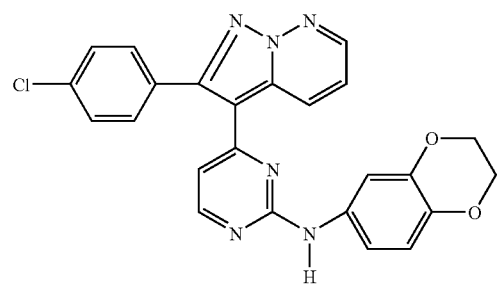

In a similar manner as described in Example 62a, from N-(2,3-dihydro-1,4-benzodioxin-6-yl)guanidinium nitrate was obtained the title compound as a brown solid.

$^1$H-NMR (300 MHz, DMSO-d$_6$) ppm: 9.48 (s, 1H), 8.89 (d J=9.0 Hz, 1H), 8.66 (m, 1H), 8.34 (d J=5.2 Hz, 1H), 7.69 (d J=8.4 Hz, 2H), 7.60 (d J=8.4 Hz, 2H), 7.46 (m, 1H), 7.33 (s, 1H), 7.08 (d J=8.7 Hz, 1H), 6.76 (d J=8.7 Hz, 1H), 6.55 (d J=5.2 Hz, 1H), 4.23 (br, 4H). ES-MS: 457 (M+1). ES-HRMS for $C_{24}H_{18}N_6O_2Cl$: Found 457.1191. Calcd 457.1180. Elemental Analysis for $C_{24}H_{17}N_6O_2Cl.0.5H_2O$: Found C, 61.88; H, 3.80; N, 17.88. Calcd C, 61.87; H, 3.89; N, 18.04.

Example 76

4-[2-(4-chlorophenyl)pyrazolo[1,5-b]pyridazin-3-yl]-N-[4-chloro-3-(trifluoromethyl)phenyl]pyrimidin-2-amine

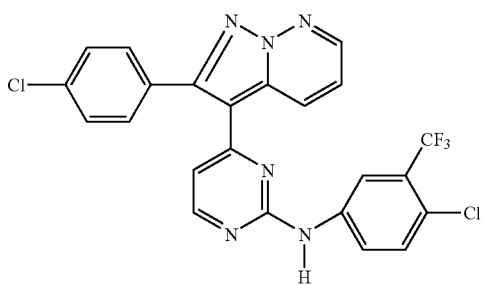

In a similar manner as described in Example 62a, from N-[4-chloro-3-(trifluoromethyl)phenyl]guanidinium nitrate was obtained the title compound as a brown solid. $^1$H-NMR (300 MHz, DMSO-d$_6$) ppm: 10.16 (s, 1H), 8.86 (d J=8.8 Hz, 1H), 8.69 (m, 1H), 8.48 (d J=5.2 Hz, 1H), 8.35 (d J=2.3 Hz, 1H), 7.99 (d J-8.5 Hz, 1H), 7.70 (d J=8.5 Hz, 2H), 7.58 (m, 3H), 7.48 (m, 1H), 6.73 (d J=5.2 Hz, 1H).

$^{19}$F-NMR (DMSO): −61.64. ES-MS: 501 (M+1). ES-HRMS for $C_{23}H_{14}N_6Cl_2F_3$: Found 501.0611. Calcd 501.0609. Elemental Analysis for $C_{23}H_{13}N_6Cl_2F_3$: Found C, 55.24; H, 2.93; N, 16.37. Calcd C, 55.11; H, 2.61; N, 16.76.

Example 77

4-{6-methyl-2-[4-(trifluoromethyl)phenyl]pyrazolo[1,5-b]pyridazin-3-yl}-N-phenylpyrimidin-2-amine

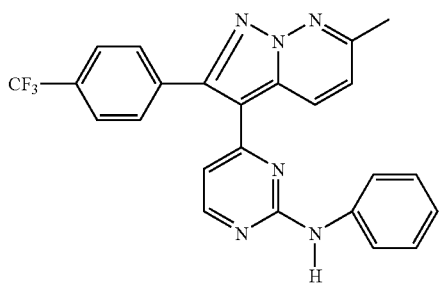

a) In a similar manner as described in Example 62a, from Example 77b and N-phenylguanidinium nitrate was obtained the title compound as a brown solid.

$^1$H-NMR (300 MHz, DMSO-d$_6$) ppm: 9.62 (s, 1H), 8.71 (d J=9.2 Hz, 1H), 8.36 (d J=5.0 Hz, 1H), 7.85 (br, 4H), 7.59 (d J=7.8 Hz, 1H), 7.37 (d J=9.2 Hz, 1H), 7.32 (m, 1H), 7.18 (dd J=7.8, 7.5 Hz, 2H), 6.91 (m, 1H), 6.62 (d J=5.0 Hz, 1H), 2.59 (s, 3H). $^{19}$F-NMR (DMSO) ppm: −61.45. ES-MS: 446 (M). ES-HRMS for $C_{24}H_{18}N_6F_3$: Found 447.1532. Calcd 447.1545. Elemental Analysis for $C_{24}H_{17}N_6F_3.0.36H_2O.0.19C_4H_8O_2$: Found C, 63.32; H, 4.00; N, 17.89. Calcd C, 63.32; H, 4.13; N, 17.89.

b) (2E)-3-(dimethylamino)-1-{6-methyl-2-[4-(trifluoromethyl)phenyl]pyrazolo[1,5-b]pyridazin-3-yl}prop-2-en-1-one In a similar manner as described in Example 6b, from 77c was obtained the title compound as a brown solid. $^1$H-NMR (300 MHz, DMSO-d$_6$) ppm: 8.37 (d J=9.2 Hz, 1H), 7.93 (d J=8.3 Hz, 2H), 7.83 (d J=8.3 Hz, 2H), 7.54 (d J=12.5 Hz, 1H), 7.30 (d J=9.2 Hz, 1H), 5.05 (d J=12.5 Hz, 1H), 3.02 (s, 3H), 2.56 (s, 3H), 2.48 (s, 3H).

$^{19}$F-NMR (DMSO) ppm: −61.42. ES-MS: 374 (M).

c) 1-{6-methyl-2-[4-(trifluoromethyl)phenyl]pyrazolo[1,5-b]pyridazin-3-yl}ethanone In a similar manner as described in Example 62c, from 67d was obtained the title compound as a brown solid. $^1$H-NMR (300 MHz, DMSO-d$_6$) ppm: 8.58 (d J=9.3 Hz, 1H), 7.88 (m, 4H), 7.51 (d J=9.3 Hz, 1H), 2.59 (s, 3H), 2.26 (s, 3H).

$^{19}$F-NMR (DMSO): −63.04. ES-MS: 320 (M+1).

Example 78

N-(2,3-dihydro-1,4-benzodioxin-6-yl)-4-[6-methyl-2-(4-methylphenyl)pyrazolo[1,5-b]pyridazin-3-yl]pyrimidin-2-amine

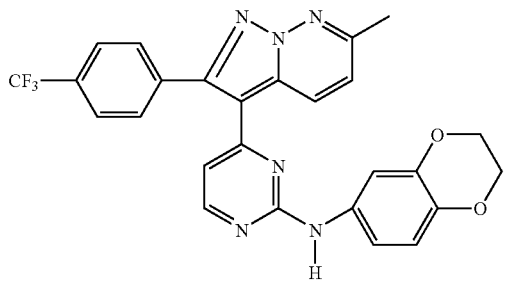

In a similar manner as described in Example 62a, from N-(2,3-dihydro-1,4-benzodioxin-6-yl)guanidinium nitrate was obtained the title compound as a brown solid.

$^1$H-NMR (300 MHz, DMSO-d$_6$) ppm: 9.42 (s, 1H), 8.72 (d J=9.1 Hz, 1H), 8.30 (d J=5.2 Hz, 1H), 7.84 (br, 4H), 7.36 (d J=9.1 Hz, 1H), 7.24 (s, 1H), 7.01 (d J=8.7 Hz, 1H), 6.68 (d J=8.7 Hz, 1H), 6.52 (d J=5.1 Hz, 1H), 4.18 (br, 4H), 2.59 (s, 3H). $^{19}$F-NMR (DMSO): −61.43. ES-MS: 505 (M+1). ES-HRMS for $C_{28}H_{20}N_6O_2F_3$: Found 505.1592. Calcd 505.1600. Elemental Analysis for $C_{26}H_{19}N_6O_2F_3$: Found C, 62.18; H, 3.90; N, 16.63. Calcd C, 62.90; H, 3.80; N, 16.66.

Example 79

N-[3,5-bis(trifluoromethyl)phenyl]-4-pyrazolo[1,5-b]pyridazin-3-yl-2-pyrimidinamine

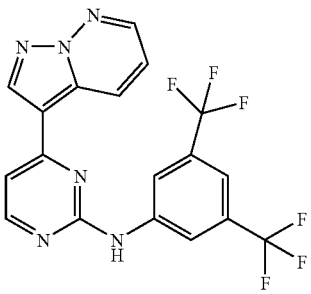

a) N-[3,5-bis(trifluoromethyl)phenyl]4-pyrazolo[1,5-b]pyridazin-3-yl-pyrimidinamine In a similar manner as described in Example 1a, from N-[3,5-bis(trifluoromethyl) phenyl]guanidine nitrate was obtained the title compound.

$^1$H-NMR (300 MHz, d$^6$-DMSO) δ 10.31 (s, 1H), 9.13 (d, 1H, J=8.9 Hz), 8.96 (s, 1H), 8.64 (m, 2H), 8.52 (s, 2H), 7.64-7.46 (m, 3H); MS (ESI) (M+H)$^+$ 425.

b) N-[3,5-bis(trifluoromethyl)phenyl]guanidine nitrate

In a similar manner as described in Example 7b, from 3,5-bis(trifluoromethyl)aniline was obtained the title compound. $^1$H-NMR (300 MHz, d$^6$-DMSO) δ 10.03 (s, 1H), 8.01 (s, 1H), 7.95 (s, 2H), 7.79 (s, 3H); MS (ESI) (M+H)$^+$ 272.

Example 80

N-(3,5-dimethoxyphenyl)-4-pyrazolo[1,5-b]pyridazin-3-yl-2-pyrimidinamine

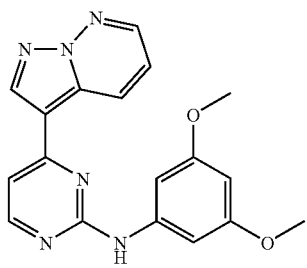

a) In a similar manner as described in Example 1a, from N-[3,5-dimethoxy)phenyl]guanidine nitrate was obtained the title compound.

$^1$H-NMR (300 MHz, d$^6$-DMSO) δ 9.56 (s, 1H), 9.26 (d, 1H, J=8.9 Hz), 8.92 (s, 1H), 8.63 (s, 1H), 8.52 (d, 1H, J=5.1 Hz), 7.49-7.40 (m, 2H), 7.07 (s, 2H), 6.19 (s, 1H), 3.76 (s, 6H); MS (ESI) (M+H)$^+$ 349.

b) N-(3,5-dimethoxyphenyl)guanidine nitrate

Prepared from 3,5-dimethoxyaniline as described in published international patent application WO 00/78731, herein incorporated by reference to such extent.

Example 81

N-(4-sec-butylphenyl)-4-pyrazolo[1,5-b]pyridazin-3-yl-2-pyrimidinamine

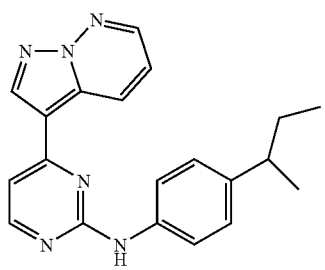

a) To 3-[2-(methylsulfonyl)-4-pyrimidinyl]pyrazolo[1,5-b]pyridazine 0.1 g (0.363 mmol) was added 0.54 g (3.63 mmol) of the amine and the contents heated at 170° C. for 15 mins. The reaction mixture was cooled, washed with ethanol and dried to afford a pale yellow solid.

$^1$H-NMR (300 MHz, d$^6$-DMSO) δ 9.49 (s, 1H), 9.18 (m, 1H), 8.95-8.91 (m, 2H), 8.67 (s, 1H), 8.62 (s, 1H), 7.66 (d, 2H, J=7.8 Hz), 7.43 (m, 1H), 7.19 (d, 2H, J=7.8 Hz), 1.6 (m, 3H), 1.23 (d, 3H, J=6.6 Hz), 0.81 (t, 3H, J=6.8 Hz); MS (M+H)$^+$ 345.

b) 3-[2-(methylsulfonyl)-pyrimidinyl]pyrazolo[1,5-b]pyridazine

To a solution of 3-[2-(methylsulfanyl)-4-pyrimidinyl]pyrazolo[1,5-b]pyridazine 2.0 g (8.20 mmol) in 70 mL DCM was added m-CPBA 4.88 g (20.5 mmol). After stirring for an hour, the reaction mixture was washed with satd. Sodium bisulfite solution followed by brine water. The organic layer was separated, dried with magnesium sulfate and concentrated to afford 3-[2-(methylsulfonyl)-4-pyrimidinyl]pyrazolo[1,5-b]pyridazine as a pale yellow solid which was carried over crude to the next step. $^1$H-NMR (300 MHz, d$^6$-DMSO) δ 8.96 (s, 1H), 8.94-8.91 (m, 1H), 8.66 (m, 1H), 8.61 (d, 1H, J=5.3 Hz), 7.72 (d, 1H, J=5.3 Hz), 7.55 (m, 1H), 3.35 (s, 3H)

c) 3-[2-(methylsulfanyl)-4-pyrimidinyl]pyrazolo[1,5-b]pyridazine

In a similar manner as described in Example 62c, from 4-ethynyl-2-(methylthio)pyrimidine and was obtained the title compound as a brown solid. $^1$H-NMR (300 MHz, d$^6$-DMSO) δ 9.04 (s, 1H), 9.02-8.99 (m, 2H), 8.74 (m, 1H), 8.32 (d, 1H, J=5.3 Hz), 7.67 (m, 1H), 3.53 (s, 3H)

Example 82

N-(4-tert-butylphenyl)-4-pyrazolo[1,5-b]pyridazin-3-yl-2-pyrimidinamine

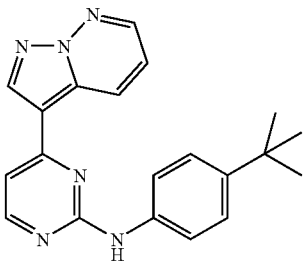

In a similar manner as described in Example 81a, from 3-[2-(methylsulfonyl)-4-pyrimidinyl]pyrazolo[1,5-b]pyridazine and 4-tert-butylaniline was obtained the title compound as a pale yellow solid.

$^1$H-NMR (300 MHz, d$^6$-DMSO) δ 9.58 (s, 1H), 9.24 (m, 1H), 8.96 (br s, 1H), 8.81-8.39 (m, 2H), 7.65 (d, 2H, J=7.6 Hz), 7.36-7.21 (m, 4H); MS (ESI) (M+H)$^+$ 345.

Example 83

N-(3,5-dichlorophenyl)-4-pyrazolo[1,5-b]pyridazin-3-yl-2-pyrimidinamine

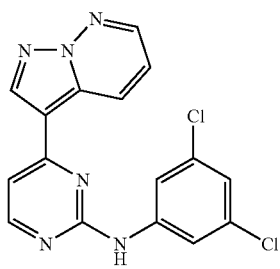

a) In a similar manner as described in Example 1a, form N-(3,5-dichlorophenyl)guanidine nitrate was obtained the title compound as a brown solid.

$^1$H-NMR (300 MHz, d$^6$-DMSO) δ 9.98 (s, 1H), 9.14 (d, 1H, J=9.0 Hz), 8.93 (s, 1H), 8.65 (s, 1H), 8.58 (d, 1H, J=5.2 Hz), 7.91 (s, 2H), 7.51 (m, 2H), 7.15 (s, 1H); MS (ESI) (M+H)$^+$ 357.

b) N-(3,5-dichlorophenyl)guanidine nitrate

In a similar manner as described in Example 7b, from 3,5-dichloroaniline was obtained the title compound as a pale brown solid.

$^1$H-NMR (300 MHz, d$^6$-DMSO) δ 10.1 (brs, 1H), 7.66 (m, 3H), 7.53 (s, 1H), 7.36 (s, 2H). MS (ESI) (M+H)$^+$ 204.

Example 84

N-(3,4-dichlorophenyl)-4-pyrazolo[1,5-b]pyridazin-3-yl-2-pyrimidinamine

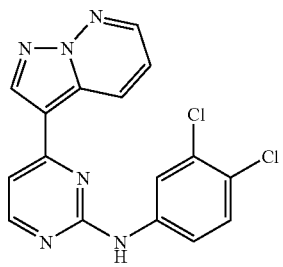

a) In a similar manner as described in Example 1a, from N-(3,4-dichlorophenyl)guanidine nitrate was obtained the title compound as a brown solid.

$^1$H-NMR (300 MHz, d$^6$-DMSO) δ 9.87 (s, 1H), 9.11 (d, 1H, J=8.4 Hz), 8.88 (s, 1H), 8.60 (s, 1H), 8.51 (s, 1H), 8.23 (s, 1H), 7.63-7.42 (m, 4H); MS (ESI) (M+H)$^+$ 357.

b) N-(3,4-dichlorophenyl)guanidine nitrate

Prepared as described in J. Med. Chem. (1987), 30(11), 1943-8, herein incorporated by reference to such extent.

Example 85

N-(3,5-difluorophenyl)-4-pyrazolo[1,5-b]pyridazin-3-yl-2-pyrimidinamine

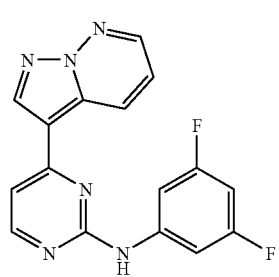

a) In a similar manner as described in Example 1a, from N-(3,5-difluorophenyl)guanidine nitrate was obtained the title compound as a brown solid.

$^1$H-NMR (300 MHz, d$^6$-DMSO) δ 9.99 (s, 1H), 9.18 (d, 1H, J=9.1 Hz), 8.92 (s, 1H), 8.64 (m, 1H), 8.56 (m, 1H), 7.59-7.47 (m, 4H), 6.80 (m, 1H). MS (ESI) (M+H)$^+$ 325.

b) N-(3,5-difluorophenyl)guanidine nitrate

In a similar manner as described in Example 7b, from 3,5-difluoroaniline was obtained the title compound as a white solid.

$^1$H-NMR (300 MHz, d$^6$-DMSO) δ 9.89 (brs, 1H), 7.67 (brs, 3H), 7.22 (m, 1H), 7.18 (m, 2H); MS (ESI) (M+H)$^+$ 172.

Example 86

N-[3-bromo-5-(trifluoromethyl)phenyl]-4-pyrazolo[1,5-b]pyridazin-3-yl-2-pyrimidinamine

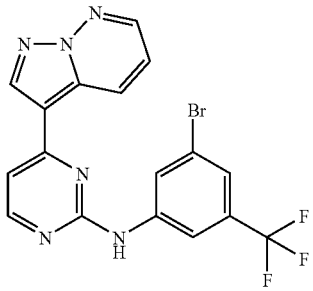

a) In a similar manner as described in Example 1a, from N-[3-bromo-5-(trifluoromethyl)phenyl]guanidine nitrate was obtained the title compound as a white solid.

$^1$H-NMR (300 MHz, d$^6$-DMSO) δ 10.1 (s, 1H), 9.09 (d, 1H, J=8.9 Hz), 8.92 (s, 1H), 8.62-8.56 (m, 2H), 8.38 (s, 1H), 8.13 (s, 1H), 7.49 (m, 3H); MS (ESI) (M+H)$^+$ 436.

b) N-[3-bromo-5-(trifluoromethyl)phenyl]guanidine nitrate

In a similar manner as described in Example 7b, from 3-bromo-5-(trifluoromethyl)aniline was obtained the title compound as a pale yellow solid.

$^1$H-NMR (300 MHz, d$^6$-DMSO) δ 8.24 (brs, 1H), 7.84 (s, 1H), 7.77 (s, 1H), 7.70 (brs, 3H), 7.58 (s, 1H); MS (ESI) (M+H)$^+$ 283.

Example 87

N-(3,4-dihydro-2H-1,5-benzodioxepin-7-yl)-4-pyrazolo[1,5-b]pyridazin-3-yl-2-pyrimidinamine

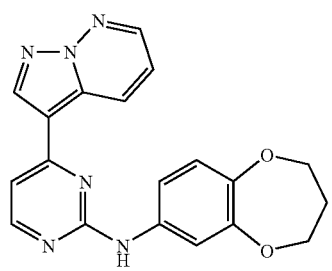

In a similar manner as described in Example 90a, from 3,4-dihydro-2H-1,5-benzodioxepin-7-amine was obtained the title compound as a pale yellow solid.

$^1$H-NMR (300 MHz, d$^6$-DMSO) δ 9.52 (s, 1H), 9.20 (d, 1H, J=9.8 Hz), 8.92 (s, 1H), 8.64 (s, 1H), 8.49 (d, 1H, J=5.3 Hz), 7.57-7.23 (m, 4H), 6.99 (s, 1H) 4.16-4.01 (m, 4H), 2.12 (m, 2H); MS (ESI) (M+H)$^+$ 361.

Example 88

3-[(4-pyrazolo[1,5-b]pyridazin-3-yl-2-pyrimidinyl)amino]-5-(trifluoromethyl)benzamide

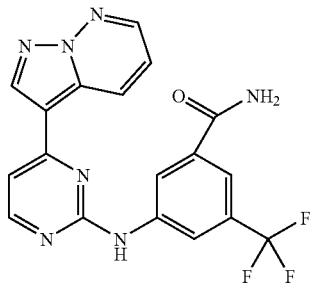

a) In a similar manner as described in Example 1a, from 3-{[amino(imino)methyl]amino}-5-(trifluoromethyl)benzamide nitrate was obtained the title compound as a brown solid.

$^1$H-NMR (300 MHz, d$^6$-DMSO) δ 9.99 (s, 1H), 9.21 (d, 1H, J=9.2 Hz), 8.98 (s, 2H), 8.66-8.25 (m, 5H), 7.82 (s, 1H), 7.62-7.47 (m, 3H): MS (ESI) (M+H)$^+$ 400.

b) 3-{[amino(imino)methyl]amino}-5-(trifluoromethyl)benzamide nitrate

In a similar manner as described in Example 7b, from 3-amino-5-(trifluoromethyl)benzamide was obtained the title compound as a yellow solid.

$^1$H-NMR (300 MHz, d$^6$-DMSO) δ 9.87 (brs, 1H), 8.26 (s, 1H), 8.09 (s, 1H), 8.00 (s, 1H), 7.72 (d, 2H, J=9.1 Hz), 7.62 (brs, 3H); MS (APCI) (M+H)$^+$ 247.

Example 89

N-(3,4-difluorophenyl)-4-pyrazolo[1,5-b]pyridazin-3-yl-2-pyrimidinamine

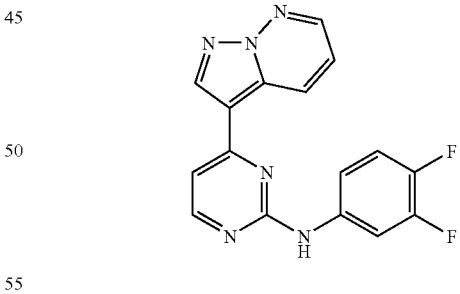

a) In a similar manner as described in Example 1a, from N-(3,4-difluorophenyl)guanidine was obtained the title compound as a brown solid.

$^1$H-NMR (300 MHz, d$^6$-DMSO) δ 9.82 (s, 1H), 9.18 (d, 1H, J=8.8 Hz), 8.93 (s, 1H), 8.65 (d, 1H, J=3.2 Hz), 8.54 (d, 1H, J=5.3 Hz), 8.06-7.99 (m, 1H), 7.53-7.37 (m, 4H); MS (ESI) (M+H)$^+$ 325.

b) N-(3,4-difluorophenyl)guanidine

Prepared as described in International Patent Publication WO 00/78731, herein incorporated by reference to such extent.

Example 90

N-[4-chloro-3-(trifluoromethyl)phenyl]-4-pyrazolo[1,5-b]pyridazin-3-yl-2-pyrimidinamine

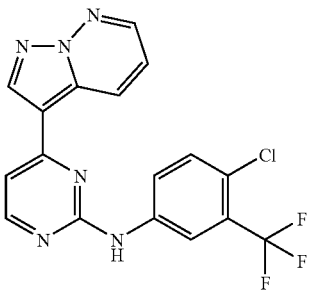

a) In a similar manner as described in Example 1a, from N-[4-chloro-3-(trifluoromethyl)phenyl]guanidine nitrate was obtained the title compound as a brown solid.

$^1$H-NMR (300 MHz, d$^6$-DMSO) δ 10.08 (s, 1H), 9.15 (d, 1H, J=9.1 Hz), 8.95 (s, 1H), 8.67 (d, 1H, J=4.0 Hz), 8.58 (d, 1H, J=5.3), 8.41 (s, 1H), 8.08 (d, 1H, J=8.5 Hz), 7.70 (d, 1H, J=8.8 Hz), 7.49 (m, 2H); MS (ESI) (M+H)$^+$ 391.

b) N-[4-chloro-3-(trifluoromethyl)phenyl]guanidine nitrate

In a similar manner as described in Example 7b, from 4-chloro-3-(trifluoromethyl)aniline was obtained the title compound as a yellow solid.

$^1$H-NMR (300 MHz, d$^6$-DMSO) δ 9.84 (brs, 1H), 7.81-7.45 (m, 6H); MS (ESI) (M+H)$^+$ 238.

Example 91

N-phenyl-4-(2-phenylpyrazolo[1,5-b]pyridazin-3-yl)-2-pyrimidinamine

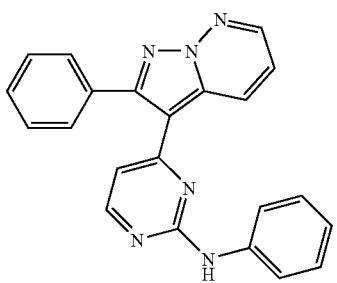

a) In a similar manner as described in Example 62a, from (2E)-3-(dimethylamino)-1-(2-phenylpyrazolo[1,6-b]pyridazin-3-yl)-2-propen-1-one and N-phenylguanidinium nitrate was obtained the title compound as a brown solid.

$^1$H-NMR (300 MHz, d$^6$-DMSO) δ 9.66 (s, 1H), 8.95 (d, 1H, J=8.9 Hz), 8.65 (m, 1H), 8.35 (d, 1H, J=5.2), 7.71-7.46 (m, 8H), 7.29 (t, 2H, J=4.3 Hz), 6.99 (t, 1H, J=7.8 Hz), 6.57 (d, 1H, J=7.3 Hz); MS (ESI) (M+H)$^+$ 365.

b) (2E)-3-(dimethylamino)-1-(2-phenylpyrazolo[1,5-b]pyridazin-3-yl)-2-propen-1-one In a similar manner as described in Example 62b, from 1-(2-phenylpyrazolo[1,5-b]pyridazin-3-yl)ethanone was obtained the title compound as a brown solid.

$^1$H-NMR (300 MHz, d$^6$-DMSO) δ 8.59 (m, 3H), 7.74-7.50 (m, 6H), 5.10 (d, 1H, J=12.5 Hz), 3.36 (brs, 3H), 2.52 (brs, 3H); MS (ESI) (M+H)$^+$ 293.

c) 1-(2-phenylpyrazolo[1,5-b]pyridazin-3-yl)ethanone

In a similar manner as described in Example 62c, from 4-phenyl-3-butyn-2-one was obtained the title compound as a brown solid.

$^1$H-NMR (300 MHz, d$^6$-DMSO) δ 8.74 (m, 3H), 7.71-7.55 (m, 5H), 2.21 (s, 3H);

Example 92

4-(2-phenylpyrazolo[1,5-b]pyridazin-3-yl)-N-[3-(trifluoromethyl)phenyl]-2-pyrimidinamine

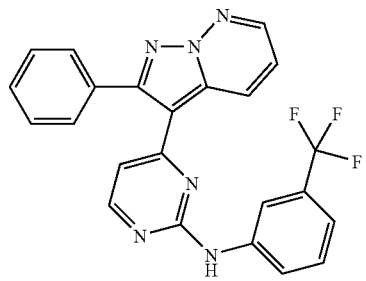

In a similar manner as described in Example 62a, from N-[3-(trifluoromethyl)phenyl]guanidine was obtained the title compound as a brown solid.

$^1$H-NMR (300 MHz, d$^6$-DMSO) δ 10.04 (s, 1H), 8.95 (d, 1H J=9.0 Hz), 8.68 (s, 1H), 8.41 (d, 1H, J=5.2 Hz), 8.28 (s, 1H), 7.68-7.7.44 (m, 8H), 7.31 (d, 1H, J=7.7 Hz), 6.63 (d, 1H, J=5.2 Hz); MS (ESI) (M+H)$^+$ 433.

Example 93

N-[4-chloro-3-(trifluoromethyl)phenyl]-4-(2-phenylpyrazolo[1,5-b]pyridazin-3-yl)-2-pyrimidinamine

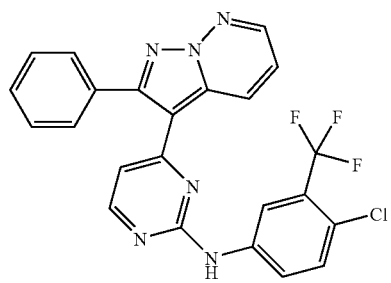

In a similar manner as described in Example 62a, from N-[4-chloro-3-(trifluoromethyl)phenyl]guanidinium nitrate was obtained the title compound as a brown solid.

$^1$H-NMR (300 MHz, d$^6$-DMSO) δ 10.15 (s, 1H), 8.92 (d, 1H, J=9.0 Hz), 8.68 (m, 1H), 8.43 (d, 1H, J=5.3 Hz), 8.37 (s, 1H), 8.01 (d, 1H, J=8.8 Hz), 7.69-7.46 (m, 7H), 6.66 (d, 1H, J=5.2 Hz); MS (ESI) (M+H)$^+$ 467.

Example 94

N-(2,3-dihydro-1,4-benzodioxin-6-yl)-4-(2-phenylpyrazolo[1,5-b]pyridazin-3-yl)-2-pyrimidinamine

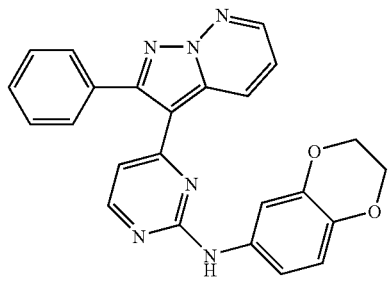

In a similar manner as described in Example 62a, from N-(2,3-dihydro-1,4-benzodioxin-6-yl)guanidinium nitrate was obtained the title compound as a brown solid.

$^1$H-NMR (300 MHz, d$^6$-DMSO) δ 9.43 (s, 1H), 8.93 (d, 1H, J=8.8 Hz), 8.61 (m, 1H), 8.24 (d, 1H, J=5.2 Hz), 7.61-7.31 (m, 7H), 7.09 (d, 1H, J=8.7 Hz), 6.74 (d, 1H, J=8.6 Hz), 6.44 (d, 1H, J=5.2 Hz), 4.10 (brs, 4H); MS (ESI) (M+H)$^+$ 423.

Example 95

N-(3,5-difluorophenyl)-4-(2-phenylpyrazolo[1,5-b]pyridazin-3-yl)-2-pyrimidinamine

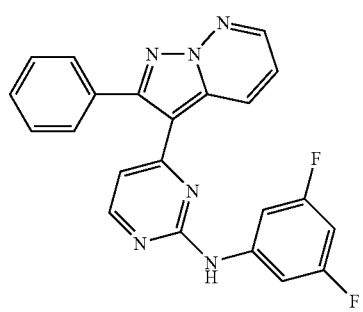

In a similar manner as described in Example 62a, from N-(3,5-difluorophenyl)guanidinium nitrate was obtained the title compound as a brown solid $^1$H-NMR (300 MHz, d$^6$-DMSO) δ 10.0 (s, 1H), 8.91 (d, 1H, J=8.8 Hz), 8.64 (m, 1H), 8.37 (d, 1H, J=5.3 Hz), 8.24 (s, 1H), 7.93 (d, 1H, J=8.2 Hz), 7.64-7.40 (m, 6H), 7.27 (d, 1H, J=7.7 Hz), 6.59 (d, 1H, J=5.2 Hz); MS (ESI) (M+H)$^+$ 401.

Example 96

N-(3,4-difluorophenyl)-4-(2-phenylpyrazolo[1,5-b]pyridazin-3-yl)-2-pyrimidinamine

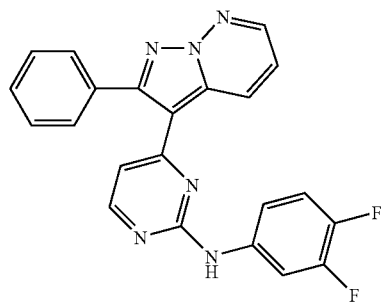

In a similar manner as described in Example 62a, from N-(3,4-difluorophenyl)guanidinium nitrate was obtained the title compound as a brown solid $^1$H-NMR (300 MHz, d$^6$-DMSO) δ 9.85 (s, 1H), 8.86 (d, 1H, J=8.1 Hz), 8.62 (s, 1H), 8.35 (d, 1H, J=4.4 Hz), 7.86 (m, 1H), 7.61-7.26 (m, 8H), 6.59 (d, 1H, J=4.0 Hz); MS (ESI) (M+H)$^+$ 401.

Example 97

4-[2-(4-fluorophenyl)pyrazolo[1,5-b]pyridazin-3-yl]-N-phenyl-2-pyrimidinamine

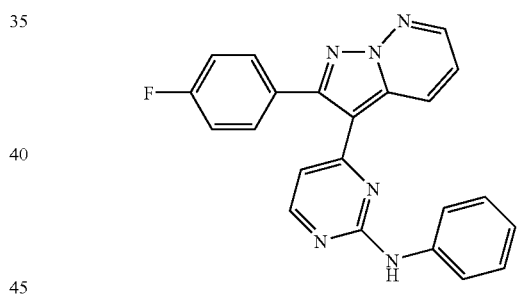

a) In a similar manner as described in Example 62a, from N-phenylguanidinium nitrate was obtained the title compound as a brown solid $^1$H-NMR (300 MHz, d$^6$-DMSO) δ 9.64 (s, 1H), 8.87 (m, 1H), 8.63 (s, 1H), 8.35 (s, 1H), 7.68-7.24 (m, 9H), 6.95 (s, 1H), 6.58 (s, 1H); MS (ESI) (M+H)$^+$ 383.

b) (2E)-3-(dimethylamino)-1-[2-(4-fluorophenyl)pyrazolo[1,5-b]pyridazin-3-yl]-2-propen-1-one In a similar manner as described in Example 62b, from 1-[2-(4-fluorophenyl)pyrazolo[1,5-b]pyridazin-3-yl]ethanone was obtained the title compound as a brown solid.

$^1$H-NMR (300 MHz, d$^6$-DMSO) δ 8.59 (m, 2H), 7.81 (m, 2H), 7.60 (m, 1H), 7.40 (m, 3H), 5.12 (d, 1H, J=12.4 Hz), 3.06 (brs, 3H), 2.59 (brs, 3H); MS (ESI) (M+H)$^+$ 311.

c) 1-[2-(4-fluorophenyl)pyrazolo[1,5-b]pyridazin-3-yl]ethanone

In a similar manner as described in Example 62c, from 1-[2-(4-fluorophenyl)pyrazolo[1,5-b]pyridazin-3-yl]ethanone was obtained the title compound as a brown solid.

$^1$H-NMR (300 MHz, d$^6$-DMSO) δ 8.73 (m, 2H), 7.79-7.59 (m, 4H), 7.42-7.36 (m, 2H), 2.25 (s, 3H)

Example 98

N-(2,3-dihydro-1,4-benzodioxin-6-yl)-4-[2-(4-fluorophenyl)pyrazolo[1,5-b]pyridazin-3-yl]-2-pyrimidinamine

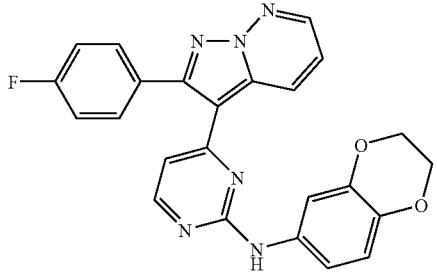

In a similar manner as described in Example 62a, from N-(2,3-dihydro-1,4-benzodioxin-6-yl)guanidinium nitrate was obtained the title compound as a brown solid.

$^1$H-NMR (300 MHz, d$^6$-DMSO) δ 9.43 (s, 1H), 8.89 (d, 1H, J=9.2 Hz), 8.69 (m, 1H), 8.62 (d, 1H, J=5.1 Hz), 7.70 (m, 2H), 7.44-7.30 (m, 4H), 7.06 (d, 1H, J=8.9 Hz), 6.73 (d, 1H, J=5.1 Hz), 6.48 (d, 1H, J=5.1 Hz), 4.58 (brs, 4H); MS (ESI) (M+H)$^+$ 441.

Example 99

4-[2-(4-fluorophenyl)pyrazolo[1,5-b]pyridazin-3-yl]-N-[3-(trifluoromethyl)phenyl]-2-pyrimidinamine

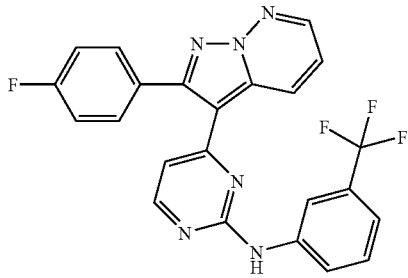

In a similar manner as described in Example 62a, from N-[3-(trifluoromethyl)phenyl]guanidine was obtained the title compound as a brown solid.

$^1$H-NMR (300 MHz, d$^6$-DMSO) δ 10.04 (s, 1H), 8.92 (d, 1H, J=8.9 Hz), 8.68 (m, 1H), 8.44 (d, 1H, J=5.2 Hz), 8.26 (s, 1H), 7.96 (d, 1H, J=8.3 Hz), 7.76 (m, 2H), 7.52 (m, 5H), 6.66 (d, 1H, J=5.3 Hz); MS (ESI) (M1H)$^+$ 451.

Example 100

N-[4-chloro-3-(trifluoromethyl)phenyl]-4-[2-(4-fluorophenyl) pyrazolo[1,5-b]pyridazin-3-yl]-2-pyrimidinamine

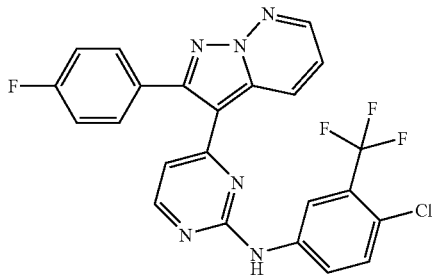

In a similar manner as described in Example 62a, from N-[4-chloro-3-(trifluoromethyl)phenyl]guanidinium nitrate was obtained the title compound as a brown solid.

$^1$H-NMR (300 MHz, d$^6$-DMSO) δ 10.11 (s, 1H), 8.63 (d, 1H, J=8.8 Hz), 8.68 (m, 1H), 8.41 (d, 1H, J=5.1 Hz), 8.32 (s, 1H), 7.96 (d, 1H, J=8.7 Hz), 7.69-7.30 (m, 6H), 6.65 (d, 1H. J=5.1 Hz); MS (ESI) (M+H)$^+$ 485.

Example 101

N-(3,4-difluorophenyl)-4-[2-(4-fluorophenyl)pyrazolo[1,5-b]pyridazin-3-yl]-2-pyrimidinamine

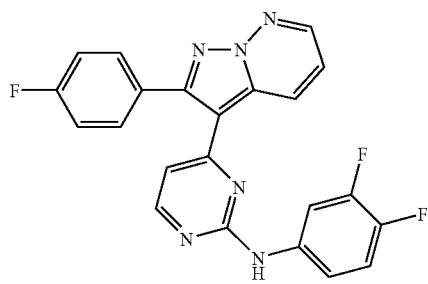

In a similar manner as described in Example 62a, from N-(3,4-difluorophenyl)guanidinium nitrate was obtained the title compound as a brown solid.

$^1$H-NMR (300 MHz, d$^6$-DMSO) δ 9.85 (s, 1H), 8.82 (d, 1H, J=9.2 Hz), 8.68 (m, 2H), 8.38 9d, 1H, J=5.1 Hz), 7.84-7.28 (m, 7H), 6.64 (d, 1H, J=5.3 Hz); MS (ESI) (M+H)$^+$ 419.

Example 102

N-phenyl-4-{2-[3-(trifluoromethyl)phenyl]pyrazolo[1,5-b]pyridazin-3-yl}-2-pyrimidinamine

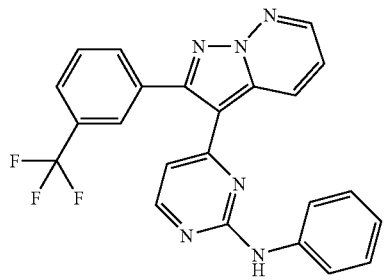

a) In a similar manner as described in Example 62a, from N-phenylguanidinium nitrate was obtained the title compound as a brown solid.

$^1$H-NMR (300 MHz, d$^6$-DMSO) δ 9.68 (s, 1H), 8.88 (d, 1H, J=8.8 Hz), 8.69 (m, 1H), 8.42 (d, 1H, J=5.3 Hz), 8.02-7.74 (m, 6H), 7.65 (d, 1H, J=8.0 Hz), 7.48 (m, 1H), 7.25 (m, 1H), 6.67 (d, 1H, J=5.2 Hz); MS (ESI) (M+H)$^+$ 433.

b) (2E)-3-(dimethylamino)-1-{2-[3-(trifluoromethyl)phenyl]pyrazolo[1,5-b]-3-pyridazin-3-yl}-2-propen-1-one In a similar manner as described in Example 62b, from 1-[2-(4-fluorophenyl)pyrazolo[1,5-b]pyridazin-3-yl]ethanone was obtained the title compound as a brown solid.

¹H-NMR (300 MHz, d⁶-DMSO) δ 8.53 (m, 2H), 7.98 (m, 2H), 7.76 (m, 2H), 7.50 (m, 1H), 7.32 (m, 1H), 5.05 (d, 1H, J=12.5 Hz), 2.97 (brs, 3H), 2.51 (brs, 3H); MS (ESI) (M+H)⁺ 361.

c) 1-[2-(4-fluorophenyl)pyrazolo[1,5-b]pyridazin-3-yl]ethanone

In a similar manner as described in Example 62c, from 4-[3-(trifluoromethyl)phenyl]-3-butyn-2-one was obtained the title compound as a brown solid.

¹H-NMR (300 MHz, d⁶-DMSO) δ 8.76 (m, 2H), 8.08-7.62 (m, 5H), 2.32 (s, 3H);

d) 4-[3-(trifluoromethyl)phenyl]-3-butyn-2-one

In a similar manner as described in Example 62d, from 1-ethynyl-3-(trifluoromethyl)benzene was obtained the title compound as a brown solid.

¹H-NMR (300 MHz, d⁶-DMSO) δ 8.01-7.60 (m, 4H), 2.44 (s, 3H); GC-MS (CI) (M+H)⁺ 213.

Example 103

N-(2,3-dihydro-1,4-benzodioxin-6-yl)-4-{2-([3-(trifluoromethyl)phenyl]pyrazolo[1,5-b]pyridazin-3-yl}-2-pyrimidinamine

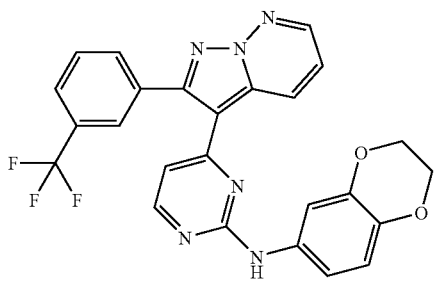

In a similar manner as described in Example 62a, from N-(2,3-dihydro-1,4-benzodioxin-6-yl)guanidinium nitrate was obtained the title compound as a brown solid.

¹H-NMR (300 MHz, d⁶-DMSO) δ 9.43 (s, 1H), 8.75 (d, 1H, J=8.4 Hz), 8.31 (d, 1H, J=5.0 Hz), 7.96-7.70 (m, 5H), 7.39 (d, 1H, J=9.2 Hz), 7.25 (s, 1H), 7.04 (m, 1H), 6.71 (d, 1H, J=8.7 Hz), 6.53 (d, 1H, J=4.8 Hz) 4.19 (brs, 4H); MS ((ESI) (M+H)⁺ 491.

Example 104

N-[3-(trifluoromethyl)phenyl]-4-{2-[3-(trifluoromethyl)phenyl]pyrazolo[1,5-b]pyridazin-3-yl}-2-pyrimidinamine

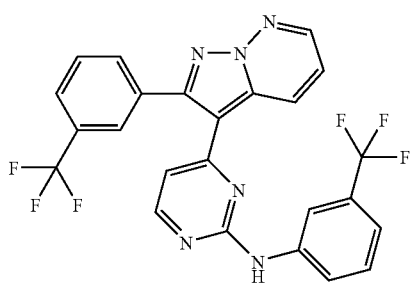

In a similar manner as described in Example 62a, from N-[3-(trifluoromethyl)phenyl]guanidine was obtained the title compound as a brown solid.

¹H-NMR (300 MHz, d⁶-DMSO) δ 10.03 (s, 1H), 8.85 (d, 1H, J=8.8 Hz), 8.68 (m, 1H), 8.45 (d, 1H, J=5.1 Hz), 8.00-7.66 (m, 4H), 7.56-7.21 (m, 4H), 6.70 (d, 1H, J=5.2 Hz); MS (ESI) (M+H)⁺ 500.

Example 105

N-[4-chloro-3-(trifluoromethyl)phenyl]-4-{2-[3-(trifluoromethyl)phenyl]pyrazolo[1,5-b]pyridazin-3-yl}-2-pyrimidinamine

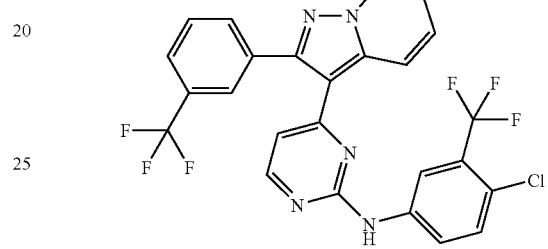

In a similar manner as described in Example 62a, from N-[4-chloro-3-(trifluoromethyl)phenyl]guanidinium nitrate was obtained the title compound as a brown solid.

¹H-NMR (300 MHz, d⁶-DMSO) δ 10.14 (s, 1H), 8.82 (d, 1H, J=8.8 Hz), 8.69 (m, 1H), 8.47 (d, 1H, J=5.1 Hz), 8.31 (s, 1H), 7.99-7.69 (m, 5H), 7.51-7.45 (m, 2H), 6.75 (d, 1H, J=5.2 Hz); MS (ESI) (M+H)⁺ 535.

Example 106

N-(3,4-difluorophenyl)-4-{2-[3-(trifluoromethyl)phenyl]pyrazolo[1,5-b]pyridazin-3-yl}-2-pyrimidinamine

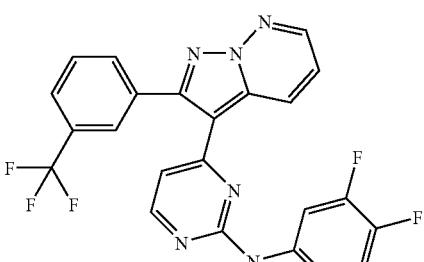

In a similar manner as described in Example 62a, from N-(3,4-difluorophenyl)guanidinium nitrate was obtained the title compound as a brown solid.

¹H-NMR (300 MHz, d⁶-DMSO) δ 9.91 (s, 1H), 8.83 (d, 1H, J=9.2 Hz), 8.70 (s, 1H), 8.48 (d, 1H, J=4.8 Hz), 8.00-7.74 (m, 5H), 7.53 (m, 3H), 6.78 (s, 1H); MS (ESI) (M+H)⁺ 469.

Example 107

4-(6-methyl-2-phenylpyrazolo[1,5-b]pyridazin-3-yl)-N-phenyl-2-pyrimidinamine

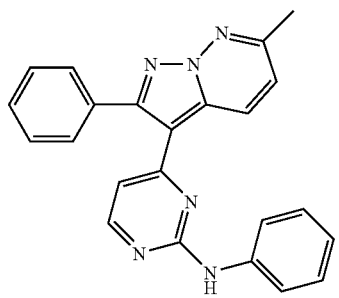

a) In a similar manner as described in Example 62a, from N-phenylguanidinium nitrate was obtained the title compound as a brown solid.

$^1$H-NMR (300 MHz, d$^6$-DMSO) δ 9.60 (s, 1H), 8.81 (d, 1H, J=9.1 Hz), 8.29 (d, 1H, J=5.3 Hz), 7.69-7.21 (m 9H), 6.96 (m, 2H), 6.67 (d, 1H, J=5.1 Hz), 2.59 (s, 3H); MS (ESI) (M+H)$^+$ 379.

b) (2E)-3-(dimethylamino)-1-(6-methyl-2-phenylpyrazolo[1,5-b]pyridazin-3-yl)-2-propen-1-one In a similar manner as described in Example 62b, from 1-(6-methyl-2-phenylpyrazolo[1,5-b]pyridazin-3-yl)ethanone was obtained the title compound as a brown solid.

$^1$H-NMR (300 MHz, d$^6$-DMSO) δ $^1$H-NMR (300 MHz, d$^6$-DMSO) δ 8.56 (m, 2H), 7.74-7.50 (m, 6H), 5.10 (d, 1H, J=12.5 Hz), 3.36 (brs, 3H), 2.52 (brs, 3H); 2.57 (s, 3H); MS (ESI) (M+Na)$^+$ 329.

c) 1-(6-methyl-2-phenylpyrazolo[1,5-b]pyridazin-3-yl)ethanone

In a similar manner as described in Example 62c, from 4-phenyl-3-butyn-2-one and 3-methylpyridazine was obtained the title compound as a brown solid.

$^1$H-NMR (300 MHz, d$^6$-DMSO) δ 8.60 (d, 1H, J=9.2 Hz), 7.69 (m, 2H), 7.56-7.50 (m, 4H), 2.62 (s, 3H), 2.19 (s, 3H).

Example 108

N-(2,3-dihydro-1,4-benzodioxin-6-yl)-4-(6-methyl-2-phenylpyrazolo[1,5-b]pyridazin-3-yl)-2-pyrimidinamine

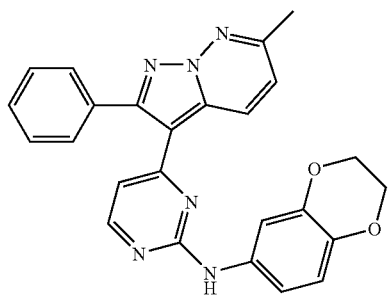

In a similar manner as described in Example 62a, from N-(2,3-dihydro-1,4-benzodioxin-6-yl)guanidinium nitrate was obtained the title compound as a brown solid.

$^1$H-NMR (300 MHz, d$^6$-DMSO) δ 9.41 (s, 1H), 8.83 (d, 1H, J=8.9 Hz), 8.24 (d, 1H, J=5.3 Hz), 7.63-7.31 (m, 6H), 7.11 (d, 1H, J=8.7 Hz), 6.76 (d, 1H, J=8.6 Hz), 6.43 (d, 1H, J=5.3 Hz), 4.21 (brs, 4H), 2.60 (s, 3H); MS (ESI) (M+H)$^+$ 437.

Example 109

4-(6-methyl-2-phenylpyrazolo[1,5-b]pyridazin-3-yl)-N-[3-(trifluoromethyl)phenyl]-2-pyrimidinamine

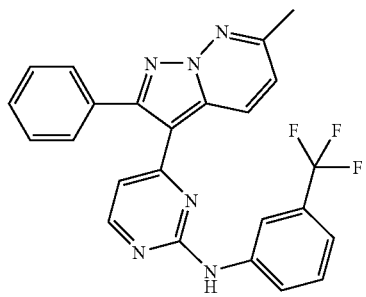

In a similar manner as described in Example 62a, from N-[3-(trifluoromethyl)phenyl]guanidine was obtained the title compound as a brown solid.

$^1$H-NMR (300 MHz, d$^6$-DMSO) δ 9.98 (s, 1H), 8.82 (d, 1H, J=9.1 Hz), 8.36 (m, 1H), 8.23 (s, 1H), 7.96 (d, 1H, J=8.2 Hz), 7.63-7.25 (m, 8H), 6.58 (d, 1H, J=5.2 Hz), 2.60 (s, 3H); MS (ESI) (M+H)$^+$ 447.

Example 110

N-[4-chloro-3-(trifluoromethyl)phenyl]-4-(6-methyl-2-phenylpyrazolo[1,5-b]pyridazin-3-yl)-2-pyrimidinamine

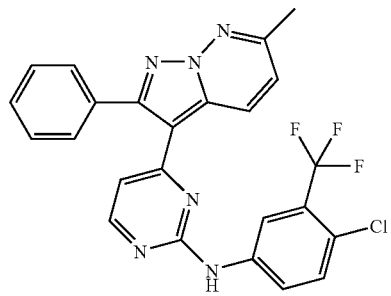

In a similar manner as described in Example 62a, from N-[4-chloro-3-(trifluoromethyl)phenyl]guanidinium nitrate was obtained the title compound as a brown solid.

$^1$H-NMR (300 MHz, d$^6$-DMSO) δ 10.10 (s, 1H), 8.80 (d, 1H, J=9.3 Hz), 8.38 (d, 1H, J=5.3 Hz), 8.32 (s, 1H), 8.01 (d, 1H, J=8.8 Hz), 7.67-7.24 (m, 7H), 6.62 (d, 1H, J=5.4 Hz), 2.60 (s, 3H); MS (ESI) (M+H)$^+$ 481.

Example 111

N-(3,4-difluorophenyl)-4-(6-methyl-2-phenylpyrazolo[1,5-b]pyridazin-3-yl)-2-pyrimidinamine

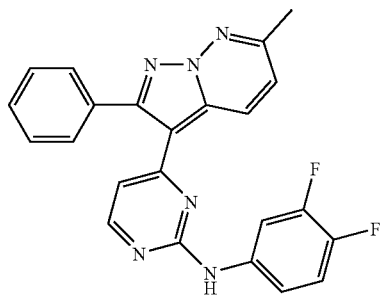

In a similar manner as described in Example 62a, from N-(3,4-difluorophenyl)guanidinium nitrate was obtained the title compound as a brown solid.

$^1$H-NMR (300 MHz, d$^6$-DMSO) δ 9.81 (s, 1H), 8.74 (d, 1H, J=8.8 Hz), 8.31 (m, 1H), 7.91-7.84 (m, 1H), 7.59-7.22 (m, 8H), 6.55 (d, 1H, J=4.7 Hz), 2.58 (s, 3H); MS (ESI) (M+H)$^+$ 415.

Example 112

4-{6-methyl-2-[3-(trifluoromethyl)phenyl]pyrazolo[1,5-b]pyridazin-3-yl}-N-phenyl-2-pyrimidinamine

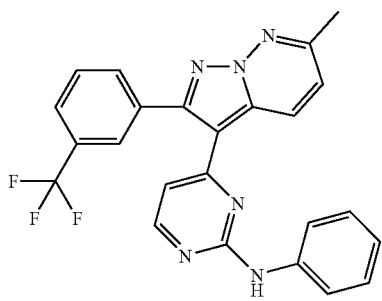

a) In a similar manner as described in Example 62a, from N-phenylguanidinium nitrate was obtained the title compound as a brown solid.

$^1$H-NMR (300 MHz, d$^6$-DMSO) δ 9.92 (s, 1H), 8.70 (d, 1H, J=8.2 Hz), 8.42 (m, 1H), 8.34-7.19 (m, 10H), 6.66 (d, 1H, J=5.1 Hz), 2.61 (s, 3H); MS (ESI) (M+H)$^+$ 447.

b) (2E)-3-(dimethylamino)-1-{6-methyl-2-[3-(trifluoromethyl)phenyl]pyrazolo[1,5-b]pyridazin-3-yl}-2-propen-1-one In a similar manner as described in Example 62b, from 1-{6-methyl-2-[3-(trifluoromethyl)phenyl]pyrazolo[1,5-b]pyridazin-3-yl}ethanone was obtained the title compound as a brown solid.

$^1$H-NMR (300 MHz, d$^6$-DMSO) δ 8.53 (m, 1H), 7.98 (m, 2H), 7.76 (m, 2H), 7.50 (m, 1H), 7.32 (m, 1H), 5.05 (d, 1H, J=12.5 Hz), 2.97 (brs, 3H), 2.51 (brs, 3H), (2.58 s, 3H)

c) 1-{6-methyl-2-[3-(trifluoromethyl)phenyl]pyrazolo[1,5-b]pyridazin-3-yl}ethanone In a similar manner as described in Example 62c, from 4-[3-(trifluoromethyl)phenyl]-3-butyn-2-one was obtained the title compound as a brown solid.

$^1$H-NMR (300 MHz, d$^6$-DMSO) δ 8.63 (d, 1H, J=9.4 Hz), 8.06 (m, 2H), 7.93 (m, 1H), 7.81 (m, 1H), 7.56 (d, 1H, J=9.2 Hz), 2.63 (s, 3H), 2.31 (s, 3H); MS (ESI) (M+H)$^+$ 320.

Example 113

4-{6-methyl-2-[3-(trifluoromethyl)phenyl]pyrazolo[1,5-b]pyridazin-3-yl}-N-[3-(trifluoromethyl)phenyl]-2-pyrimidinamine

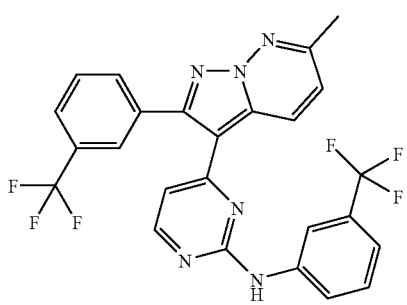

In a similar manner as described in Example 62a, from N-[3-(trifluoromethyl)phenyl]guanidine was obtained the title compound as a brown solid.

$^1$H-NMR (300 MHz, d$^6$-DMSO) δ 9.61 (s, 1H), 8.72 (d, 1H, J=9.1 Hz), 8.35 (d, 1H, J=5.1 Hz), 8.03-7.48 (m, 6H), 7.37 (d, 1H, J=9.2 Hz), 7.22 (t, 1H, J=7.6 Hz), 6.94 (t, 1H, J=7.1 Hz), 6.59 (d, 1H, J=5.1 Hz), 2.58 (s, 3H); MS (ESI) (M+H)$^+$ 515.

Example 114

N-[4-chloro-3-(trifluoromethyl)phenyl]-4-{6-methyl-2-[3-(trifluoromethyl)phenyl]pyrazolo[1,5-b]pyridazin-3-yl}-2-pyrimidinamine

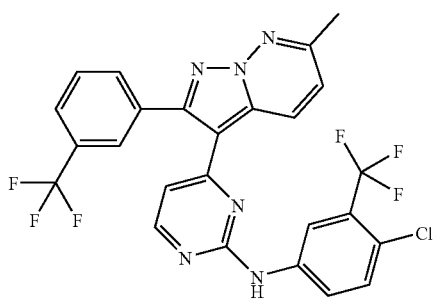

In a similar manner as described in Example 62a, from N-[4-chloro-3-(trifluoromethyl)phenyl]guanidinium nitrate was obtained the title compound as a brown solid.

$^1$H-NMR (300 MHz, d$^6$-DMSO) δ 10.10 (s, 1H), 8.70 (d, 1H, J=9.2 Hz), 8.44 (d, 1H, J=5.1 Hz), 8.28 (m, 1H), 7.96-

7.53 (m, 6H), 7.49 (d, 1H, J=8.8 Hz), 7.40 (d, 1H, J=9.2 Hz), 6.72 (d, 1H, J=5.3), 2.61 (s, 3H); MS (ESI) (M+H)+ 549.

Example 115

N-(3,4-difluorophenyl)-4-{6-methyl-2-[3-(trifluoromethyl)phenyl]pyrazolo[1,5-b]pyridazin-3-yl}-2-pyrimidinamine

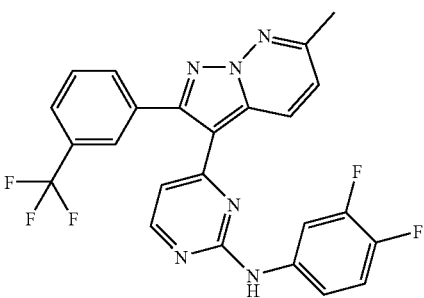

In a similar manner as described in Example 62a, from N-(3,4-difluorophenyl)guanidinium nitrate was obtained the title compound as a brown solid.

$^1$H-NMR (300 MHz, d$^6$-DMSO) δ 9.85 (s, 1H), 8.68 (d, 1H, J=9.1 Hz), 8.42 (d, 1H, J=5.2 Hz), 7.94-7.69 (m, 5H), 7.41 (d, 1H, J=9.2 Hz), 7.29 (m, 2H), 6.72 (d, 1H, J=5.1 Hz); MS (ESI) (M+H)+ 483.

Example 116

N-(2,3-dihydro-1,4-benzodioxin-6-yl)-4-{6-methyl-2-[3-(trifluoromethyl)phenyl]pyrazolo[1,5-b]pyridazin-3-yl}-2-pyrimidinamine

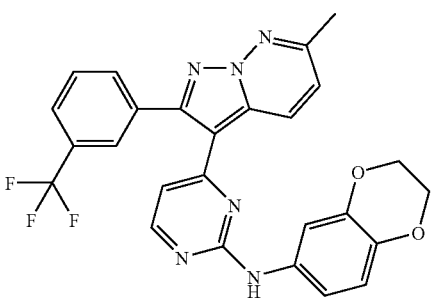

In a similar manner as described in Example 62a, from N-(2,3-dihydro-1,4-benzodioxin-6-yl)guanidinium nitrate was obtained the title compound as a brown solid.

$^1$H-NMR (300 MHz, d$^6$-DMSO) δ 9.43 (s, 1H), 8.74 (d, 1H, J=8.3 Hz), 8.30 (d, 1H, J=5.0 Hz), 7.96-7.70 (m, 4H), 7.39 (d, 1H, J=9.2 Hz), 7.25 (s, 1H), 7.04 (d, 1H, J=8.0 Hz), 6.70 9d, 1H, J=8.6 Hz), 6.53 (d, 1H, J=5.0 Hz), 4.19 (brs, 4H), 2.60 (s, 3H); MS (ESI) (M+H)+ 505.

Example 117

4-[2-(4-fluorophenyl)-6-methylpyrazolo[1,5-b]pyridazin-3-yl]-N-phenyl-2-pyrimidinamine

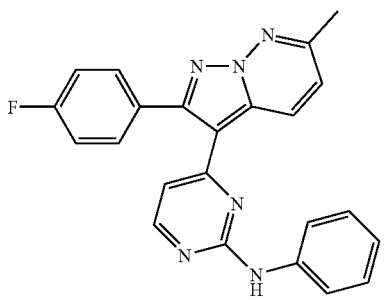

a) In a similar manner as described in Example 62a, from N-phenylguanidinium nitrate was obtained the title compound as a brown solid.

$^1$H-NMR (300 MHz, d$^6$-DMSO) δ 9.43 (s, 1H), 8.77 (d, 1H, J=9.2 Hz), 8.32 (d, 1H, J=5.2 Hz), 7.68 (m, 3H), 7.37 (m, 6H), 6.95 (t, 1H, J=7.3 Hz), 6.55 (d, 1H, J=5.3 Hz), 2.58 (s, 3H); MS (ESI) (M+H)+ 397.

b) (2E)-3-(dimethylamino)-1-[2-(4-fluorophenyl)-6-methylpyrazolo[1,5-b]pyridazin-3-yl]-2-propen-1-one In a similar manner as described in Example 62b, from 1-[2-(4-fluorophenyl)-6-methylpyrazolo[1,5-b]pyridazin-3-yl]ethanone was obtained the title compound as a brown solid.

$^1$H-NMR (300 MHz, d$^6$-DMSO) δ 8.39 (d, 1H, J=9.2 Hz), 7.75-7.51 (m, 2H), 7.33-7.25 (m, 3H), 5.06 (d, 1H, J=12.5 Hz), 3.02 (brs, 3H), 2.54 (brs, 3H), 2.48 (s, 3H); MS (ESI) (M+H)+ 325.

c) 1-[2-(4-fluorophenyl)-6-methylpyrazolo[1,5-b]pyridazin-3-yl]ethanone

In a similar manner as described in Example 62c, from 1-[2-(4-fluorophenyl)pyrazolo[1,5-b]pyridazin-3-yl]ethanone was obtained the title compound as a brown solid.

$^1$H-NMR (300 MHz, d$^6$-DMSO) δ 8.56 (d, 1H, J=9.2 Hz), 7.72 (m, 2H), 7.50 (d, 1H, J=9.3 Hz), 7.37 (m, 2H), 2.58 9s, 3H), 2.19 (m, 3H); MS (ESI) (M+H)+ 270.

Example 118

N-(2,3-dihydro-1,4-benzodioxin-6-yl)-4-[2-(4-fluorophenyl)-6-methylpyrazolo[1,5-b]pyridazin-3-yl]-2-pyrimidinamine

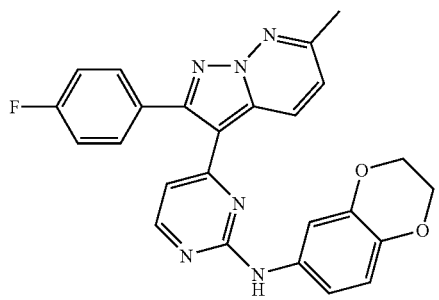

In a similar manner as described in Example 62a, from N-(2,3-dihydro-1,4-benzodioxin-6-yl)guanidinium nitrate was obtained the title compound as a brown solid.

$^1$H-NMR (300 MHz, d$^6$-DMSO) δ 9.41 (s, 1H), 8.78 (d, 1H, J=8.6 Hz), 8.26 (d, 1H, J=5.2 Hz), 7.67 (m, 2H), 7.35-7.28 (m, 4H), 7.08 (m, 1H), 6.73 (d, 1H, J=8.8 Hz), 6.46 (d, 1H, J=5.3 Hz), 4.19 (brs, 4H), 2.58 (s, 3H); MS (ESI) (M+H)$^+$ 455.

Example 119

4-[2-(4-fluorophenyl)-6-methylpyrazolo[1,5-b]pyridazin-3-yl]-N-[3-(trifluoromethyl)phenyl]-2-pyrimidinamine

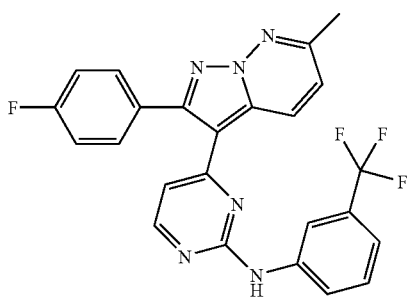

In a similar manner as described in Example 62a, from N-[3-(trifluoromethyl)phenyl]guanidine was obtained the title compound as a brown solid.

$^1$H-NMR (300 MHz, d$^6$-DMSO) δ 9.98 (s, 1H), 8.77 (d, 1H, J=9.4 Hz), 8.38 (d, 1H, J=5.3 Hz), 7.93 (d, 1H, J=8.2 Hz), 7.69-7.64 (m, 2H), 7.48-7.24 (m, 5H), 6.59 (d, 1H J=5.4 Hz), 2.59 (s, 3H); MS (ESI) (M+H)$^+$ 465.

Example 120

N-[4-chloro-3-(trifluoromethyl)phenyl]-4-[2-(4-fluorophenyl)-6-methylpyrazolo[1,5-b]pyridazin-3-yl]-2-pyrimidinamine

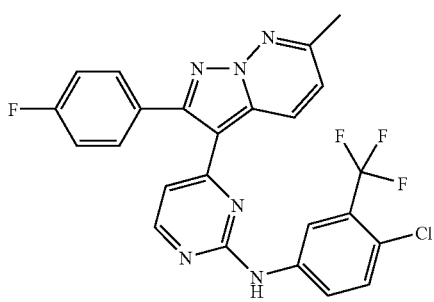

In a similar manner as described in Example 62a, from N-[4-chloro-3-(trifluoromethyl)phenyl]guanidinium nitrate was obtained the title compound as a brown solid.

$^1$H-NMR (300 MHz, d$^6$-DMSO) δ 10.09 (s, 1H), 8.75 (d, 1H, J=9.2 Hz), 8.39 (m, 1H), 8.30 (s, 1H), 7.99 (d, 1H, J=8.8 Hz), 7.68-7.52 (m, 3H), 7.38-7.29 (m, 3H), 6.63 (d, 1H J=5.3 Hz), 2.59 (s, 3H); MS (ESI) (M+H)$^+$ 499.

Example 121

N-(3,4-difluorophenyl)-[2-(4-fluorophenyl)-6-methylpyrazolo[1,5-b]pyridazin-3-yl]-2-pyrimidinamine

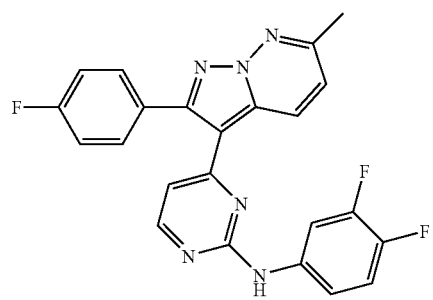

In a similar manner as described in Example 62a, from N-(3,4-difluorophenyl)guanidinium nitrate was obtained the title compound as a brown solid.

$^1$H-NMR (300 MHz, d$^6$-DMSO) δ 9.84 (s, 1H), 8.73 (d, 1H, J=9.1 Hz), 8.37 (d, 1H, J=5.3 Hz), 7.88-7.82 (m, 1H), 7.67-7.62 (m, 2H), 7.39-7.23 (m, 5H), 6.62 (d, 1H J=5.2 Hz), 2.58 (s, 3H); MS (ESI) (M+H)$^+$ 433.

Example 122

4-(2-cyclopropylpyrazolo[1,5-b]pyridazin-3-yl)-N-phenylpyrimidin-2-amine (122)

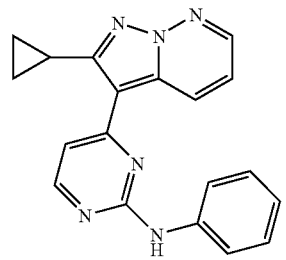

a) In a similar manner as described in 62a, from N-phenylguanidinium nitrate was obtained the title compound as a brown solid. $^1$H-NMR (300 MHz, d$^6$-DMSO) ppm: 9.62 (s, 1H), 8.96 (d, J=9.1 Hz, 1H), 8.56 (m, 2H), 7.83 (d, J=7.7 Hz, 2H), 7.41-7.31 (m, 5H), 2.68 (m, 1H), 1.21-1.05 (m, 4H); MS (ESI) (M+H)$^+$ 329.

b) (2E)-1-(2-cyclopropylpyrazolo[1,5-b]pyridazin-3-yl)-3-(dimethylamino)prop-2-en-1-one In a similar manner as described in 62b, from Example 122c was obtained the title compound as a brown solid. $^1$H-NMR (300 MHz, d$^6$-DMSO) ppm: 8.55 (m, 2H), 7.75 (d, J=12.3 Hz, 1H), 7.36 (dd, J=9, 9 Hz, 1H), 5.75 (d, J=12.4 Hz, 1H), 3.17 (brs, 3H), 2.92 (brs, 3H), 2.69 (m, 1H), 2.53 (s, 3H), 1.14-1.11 (m, 4H); MS (ESI) (M+H)$^+$ 257.

c) 1-(2-cyclopropylpyrazolo[1,5-b]pyridazin-3-yl)ethanone

In a similar manner as described in Example 62c, from 4-cyclopropylbut-3-yn-2-one was obtained the title compound as a brown solid. $^1$H-NMR (300 MHz, d$^6$-DMSO)

ppm: 8.63 (m, 2H), 7.54 (dd, J=8.9, 8.7 Hz, 1H), 2.95 (m, 1H), 2.68 (s, 3H), 1.14-1.04 (m, 4H); MS (ESI) (M+H)+ 202.

d) 4-cyclopropylbut-3-yn-2-one

In a similar manner as described in Example 62d, by the reaction of cyclopropyl acetylene with acetic anhydride was obtained the title compound as a colorless oil after column chromatography with Hexane/ethylacetate (9:1) to afford the title compound in 64% yield.

$^1$H-NMR (300 MHz, CDCl$_3$) ppm: 2.31 (s, 3H), 1.46-1.26 (m, 1H), 1.02-0.90 (m, 4H); GC-MS (M+H)+ 109.

Example 123

4-(2-cyclopropylpyrazolo[1,5-b]pyridazin-3-yl)-N-(3,4-difluorophenyl)pyrimidin-2-amine

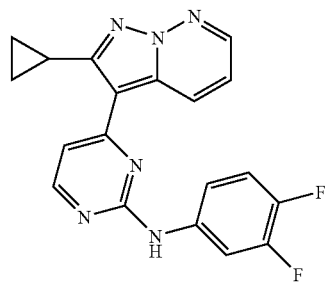

In a similar manner as described in 62a, from N-(3,4-difluorophenyl)guanidinium nitrate was obtained the title compound as a brown solid.

$^1$H-NMR (300 MHz, d$^6$-DMSO) ppm: 9.86 (s, 1H), 8.91 (d, J=7.9 Hz, 1H), 8.60 (d, J=5.4 Hz, 1H), 8.56 (d, J=6.3 Hz, 1H), 8.12 (m, 1H), 7.52-7.35 (m, 4H), 2.69 (m, 1H), 1.23-1.08 (m, 4H); MS (ESI) (M+H)+ 365.

Example 124

4-(2-cyclohexylpyrazolo[1,5-b]pyridazin-3-yl)-N-phenylpyrimidin-2-amine

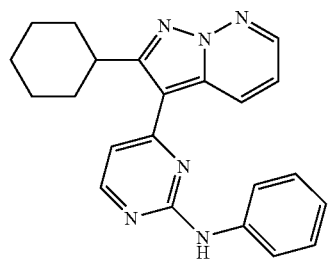

4-(2-cyclohexylpyrazolo[1,5-b]pyridazin-3-yl)-N-phenylpyrimidin-2-amine (124)

a) In a similar manner as described in 62a, from N-phenylguanidinium nitrate was obtained the title compound as a brown solid. $^1$H-NMR (300 MHz, d$^6$-DMSO) ppm: 9.61 (s, 1H), 8.82 (d, J=8.7 Hz, 1H), 8.56 (m, 2H), 7.81 (d, J=7.8 Hz, 2H), 7.39-7.30 (m, 3H), 7.09-6.98 (m, 2H), 3.52 (m, 1H), 2.30-1.28 (m, 10H); MS (ESI) (M+H)+ 371.

b) (2E)-1-(2-cyclohexylpyrazolo[1,5-b]pyridazin-3-yl)-3-(dimethylamino)prop-2-en-1-one In a similar manner as described in 62b, from Example 123c was obtained the title compound as a brown solid. $^1$H-NMR (300 MHz, d$^6$-DMSO) ppm: 8.51 (m, 2H), 7.73 (d, J=12.3 Hz, 1H), 7.36 (dd, J=8.9, 8.9 Hz, 1H), 5.48 (d, J=12.2 Hz, 1H), 3.42 (m, 1H), 3.16 (brs, 3H), 2.92 (brs, 3H), 2.14-1.38 (m, 10H); MS (ESI) (M+H)+ 299.

c) 1-(2-cyclohexylpyrazolo[1,5-b]pyridazin-3-yl)ethanone

In a similar manner as described in Example 62c, from 4-cyclohexylbut-3-yn-2-one was obtained the title compound as a brown solid. $^1$H-NMR (300 MHz, d$^6$-DMSO) ppm: 8.65 (m, 2H), 7.55 (dd, J=9.0, 9.0 Hz, 1H), 3.44 (m, 1H), 2.63 (s, 3H), 2.0-1.31 (m, 10H); MS (ESI) (M+H)+ 244.

d) 4-cyclohexylbut-3-yn-2-one

In a similar manner as described in Example 62d, by the reaction of cyclohexyl acetylene with acetic anhydride was obtained the title compound as a colorless oil after column chromatography with Hexane/ethylacetate (9:1) to afford the title compound in 35% yield. $^1$H-NMR (300 MHz, CDCl$_3$) ppm: 2.32 (s, 3H), 1.96-1.26 (m, 11H); GC-MS (M+H)+ 151.

Example 125

4-(2-cyclohexylpyrazolo[1,5-b]pyridazin-3-yl)-N-(3,4-difluorophenyl)pyrimidin-2-amine

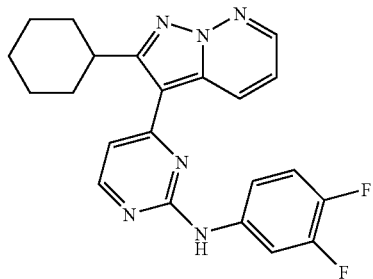

In a similar manner as described in 62a, from N-(3,4-difluorophenyl)guanidinium nitrate was obtained the title compound as a brown solid. $^1$H-NMR (300 MHz, d$^6$-DMSO) ppm: 9.85 (s, 1H), 8.80 (d, J=9.1 Hz, 1H), 8.60 (d, J=5.2 Hz, 1H), 8.57-8.55 (m, 1H), 8.15-8.05 (m, 1H), 7.47-7.37 (m, 3H), 7.14 (d, J=5.2 Hz, 1H), 3.41 (m, 1H), 2.02-1.25 (m, 10H); MS (ESI) (M+H)+ 407.

BIOLOGICAL DATA

The compounds of the present invention have valuable pharmacologic properties. As described in more detail below, each of the compounds were tested for activity as GSK-3 inhibitors. Each of the compounds described in the above examples demonstrated significant activity as GSK-3 inhibitors. More specifically, each of the compounds described in the above examples demonstrated a pIC$_{50}$ of >5.0.

The protocol used to demonstrate the pharmacological response of the present invention is based on the ability of the kinase to phosphorylate a biotinylated peptide, the sequence of which is derived from the phosphorylation site of glycogen synthase and its sequence is: Biotin-Ahx-AAAKRREILSR-RPS(PO$_3$)YR-amide. The phosphorylated biotinylated peptide is then captured onto streptavidin coated scintillation proximity assay (SPA) beads from Amersham Technology, where the signal from the $^{33}$P is amplified via the scintillant contained in the beads.

GSK-3β is commercially available or may be cloned and expressed in *E coli* using standard techniques to produce soluble, active protein. The production of active protein involves purification in two steps using Metal Chelate and Ion Exchange Chromatography. Protein eluting from Ion Exchange provides >90% pure product that may then be concentrated for use in high throughput screening.

The kinase was assayed at a concentration of 20 nM final in 100 mM HEPES, pH 7.2 containing 10 mM magnesium chloride, 0.1 mg/mL bovine serum albumin, 1 mM dithiothreitol, 0.3 mg/mL heparin, 2.8 uM peptide substrate, 2.5 uM ATP, and 0.2 uCi/well γ$^{33}$P]-ATP. After 40 minutes incubation at room temperature, the reaction was stopped by addition of 100 mM EDTA and 1 mM solution in 100 mM HEPES, pH 7.2 followed by an additional solution of diluted Streptavidin coated SPA beads in PBS, pH 7.2 to give a final concentration of 0.25 mg of beads per assay well in a 96-well microtiter plate.

10 mM stock solutions of the compounds of the invention in 100% DMSO are generated as a first step in the screening process. The second step involves the creation of dose response plates where these compounds are diluted 10-fold in 100% DMSO to 1 mM concentrations and subsequently serially diluted 3-fold in 100% DMSO across the plate by automated liquid handling such that the final top concentration of inhibitor is 0.033 mM in the 30 uL kinase assay. The third step involves the creation of the assay plates. This is achieved by transferring 1 uL of the compounds to assay plates by automated liquid handling. The fourth step is to perform the assay as described and count the resulting plates in the Packard TopCount NXT microplate scintillation and luminescence counter.

The final step is data acquisition and analysis where IC$_{50}$ values are generated for each compound by normalizing curve data to the equation $100*(U1-C2)/(C1-C_2)$ (where U1 is the cpm value, C2 is the background, and C1 is the maximum number of counts), then fitting the normalized data to the equation $y=Vmax*(1-(x/(K+x)))$. The IC$_{50}$ values were converted to pIC$_{50}$ values, i.e., $-\log$ IC$_{50}$ in Molar concentration.

Test compounds are employed in free or salt form.

All research complied with the principles of laboratory animal care (NIH publication No. 85-23, revised 1985) and GlaxoSmithKline policy on animal use.

Although specific embodiments of the present invention have been illustrated and described in detail, the invention is not limited thereto. The above detailed description of preferred embodiments is provided for example only and should not be construed as constituting any limitation of the invention. Modifications will be obvious to those skilled in the art, and all modifications that do not depart from the spirit of the invention are intended to be included within the scope of the appended claims.

What is claimed is:

1. A compound of Formula (I):

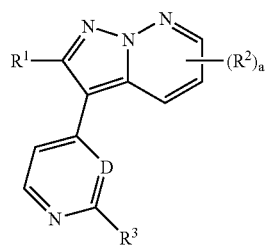

(I)

or a salt thereof, wherein

D is N;

R$^1$ is phenyl, where said phenyl may be optionally substituted one or more times with C$_1$-C$_6$ alkyl, C$_1$-C$_6$ alkoxy, halogen, or C$_1$-C$_6$ haloalkyl, a is 1 or 2;

y is 0, 1, or 2;

R$^2$ is hydrogen, C$_1$-C$_6$ alkyl, C$_1$-C$_6$ alkenyl, C$_1$-C$_6$ alkynyl, C$_1$-C$_6$ haloalkyl, C$_3$-C$_7$ cycloalkyl, halogen, tetrahydrofuranyl, pyranyl, 1,4-dioxanyl, 1,3-dioxanyl, piperidinyl, pyrrolidinyl, morpholinyl, tetrahydrothiopyranyl, tetrahydrothiophenyl, aryl, furanyl, thiophenyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyrazinyl, pyrimidinyl, quinolinyl, isoquinolinyl, benzofuranyl, benzothiophenyl, indolyl, indazolyl, cyano, azido, nitro, —OR$^8$, —OR$^6$R$^8$, —R$^6$R$^7$, —R$^6$R", S(O)$_y$R$^7$, —C(O)R$^7$, —C(O)OR$^7$, —C(O)NR$^4$R$^5$, —NR'(C=NR$^4$)NR$^4$R$^5$, —OC(O)NR$^4$R$^5$, —OC(O)OR$^7$, —C(=NR$^4$)NR$^4$R$^5$, —NR$^4$R$^5$, —OC(O)R$^7$, or —NR$^7$C(O)R$^7$;

R$^3$ is -(Q)$_p$-(Q$^1$)
where
Q is O, N(R$^8$) or S(O)$_y$,
p is 0 or 1,
y is 0, 1, or 2, and
Q$^1$ is C$_1$-C$_6$alkyl, C$_3$-C$_7$cycloalkyl, C$_1$-C$_6$haloalkyl, aryl, aryl substituted with —C(O)N(H)R$^6$NR$^4$R$^5$ or —OC(H)(OH)R$^6$NR$^4$R$^5$, furanyl, thiophenyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, quinolinyl, isoquinolinyl, benzofuranyl, benzothiophenyl, indolyl, indazolyl, aralkyl, or —R$^6$NR$^4$R$^5$;

R$^4$ and R$^5$ are independently hydrogen, C$_1$-C$_3$ alkyl, C$_3$-C$_7$ cycloalkyl, or R$^4$ and R$^5$ together with the nitrogen atom to which they are bound form piperidinyl, pyrrolidinyl, morpholinyl, or tetrahydrothiophenyl;

R$^6$ is alkylene, arylene, furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3,4-thiazole-2,5-diyl, pyridine-2,4-diyl, pyridine-2,3-diyl, pyridine-2,5-diyl, pyrimidine-2,4-diyl, quinoline-2,3-diyl, cycloalkylene, alkenylene, cycloalkenylene, or alkynylene;

R$^7$ is hydrogen, C$_1$-C$_6$alkyl, C$_1$-C$_6$alkenyl, C$_1$-C$_6$alkynyl, —NR$^4$R$^5$, aryl, aralkyl, heteroaryl, cycloalkyl, heterocyclyl, —S(O)$_y$R$^8$, —C(O)R$^8$, —C(O)OR$^8$, —C(O)NR$^4$R$^5$, —S(O)$_2$NR$^4$R$^5$, —NR'(C=NR$^4$)NR$^4$R$^5$, —OC(O)NR$^4$R$^5$, —OC(O)OR$^8$, —C(=NR$^4$)NR$^4$R$^5$, —NR$^4$R$^5$, or —NR$^7$C(O)R$^7$ R$^8$ is hydrogen, C$_1$-C$_6$ alkyl, C$_1$-C$_6$ alkenyl, C$_1$-C$_6$ alkynyl, —NR$^4$R$^5$, aryl, aralkyl, heteroaryl, cycloalkyl, tetrahydrofuranyl, pyranyl, 1,4-dioxanyl, 1,3-dioxanyl, piperidinyl, pyrrolidinyl, morpholinyl, tetrahydrothiopyranyl, tetrahydrothiophenyl, or —S(O)$_2$R$^9$;

R$^9$ is C$_1$-C$_6$ alkyl or C$_1$-C$_6$ haloalkyl;

R' is C$_1$-C$_3$ alkylene; and

R" is —OR$^7$, —OC(O)NR$^4$R$^5$, —OC(O)OR$^7$, —OC(O)R$^7$.

2. The compound of claim 1 wherein R$^1$ is phenyl is substituted in the para position with C$_1$-C$_6$ alkyl, C$_1$-C$_6$ alkoxy, halogen, or C$_1$-C$_6$ haloalkyl.

3. The compound of claim 1 wherein R$^3$ is further defined wherein Q is N(R$^8$), where R$^8$ is H, p is 1, and Q$^1$ is aryl optionally substituted with —C(O)N(H)R$^6$NR$^4$R$^5$ or —OC(H)OH R$^6$NR$^4$R$^5$, furanyl, thiophenyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, quinolinyl, isoquinolinyl, benzofuranyl, benzothiophenyl, indolyl, indazolyl, aralkyl, or —R⁶NR⁴R⁵.

4. The compound of claim 3 wherein Q¹ is phenyl optionally substituted with —C(O)N(H)R⁶NR⁴R⁵ or —OC(H)(OH)R⁶NR⁴R⁵, furanyl, thiophenyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, quinolinyl, isoquinolinyl, benzofuranyl, benzothiophenyl, indolyl, indazolyl, aralkyl, or —R⁶NR⁴R⁵.

5. The compound of claim 4 wherein Q¹ is phenyl substituted in the meta or para position with —C(O)N(H)R⁶NR⁴R⁵ or —OC(H)(OH)R⁶NR⁴R⁵, furanyl, thiophenyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, quinolinyl, isoquinolinyl, benzofuranyl, benzothiophenyl, indolyl, indazolyl, aralkyl, or —R⁶NR⁴R⁵.

6. A pharmaceutical composition, comprising: a compound as claimed in claim 1, or a salt thereof and one or more of pharmaceutically acceptable carriers, diluents and excipients.

7. A compound of claim 1 selected of from the group consisting of:
- 4-[2(4-methoxyphenyl)pyrazolo[1,5-b]pyridazin-3-yl]-N-phenylpyrimidin-2-amine;
- 4-[2(4-methoxyphenyl)pyrazolo[1,5-b]pyridazin-3-yl]-N-[3-(trifluoromethyl)phenyl]pyrimidin-2amine;
- N-(3,4-difluorophenyl)-4-[2-(4-methoxyphenyl)pyrazolo[1,5-b]pyridazin-3-yl]pyrimidin-2-amine;
- N-(2,3-dihydro-1,4-benzodioxin-6-yl)-4-[2-(4-methoxyphenyl)pyrazolo[1,5-b]pyridazin-3-yl]pyrimidin-2-amine;
- N-[4-chloro-3-(trifluoromethyl)phenyl]-4-[2-(4-methoxyphenyl)pyrazolo[1,5-b]pyridazin-3-yl]pyrimidin-2-amine;
- N-phenyl-4-{2-[4-(trifluoromethyl)phenyl]pyrazolo[1,5-b]pyridazin-3-yl}pyrimidin-2-amine;
- N-[3-(trifluoromethyl)phenyl]-4-{2-[4-(trifluoromethyl)phenyl]pyrazolo[1,5-b]pyridazin-3-yl}pyrimidin-2-amine;
- N-(3,4-difluorophenyl)-4-{2-[4-(trifluoromethyl)phenyl]pyrazolo[1,5-b]pyridazin-3-yl}pyrimidin-2-amine;
- N-(2,3-dihydro-1,4-benzodioxin-6-yl)-4-{2-[4-(trifluoromethyl)phenyl]pyrazolo[1,5-b]pyridazin-3-yl}pyrimidin-2-amine;
- N-[4-chloro-3-(trifluoromethyl)phenyl]-4-{2-[4-(trifluoromethyl)phenyl]pyrazolo[1,5-b]pyridazin-3-yl}pyrimidin-2-amine;
- 4-[2-(4-chlorophenyl)pyrazolo[1,5-b]pyridazin-3-yl]-N-phenylpyrimidin-2-amine;
- 4-[2-(4-chlorophenyl)pyrazolo[1,5-b]pyridazin-3-yl]-N-[3-(trifluoromethyl)phenyl]pyrimidin-2-amine;
- 4-[2-(4-chlorophenyl)pyrazolo[1,5-b]pyridazin-3-yl]-N-(3,4-difluorophenyl)pyrimidin-2-amine;
- 4-[2-(4-chlorophenyl)pyrazolo[1,5-b]pyridazin-3-yl]-N-(2,3-dihydro-1,4-benzodioxin-6-yl)pyrimidin-2-amine;
- 4-[2-(4-chlorophenyl)pyrazolo[1,5-b]pyridazin-3-yl]-N-[4-chloro-3-(trifluoromethyl)phenyl]pyrimidin-2-amine;
- 4-{6-methyl-2-[4-(trifluoromethyl)phenyl]pyrazolo[1,5-b]pyridazin-3-yl}-N-phenylpyrimidin-2-amine;
- N-(2,3-dihydro-1,4-benzodioxin-6-yl)-4-[6-methyl-2-(4-methylphenyl)pyrazolo[1,5-b]pyridazin-3-yl]pyrimidin-2-amine;
- N-phenyl-4-(2-phenylpyrazolo[1,5-b]pyridazin-3-yl)-2-pyrimidinamine;
- 4-(2-phenylpyrazolo[1,5-b]pyridazin-3-yl)-N-[3-(trifluoromethyl)phenyl]-2-pyrimidinamine;
- N-[4-chloro-3-(trifluoromethyl)phenyl]-4-(2-phenylpyrazolo[1,5-b]pyridazin-3-yl)-2-pyrimidinamine;
- N-(2,3-dihydro-1,4-benzodioxin-6-yl)-4-(2-phenylpyrazolo[1,5-b]pyridazin-3-yl)-2-pyrimidinamine;
- N-(3,5-difluorophenyl)-4-(2-phenylpyrazolo[1,5-b]pyridazin-3-yl)-2-pyrimidinamine;
- N-(3,4-difluorophenyl)-4-(2-phenylpyrazolo[1,5-b]pyridazin-3-yl)-2-pyrimidinamine;
- 4-[2-(4-fluorophenyl)pyrazolo[1,5-b]pyridazin-3-yl]-N-phenyl-2-pyrimidinamine;
- N-(2,3-dihydro-1,4-benzodioxin-6-yl)-4-[2-(4-fluorophenyl)pyrazolo[1,5-b]pyridazin-3-yl]-2-pyrimidinamine;
- 4-[2-(4-fluorophenyl)pyrazolo[1,5-b]pyridazin-3-yl]-N-[3-(trifluoromethyl)phenyl]-2-pyrimidinamine;
- N-[4-chloro-3-(trifluoromethyl)phenyl]-4-[2-(4-fluorophenyl)pyrazolo[1,5-b]pyridazin-3-yl]-2-pyrimidinamine;
- N-(3,4-difluorophenyl)-4-[2-(4-fluorophenyl)pyrazolo[1,5-b]pyridazin-3-yl]-2-pyrimidinamine;
- N-phenyl-4-{2-[3-(trifluoromethyl)phenyl]pyrazolo[-1,5-b]pyridazin-3-yl}-2-pyrimidinamine;
- N-(2,3-dihydro-1,4-benzodioxin-6-yl)-4-{2-[3-(trifluoromethyl)phenyl]pyrazolo[1,5-b]pyridazin-3-yl}-2-pyrimidinamine;
- N-[3-(trifluoromethyl)phenyl]-4-{2-[3-(trifluoromethyl)phenyl]pyrazolo[1,5-b]pyridazin-3-yl}-2-pyrimidinamine;
- N-[4-chloro-3-(trifluoromethyl)phenyl]-4-{2-[3-(trifluoromethyl)phenyl]pyrazolo[1,5-b]pyridazin-3-yl}-2-pyrimidinamine;
- N-(3,4-difluorophenyl)-4-{2-[3-(trifluoromethyl)phenyl]pyrazolo[1,5-b]pyridazin-3-yl}-2-pyrimidinamine;
- 4-(6-methyl-2-phenylpyrazolo[1,5-b]pyridazin-3-yl)-N-phenyl-2-pyrimidinamine;
- N-(2,3-dihydro-1,4-benzodioxin-6-yl)-4-(6-methyl-2-phenylpyrazolo[1,5-b]pyridazin-3-yl)-2-pyrimidinamine;
- 4-(6-methyl-2-phenylpyrazolo[1,5-b]pyridazin-3-yl)-N-[3-(trifluoromethyl)phenyl]-2-pyrimidinamine;
- N-[4-chloro-3-(trifluoromethyl)phenyl]-4-(6-methyl-2-phenylpyrazolo[1,5-b]pyridazin-3-yl)-2-pyrimidinamine;
- N-(3,4-difluorophenyl)-4-(6-methyl-2-phenylpyrazolo[1,5-b]pyridazin-3-yl)-2-pyrimidinamine;
- 4-{6-methyl-2-[3-(trifluoromethyl)phenyl]pyrazolo[1,5-b]pyridazin-3-yl}-N-phenyl-2-pyrimidinamine;
- 4-{6-methyl-2-[3-(trifluoromethyl)phenyl]pyrazolo[1,5-b]pyridazin-3-yl}-N-[3-(trifluoromethyl)phenyl]-2-pyrimidinamine;
- N-[4-chloro-3-(trifluoromethyl)phenyl]-4-{6-methyl-2-[3-(trifluoromethyl)phenyl]pyrazolo[1,5-b]pyridazin-3-yl}-2-pyrimidinamine;
- N-(3,4-difluorophenyl)-4-{6-methyl-2-[3-(trifluoromethyl)phenyl]pyrazolo[1,5-b]pyridazin-3-yl}-2-pyrimidinamine;
- N-(2,3-dihydro-1,4-benzodioxin-6-yl)-4-{6-methyl-2-[3-(trifluoromethyl)phenyl]pyrazolo[1,5-b]pyridazin-3-yl}-2-pyrimidinamine;
- 4-[2-(4-fluorophenyl)-6-methylpyrazolo[1,5-b]pyridazin-3-yl]-N-phenyl-2-pyrimidinamine;

N-(2,3-dihydro-1,4-benzodioxin-6-yl)-4-[2-(4-fluorophenyl)-6-methylpyrazolo[1,5-b]pyridazin-3-yl]-2-pyrimidinamine;

4-[2-(4-fluorophenyl)-6-methylpyrazolo[1,5-b]pyridazin-3-yl]-N-[3-(trifluoromethyl)phenyl]-2-pyrimidinamine;

N-[4-chloro-3-(trifluoromethyl)phenyl]-4-[2-(4-fluorophenyl)-6-methylpyrazolo[-1,5-b]pyridazin-3-yl]-2-pyrimidinamine;

N-(3,4-difluorophenyl)4-[2-(4-fluorophenyl)-6-methylpyrazolo[-1,5-b]pyridazin-3-yl]-2-pyrimidinamine;
or a salt thereof.

8. A pharmaceutical composition, comprising:
a compound as claimed in claim 7, or a salt thereof and one or more of pharmaceutically acceptable carriers, diluents and excipients.

\* \* \* \* \*